United States Patent [19]
Martin et al.

[11] 3,993,694
[45] Nov. 23, 1976

[54] TETRACYCLINE DERIVATIVES AND PROCESS FOR PREPARING THEM

[75] Inventors: Wolfgang Martin, Kelkheim, Taunus; Walter Dürckheimer, Hattersheim, Main; Elmar Schrinner, Wiesbaden, all of Germany

[73] Assignee: Hoechst Aktiengesellschaft, Frankfurt am Main, Germany

[22] Filed: Apr. 11, 1975

[21] Appl. No.: 567,115

[30] Foreign Application Priority Data
Apr. 13, 1974 Germany............................ 2418142

[52] U.S. Cl.................... 260/559 AT; 260/247.2 A; 260/268 PT; 260/293.76; 260/326.8; 424/227
[51] Int. Cl.²........................................ C07C 103/37
[58] Field of Search .............. 260/559 AT, 247.2 A, 260/268 PT, 293.76, 326.8; 424/227

[56] References Cited
UNITED STATES PATENTS
3,456,007   7/1969   Rondelet...................... 260/559 AT

*Primary Examiner*—C. Davis
*Attorney, Agent, or Firm*—Curtis, Morris & Safford

[57] ABSTRACT

Antibacterially-active tetracyclines, substituted at the amide group, and physiologically-tolerable salts thereof, said tetracyclines having the formula

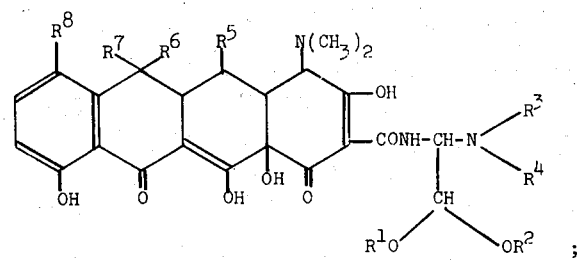

methods of making the same; pharmaceutical compositions containing the same.

10 Claims, No Drawings

TETRACYCLINE DERIVATIVES AND PROCESS FOR PREPARING THEM

The present invention relates to tetracycline derivatives and to a process for preparing them.

It is known that tetracyclines can be subjected to a reaction at the 2-carbonamide group with aldehydes and amines to form the corresponding amino-alkyl derivatives. While it is possible to vary the amine component within wide limits, the choice of the carbonyl component is restricted. Thus, for example, ketones are not suitable for this reaction and among the aldehydes only those react well which are particularly reactive, for example formaldehyde.

Now, we have found that water-soluble tetracycline derivatives can be prepared in unexpected easy manner when using aldehydes of the type of glyoxal-monoacetal.

Hence, the present invention provides tetracyclines which are substituted at the amide group and correspond to the general formula I

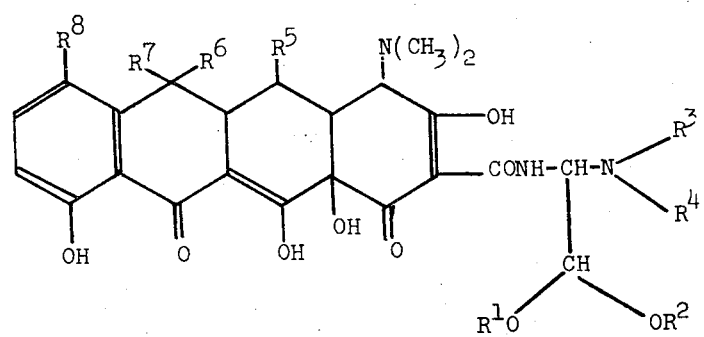

in which $R^1$ and $R^2$, which may be identical or different, represent a low molecular alkyl group of 1 to 5 carbon atoms or, together, an ethylene or propylene group, $R^3$ and $R^4$, which may be identical or different, represent hydrogen, alkyl of 1 to 6 carbon atoms, preferably 1 to 4 carbon atoms, which may be branched and which may be substituted once or several times by identical or different substituents of the series of hydroxyl groups, low molecular dialkylamino groups, low molecular dialkyl-carbamoyl groups, low molecular alkoxy-carbonyl groups, phenyl groups, a heterocyclic radical, in particular a 5- or 6-membered ring which may be interrupted by oxygen and/or nitrogen, or an carboxyl group, and in which latter case the alkyl group may also be substituted additionally by an amino group, or a cycloalkyl group of 5 to 7 carbon atoms, and in which $R^3$ and $R^4$ may also be closed to a 5- or 6-membered ring which may be interrupted by a nitrogen or oxygen atom and which may be substituted by low molecular alkyl, low molecular hydroxyalkyl, low molecular carboxyalkyl, hydroxyl or carbonyl, $R^5$ and $R^6$, which may be identical or different, represent hydrogen or a hydroxy group, $R^7$ repreents hydrogen or a methyl group, $R^6$ and $R^7$ together represent a methylene group, and $R^8$ represents hydrogen, chlorine, bromine or a low molecular dialkyl-amino group of 1 to 4 carbon atoms, and their physiologically tolerated salts.

The invention furthermore relates to a process for preparing the above-identified compounds of the general formula I, which comprises reacting a tetracycline of the formula II

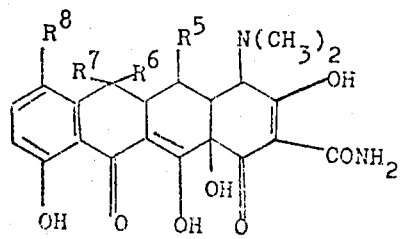

in which the radicals $R^5$ to $R^8$ have the meanings given above, optionally in the form of its salt, with an aldehyde of the formula III

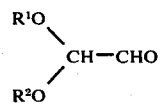

in which $R^1$ and $R^2$ have the meanings given above, and with an amine of the formula IV

in which the radicals $R^3$ and $R^4$ have the meanings given above.

As compounds of the formula II, there may be used all tetracyclines having an unsubstituted amide group and prepared by fermentation methods or by partial synthesis, for example tetracycline, oxytetracycline, 7-chlorotetracycline, 7-bromo-tetracycline, 6-desmethyl-7-chlorotetracycline, 6-desmethyl-tetracycline, 6-desmethyl-6-desoxy-tetracycline, 6-desoxytetracycline, 6-desoxy-5-oxy-tetracycline, 4-desdimethylamino-5-oxytetracycline, 6-desmethyl-6-desoxy-7-dimethylamino-tetracycline, 6-desmethyl-6-desoxy-7-diethylamino-tetracycline, 6-desmethyl-6-desoxy-6-methylene-tetracycline and 6-desmethyl-6-desoxy-5-hydroxy-6-methylene-tetracycline.

Examples of the glyoxal-monoacetals are, in particular, the dimethyl-, diethyl-, dipropyl-, dibutyl-monoacetal and the cyclic ethylene-glycol monoacetal. The acetal component may be prepared according to the method described in Helv. Chem. Acta 18, 514 (1935).

As amino components of the formula IV to be used according to the invention, there may be mentioned, besides ammonia, for example the following primary or secondary aliphatic or heterocyclic amines: methylamine, ethylamine, n-propylamine, i-propylamine, n-butylamine, i-butylamine, pentylamine, hexylamine, dimethylamine, diethylamine, di-n-butylamine, di-n-hexylamine, cyclopentylamine, cyclohexylamine, cycloheptylamine, diethylamino-ethylamine, bis-(diethylaminoethyl)-amine, ethanolamine, diethanolamine, methylhydroxyethylamine, benzylamine, dibenzylamine, β-phenylethylamine, 2-morpholinoethylamine, 2-piperidinopropylamine, 2-pyrrolidino-ethylamine, dimethylcarbamoyl-ethylamine, glycine, alanine, leucine, threonine, valine, phenylalanine, aspartic acid, glutamic acid, α-aminobutyric acid, lysine, ornithine, arginine, proline, histidine, piperidine, pyrrolidine, piperazine, morpholine, α-methylpyrrolidine, α,β- or α,α-dimethylpyrrolidine, N-methylpiperazine, N-(β-hydroxyethyl)-piperazine and 4-carboxyethylpiperazine.

The process of the invention is carried out, for example, by dissolving or suspending a tetracycline of the formula II or a salt thereof in a suitable solvent, for example a low molecular alcohol such as ethanol, propanol, i-propanol butanol, glycol, or an ether such as glycol monomethyl ether, glycol dimethyl ether, dioxane, tetrahydrofurane, or in tetramethyl-urea, dimethylformamide, hexamethylphosphoric acid triamide, N-methyl-pyrrolidine, or in a low molecular halogenated hydrocarbon, for example chloroform or methylene chloride and allowing it to react at temperatures between about 0° and 100° C, preferably at about 20° to about 50° C. If excess quantities of compounds of the formula III or IV are used, the excess may vary within wide limits, for example between about 1 and about 10 moles. It is sufficient, however, to operate with about an equimolar amount or with a slight excess.

The reaction partners may be dissolved in any desired order or introduced in substance into the solvent. It is of advantage, however, to mix the glyoxalacetal III with the amino component IV in the solvent and then to add the tetracycline in solid form.

After stirring for several hours under an inert gas, for example nitrogen, the reaction time being, as a rule, about three hours when carrying out the reaction at room temperature, the reaction products can be obtained, for example by concentrating the solution under reduced pressure to less than one-third of its original volume of the solution and subsequent addition of a non-polar solvent, for example ether, petroleum ether or cyclohexane, in pure solid form.

The process of the invention may be carried out in one or two stages, for example as transaminoalkylation. For the transaminoalkylation which may be carried out with or without isolation of the aminoalkyl compound, there may be used, for example, aminoalkyl compounds of H-acidic compounds, for example water, alcohols, imides, secondary amines or malonic acid derivatives, which are then reacted with the tetracycline component.

As acids forming physiologically tolerated salts of the compounds of the formula I of the invention, there may be used, for example mineral acids such as hydrochloric acid, sulfuric acid, nitric acid, phosphoric acid, and organic acids such as acetic acid, citric acid, maleic acid, succinic acid and tartaric acid. The organic salt formers themselves may have a pharmaceutical action such as that of, for example, penicillins, cephalosporins, panthothenic acid, chloramphenicol-hemisuccinate, salicylic acid, ascorbic acid or nalidixinoic acid.

The salts of the products of the invention may be prepared, for example, by combining equimolar solutions of the components in polar solvents, for example water, alcohol or dimethylformamide, whereupon the salts may be isolated by precipitation, freeze-drying, evaporation or re-precipitation. In this process, the acid component may be added during or after the reaction of tetracycline, acetal and amine. The salts of the final products may also be obtained by using, according to the invention, the tetracycline or amino component in the form of their salts.

The easy formation of the products of the invention with very high yields is surprising, because this reaction normally proceeds with low yield with other aldehydes, with the exception of formaldehyde. As the reactivity of acetaldehyde in reactions with tetracyclines and amines is considerably reduced in comparison to that of formaldehyde, it was not expected that the use of a substituted and branched acetaldehyde, which has, sterically, less favourable conditons for such a reaction, would lead to a smooth reaction with high yields.

Tetracyclines which are substituted at the 2-carboxamido group have been used for years successfully in the chemotherapy of bacterial infections.

The compounds of the invention are distinguished by a very good solubility in water and good tolerance, which makes them suitable especially for parenteral administration.

Another advantage of the compounds of the invention is their good stability in solution. Thus, for example, the solutions have a good stability with regard to colour change and clarity.

In addition, the products of the invention have a surprising and unexpected action against S. typhimurium which is stronger than that of tetracyclines.

For their administration, about 1 to 10% solutions, preferably about 2 to 5% aqueous solutions or also aqueous buffer solutions having a pH-value of between about 4 and 9, are used.

The products of the invention may also be used, for example in the form of tablets, dragees or capsules manufactured with the use of the usual adjuvants and excipients, for example starch, talcum, lactose, and so on.

The quantity of active substance in a sngle dose may be in the range of between about 200 and about 1500 mg, preferably between about 250 and about 500 mg.

It is also possible to combine the compounds of the invention with other therapeutic agents, for example penicillins, chloramphenicol, gentamycine or sulfonamides.

Examples of the compounds of the invention of the general formula I

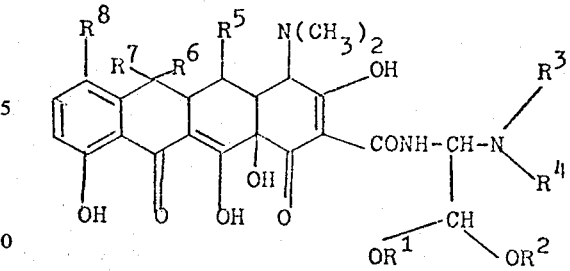

I are, for example, the derivatives of the tetracyclines indicated in Table I, the oxytetracyclines indicated in Table II, the chlorotetracyclines indicated in Table III, the 6-desoxy-oxytetracyclines of Table IV and the 6-desmethyl-7-chlorotetracyclines of Table V, the sections listed under the number A representing the compounds of particular importance. With a view to permit easier survey of the compounds regarding nomenclature, only the substituents $R^1$ to $R^8$ are indicated which, together with the compounds of the general formula I, represent the individual compounds.

Table IA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | H | OH | $CH_3$ | H |
| $CH_3$ | $CH_3$ | $C_2H_5$ | H | OH | $CH_3$ | H |
| $CH_3$ | $C_2H_5$ | $C_2H_5$ | H | OH | $CH_3$ | H |
| $CH_3$ | $n$-$C_3H_7$ | $n$-$C_3H_7$ | H | OH | $CH_3$ | H |
| $CH_3$ | $n$-$C_4H_9$ | $n$-$C_4H_9$ | H | OH | $CH_3$ | H |
| $CH_3$ | H | $CH_2$—COOH | H | OH | $CH_3$ | H |
| $CH_3$ | H | $CH_2$—$COOC_2H_5$ | H | OH | $CH_3$ | H |
| $CH_3$ | H | $CH_3$—CH(—)—COOH | H | OH | $CH_3$ | H |
| $CH_3$ | H | $CH_3$—CH(—)—$COOC_2H_5$ | H | OH | $CH_3$ | H |
| $CH_3$ | H | —$CH_2$—$CH_2$—COOH | H | OH | $CH_3$ | H |
| $CH_3$ | H | —$CH_2$—$CH_2$—$COOC_2H_5$ | H | OH | $CH_3$ | H |
| $CH_3$ | H | —$(CH_2)_4$—CH(—$NH_2$)—COOH | H | OH | $CH_3$ | H |
| $CH_3$ | \multicolumn{2}{c}{cyclopentyl (R_3 and R_4 form a 5-membered ring)} | H | OH | $CH_3$ | H |
| $CH_3$ | \multicolumn{2}{c}{cyclohexyl (R_3 and R_4 form a 6-membered ring)} | H | OH | $CH_3$ | H |
| $CH_3$ | \multicolumn{2}{c}{tetrahydropyranyl (6-membered ring with O)} | H | OH | $CH_3$ | H |
| $CH_3$ | \multicolumn{2}{c}{piperidinyl (6-membered ring with N)} | H | OH | $CH_3$ | H |
| $CH_3$ | \multicolumn{2}{c}{N-methylpiperidinyl (N—$CH_3$)} | H | OH | $CH_3$ | H |
| $CH_3$ | \multicolumn{2}{c}{N-ethylpiperidinyl (N—$C_2H_5$)} | H | OH | $CH_3$ | H |
| $CH_3$ | \multicolumn{2}{c}{N-(2-hydroxyethyl)piperidinyl (N—$C_2H_5OH$)} | H | OH | $CH_3$ | H |
| $C_2H_5$ | $CH_3$ | $CH_3$ | H | OH | $CH_3$ | H |
| $C_2H_5$ | $CH_3$ | $C_2H_5$ | H | OH | $CH_3$ | H |
| $C_2H_5$ | $C_2H_5$ | $C_2H_5$ | H | OH | $CH_3$ | H |

Table IA-continued

| $R_1, R_2$ | $R_3$ | $R_4$ | $R_5$ | $R_6$ | $R_7$ | $R_8$ |
|---|---|---|---|---|---|---|
| $C_2H_5$ | n-$C_3H_7$ | n-$C_3H_7$ | H | OH | $CH_3$ | H |
| $C_2H_5$ | n-$C_4H_9$ | n-$C_4H_9$ | H | OH | $CH_3$ | H |
| $C_2H_5$ | H | $CH_2$—COOH | H | OH | $CH_3$ | H |
| $C_2H_5$ | H | $CH_2$—$COOC_2H_5$ | H | OH | $CH_3$ | H |
| $C_2H_5$ | H | $CH_3$—CH—COOH<br>\| | H | OH | $CH_3$ | H |
| $C_2H_5$ | H | $CH_3$—CH—$COOC_{25}$<br>\| | H | OH | $CH_3$ | H |
| $C_2H_5$ | H | —$CH_2$—$CH_2$—COOH | H | OH | $CH_3$ | H |
| $C_2H_5$ | H | —$CH_2$—$CH_2$—$COOC_2H_5$ | H | OH | $CH_3$ | H |
| $C_2H_5$ | H | —$(CH_2)_4$—CH—COOH<br>\|<br>$NH_2$ | H | OH | $CH_3$ | H |
| $C_2H_5$ |  {cyclopentyl} | | H | OH | $CH_3$ | H |
| $C_2H_5$ |  {cyclohexyl} | | $CH_3$ | H | | |
| $C_2H_5$ |  {tetrahydropyranyl, O} | | H | OH | $CH_3$ | H |
| $C_2H_5$ |  {piperidinyl, N} | | H | OH | $CH_3$ | H |
| $C_2H_5$ | 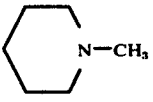 {N—$CH_3$ piperidinyl} | | H | OH | $CH_3$ | H |
| $C_2H_5$ | 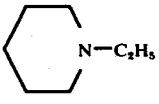 {N—$C_2H_5$ piperidinyl} | | H | OH | $CH_3$ | H |
| $C_2H_5$ | 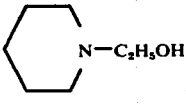 {N—$C_2H_5OH$ piperidinyl} | | H | OH | $CH_3$ | H |
| n-$C_3H_7$ | $CH_3$ | $CH_3$ | H | OH | $CH_3$ | H |
| n-$C_3H_7$ | $CH_3$ | $C_2H_5$ | H | OH | $CH_3$ | H |
| n-$C_3H_7$ | $C_2H_5$ | $C_2H_5$ | H | OH | $CH_3$ | H |
| n-$C_3H_7$ | n-$C_3H_7$ | n-$C_3H_7$ | H | OH | $CH_3$ | H |
| n-$C_3H_7$ | n-$C_4H_9$ | n-$C_4H_9$ | H | OH | $CH_3$ | H |
| n-$C_3H_7$ | H | $CH_2$—COOH | H | OH | $CH_3$ | H |
| n-$C_3H_7$ | H | $CH_2$—$COOC_2H_5$ | H | OH<br>$CH_3$ | H | |

Table IA-continued

| R₁, R₂ | R₃ | R₄ | R₅ | R₆ | R₇ | R₈ |
|---|---|---|---|---|---|---|
| n-C₃H₇ | H | CH₃—CH—COOH | H | OH | CH₃ | H |
| n-C₃H₇ | H | CH₃—CH—COOC₂H₅ | H | OH | CH₃ | H |
| n-C₃H₇ | H | —CH₂—CH₂—COOH | H | OH | CH₃ | H |
| n-C₃H₇ | H | —CH₂—COOC₂H₅ | H | OH | CH₃ | H |
| n-C₃H₇ | H | —(CH₂)₄—CH(NH₂)—COOH | H | OH | CH₃ | H |
| n-C₃H₇ | \multicolumn{2}{c}{cyclopentyl} | H | OH | CH₃ | H |
| n-C₃H₇ | \multicolumn{2}{c}{cyclohexyl} | H | OH | CH₃ | H |
| n-C₃H₇ | \multicolumn{2}{c}{tetrahydropyranyl} | H | OH | CH₃ | H |
| n-C₃H₇ | \multicolumn{2}{c}{piperidinyl (NH)} | H | OH | CH₃ | H |
| n-C₃H₇ | \multicolumn{2}{c}{piperidinyl (N—CH₃)} | H | OH | CH₃ | H |
| n-C₃H₇ | \multicolumn{2}{c}{piperidinyl (N—C₂H₅)} | H | OH | CH₃ | H |
| n-C₃H₇ | \multicolumn{2}{c}{piperidinyl (N—C₂H₄OH)} | H | OH | CH₃ | H |
| n-C₄H₉ | CH₃ | CH₃ | H | OH | CH₃ | H |
| n-C₄H₉ | CH₃ | C₂H₅ | H | OH | CH₃ | H |
| n-C₄H₉ | C₂H₅ | C₂H₅ | H | OH | CH₃ | H |
| n-C₄H₉ | n-C₃H₇ | n-C₃H₇ | H | OH | CH₃ | H |
| n-C₄H₉ | n-C₄H₉ | n-C₄H₉ | H | OH | CH₃ | H |
| n-C₄H₉ | H | CH₂—COOH | H | OH | CH₃ | H |
| n-C₄H₉ | H | CH₂—COOC₂H₅ | H | OH | CH₃ | H |
| n-C₄H₉ | H | CH₃—CH—COOH | H | OH | CH₃ | H |
| n-C₄H₉ | H | CH₃—CH—COOC₂H₅ | H | OH | CH₃ | H |
| n-C₄H₉ | H | —CH₂—CH₂—COOH | H | OH | CH₃ | H |
| n-C₄H₉ | H | —CH₂—CH₂—COOC₂H₅ | H | OH | CH₃ | H |

Table IA-continued

| R₁, R₂ | R₃ | R₄ | R₅ | R₆ | R₇ | R₈ |
|---|---|---|---|---|---|---|
| n-C₄H₉ | H | $-(CH_2)_4-\underset{\underset{NH_2}{|}}{CH}-COOH$ | H | OH | CH₃ | H |
| n-C₄H₉ |  |  | H | OH | CH₃ | H |
| n-C₄H₉ |  |  | H | OH | CH₃ | H |
| n-C₄H₉ |  |  | H | OH | CH₃ | H |
| n-C₄₉ |  |  | H | OH | CH₃ | H |
| n-C₄H₉ |  | 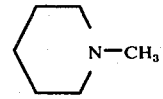 | H | OH | CH₃ | H |
| n-C₄H₉ |  | 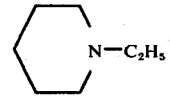 | H | OH | CH₃ | H |
| n-C₄H₉ |  | 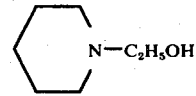 | H | OH | CH₃ | H |

Table IB

| R₁, R₂ | R₃ | R₄ | R₅ | R₆ | R₇ | R₈ |
|---|---|---|---|---|---|---|
| CH₃ | H | H | H | OH | CH₃ | H |
| CH₃ | H | CH₃ | H | OH | CH₃ | H |
| CH₃ | H | C₂H₅ | H | OH | CH₃ | H |
| CH₃ | H | n-C₃H₇ | H | OH | CH₃ | H |
| CH₃ | H | n-C₄H₉ | H | OH | CH₃ | H |
| CH₃ | H | i-C₃H₇ | H | OH | CH₃ | H |
| CH₃ | H | i-C₄H₉ | H | OH | CH₃ | H |
| CH₃ | H | n-C₅H₁₁ | H | OH | CH₃ | H |
| CH₃ | H | n-C₆H₁₃ | H | OH | CH₃ | H |
| CH₃ | H | C₂H₄OH | H | OH | CH₃ | H |
| CH₃ | H | $-CH_2-\underset{\underset{OH}{|}}{CH}-CH_3$ | H | OH | CH₃ | H |
| CH₃ | H | —CH₂—CH₂—CH₂OH | H | OH | CH₃ | H |
| CH₃ | H | —CH₂—CH₂—N(CH₃)₂ | H | OH | CH₃ | H |
| CH₃ | H | —CH₂—CH₂—N(C₂H₅)₂ | H | OH | CH₃ | H |
| CH₃ | H | —CH₂—CH₂—N(C₄H₉)₂ | H | OH | CH₃ | H |

Table IB-continued

| $R_1, R_2$ | $R_3$ | $R_4$ | $R_5$ | $R_6$ | $R_7$ | $R_8$ |
|---|---|---|---|---|---|---|
| $CH_3$ | H | $-CH_2-CH_2-CH_2-N(CH_3)_2$ | H | OH | $CH_3$ | H |
| $CH_3$ | H | $-CH_2-CH_2-CH_2-N(C_2H_5)_2$ | H | OH | $CH_3$ | H |
| $CH_3$ | H | $-CH_2-CON(CH_3)_2$ | H | OH | $CH_3$ | H |
| $CH_3$ | H | $-CH_2-CH_2-CON(CH_3)_2$ | H | OH | $CH_3$ | H |
| $CH_3$ | H | $-CH_2-CON(C_2H_5)_2$ | H | OH | $CH_3$ | H |
| $CH_3$ | H | $-CH_2-C_6H_5$ | H | OH | $CH_3$ | H |
| $CH_3$ | H | $-CH_2-CH_2-C_6H_5$ | H | OH | $CH_3$ | H |
| $CH_3$ | H | $-CH_2-CH_2-N\bigcirc$ (pyrrolidinyl) | H | OH | $CH_3$ | H |
| $CH_3$ | H | $-CH_2-CH_2-N\bigcirc O$ (morpholinyl) | H | OH | $CH_3$ | H |
| $CH_3$ | H | $-CH_2-CH_2-N\bigcirc$ (piperidinyl) | H | OH | $CH_3$ | H |
| $CH_3$ | H | $-CH_2-CH_2-N\bigcirc N-CH_3$ (N-methylpiperazinyl) | H | OH | $CH_3$ | H |
| $CH_3$ | $n-C_5H_{11}$ | $n-C_5H_{11}$ | H | OH | $CH_3$ | H |
| $CH_3$ | $n-C_6H_{13}$ | $n-C_6H_{13}$ | H | OH | $CH_3$ | H |
| $CH_3$ | $i-C_3H_7$ | $i-C_3H_7$ | H | OH | $CH_3$ | H |
| $CH_3$ | $i-C_4H_9$ | $i-C_4H_9$ | H | OH | $CH_3$ | H |
| $CH_3$ | $C_2H_4OH$ | $C_2H_4OH$ | H | OH | $CH_3$ | H |
| $CH_3$ | $-CH_2-CH(OH)-CH_3$ | $-CH_2-CH(OH)-CH_3$ | H | OH | $CH_3$ | H |
| $CH_3$ | $-CH_3$ | $C_2H_4OH$ | H | OH | $CH_3$ | H |
| $CH_3$ | $-CH_2-CH_2-CH_2OH$ | $-CH_2-CH_2-CH_2OH$ | H | OH | $CH_3$ | H |
| $CH_3$ | $-CH_2-C_6H_5$ | $-CH_2-C_6H_5$ | H | OH | $CH_3$ | H |
| $CH_3$ | $-CH_2-CH_2-C_6H_5$ | $-CH_2-CH_2-C_6H_5$ | H | OH | $CH_3$ | H |
| $CH_3$ | H | cyclopentyl | H | OH | $CH_3$ | H |
| $CH_3$ | H | cyclohexyl | H | OH | $CH_3$ | H |
| $CH_3$ | H | cycloheptyl | H | OH | $CH_3$ | H |
| $CH_3$ | $R_3$ and $R_4$ together: cyclohexyl-COOH | | H | OH | $CH_3$ | H |

Table IB-continued

| $R_1, R_2$ | $R_3$ | $R_4$ | $R_5$ | $R_6$ | $R_7$ | $R_8$ |
|---|---|---|---|---|---|---|
| $CH_3$ | | cyclohexyl–$CH_2$–COOH | H | OH | $CH_3$ | H |
| $CH_3$ | | cyclohexyl–$CH_2$–$CH_2$–COOH | H | OH | $CH_3$ | H |
| $CH_3$ | | cyclopentyl–COOH | H | OH | $CH_3$ | H |
| $CH_3$ | | cyclohexyl with COOH and OH | H | OH | $CH_3$ | H |
| $C_2H_5$ | H | H | H | OH | $CH_3$ | H |
| $C_2H_5$ | H | $CH_3$ | H | OH | $CH_3$ | H |
| $C_2H_5$ | H | $C_2H_5$ | H | OH | $CH_3$ | H |
| $C_2H_5$ | H | n-$C_3H_7$ | H | OH | $CH_3$ | H |
| $C_2H_5$ | H | n-$C_4H_9$ | H | OH | $CH_3$ | H |
| $C_2H_5$ | H | i-$C_3H_7$ | H | OH | $CH_3$ | H |
| $C_2H_5$ | H | i-$C_4H_9$ | H | OH | $CH_3$ | H |
| $C_2H_5$ | H | n-$C_5H_{11}$ | H | OH | $CH_3$ | H |
| $C_2H_5$ | H | n-$C_6H_{13}$ | H | OH | $CH_3$ | H |
| $C_2H_5$ | H | $C_2H_4OH$ | H | OH | $CH_3$ | H |
| $C_2H_5$ | H | $-CH_2-CH(OH)-CH_3$ | H | OH | $CH_3$ | H |
| $C_2H_5$ | H | $-CH_2-CH_2-CH_2OH$ | H | OH | $CH_3$ | H |
| $C_2H_5$ | H | $-CH_2-CH_2-N(CH_3)_2$ | H | OH | $CH_3$ | H |
| $C_2H_5$ | H | $-CH_2-CH_2-N(C_2H_5)_2$ | H | OH | $CH_3$ | H |
| $C_2H_5$ | H | $-CH_2-CH_2-N(C_4H_9)_2$ | H | OH | $CH_3$ | H |
| $C_2H_5$ | H | $-CH_2-CH_2-CH_2-N(CH_3)_2$ | H | OH | $CH_3$ | H |
| $C_2H_5$ | H | $-CH_2-CH_2-CH_2-N(C_2H_5)_2$ | H | OH | $CH_3$ | H |
| $C_2H_5$ | H | $-CH_2-CON(CH_3)_2$ | H | OH | $CH_3$ | H |
| $C_2H_5$ | H | $-CH_2-CH_2-CON(CH_3)_2$ | H | OH | $CH_3$ | H |
| $C_2H_5$ | H | $-CH_2-CON(C_2H_5)_2$ | H | OH | $CH_3$ | H |
| $C_2H_5$ | H | $-CH_2-C_6H_5$ | H | OH | $CH_3$ | H |
| $C_2H_5$ | H | $-CH_2-CH_2-C_6H_5$ | H | OH | $CH_3$ | H |
| $C_2H_5$ | H | $-CH_2-CH_2-N$(pyrrolidinyl) | H | OH | $CH_3$ | H |
| $C_2H_5$ | H | $-CH_2-CH_2-N$(morpholinyl, O) | H | OH | $CH_3$ | H |

Table IB-continued

| $R_1, R_2$ | $R_3$ | $R_4$ | $R_5$ | $R_6$ | $R_7$ | $R_8$ |
|---|---|---|---|---|---|---|
| $C_2H_5$ | H | —CH₂—CH₂—N(piperidine) | H | OH | $CH_3$ | H |
| $C_2H_5$ | H | —CH₂—CH₂—N(piperazine)N—CH₃ | H | OH | $CH_3$ | H |
| $C_2H_5$ | n-$C_5H_{11}$ | n-$C_5H_{11}$ | H | OH | $CH_3$ | H |
| $C_2H_5$ | n-$C_6H_{13}$ | n-$C_6H_{13}$ | H | OH | $CH_3$ | H |
| $C_2H_5$ | i-$C_3H_7$ | i-$C_3H_7$ | H | OH | $CH_3$ | H |
| $C_2H_5$ | i-$C_4H_9$ | i-$C_4H_9$ | H | OH | $CH_3$ | H |
| $C_2H_5$ | $C_2H_4OH$ | $C_2H_4OH$ | H | OH | $CH_3$ | H |
| $C_2H_5$ | —CH₂—CH(OH)—CH₃ | —CH₂—CH(OH)—CH₃ | H | OH | $CH_3$ | H |
| $C_2H_5$ | —$CH_3$ | $C_2H_4OH$ | H | OH | $CH_3$ | H |
| $C_2H_5$ | —CH₂—CH₂—CH₂OH | —CH₂—CH₂—CH₂OH | H | OH | $CH_3$ | H |
| $C_2H_5$ | —CH₂—$C_6H_5$ | —CH₂—$C_6H_5$ | H | OH | $CH_3$ | H |
| $C_2H_5$ | —CH₂—CH₂—$C_6H_5$ | —CH₂—CH₂—$C_6H_5$ | H | OH | $CH_3$ | H |
| $C_2H_5$ | H | cyclopentyl | H | OH | $CH_3$ | H |
| $C_2H_5$ | H | cyclohexyl | H | OH | $CH_3$ | H |
| $C_2H_5$ | H | cyclooctyl | H | OH | $CH_3$ | H |
| $C_2H_5$ | cyclohexyl-COOH | | H | H | $CH_3$ | H |
| $C_2H_5$ | cyclohexyl-CH₂—COOH | | H | OH | $CH_3$ | H |
| $C_2H_5$ | cyclohexyl-CH₂—CH₂—COOH | | H | OH | $CH_3$ | H |
| $C_2H_5$ | cyclopentyl-COOH | | H | OH | $CH_3$ | H |

Table IB-continued

| $R_1, R_2$ | $R_3$ | $R_4$ | $R_5$ | $R_6$ | $R_7$ | $R_8$ |
|---|---|---|---|---|---|---|
| $C_2H_5$ | COOH, cyclopentyl-OH | | H | OH | $CH_3$ | H |
| n-$C_3H_7$ | H | H | H | OH | $CH_3$ | H |
| n-$C_3H_7$ | H | $CH_3$ | H | OH | $CH_3$ | H |
| n-$C_3H_7$ | H | $C_2H_5$ | H | OH | $CH_3$ | H |
| n-$C_3H_7$ | H | n-$C_3H_7$ | H | OH | $CH_3$ | H |
| n-$C_3H_7$ | H | n-$C_4H_9$ | H | OH | $CH_3$ | H |
| n-$C_3H_7$ | H | i-$C_3H_7$ | H | OH | $CH_3$ | H |
| n-$C_3H_7$ | H | i-$C_4H_9$ | H | OH | $CH_3$ | H |
| n-$C_3H_7$ | H | n-$C_5H_{11}$ | H | OH | $CH_3$ | H |
| n-$C_3H_7$ | H | n-$C_6H_{13}$ | H | OH | $CH_3$ | H |
| n-$C_3H_7$ | H | $C_2H_4OH$ | H | OH | $CH_3$ | H |
| n-$C_3H_7$ | H | $-CH_2-CH(OH)-CH_3$ | H | OH | $CH_3$ | H |
| n-$C_3H_7$ | H | $-CH_2-CH_2-CH_2OH$ | H | OH | $CH_3$ | H |
| n-$C_3H_7$ | H | $-CH_2-CH_2-N(CH_3)_2$ | H | OH | $CH_3$ | H |
| n-$C_3H_7$ | H | $-CH_2-CH_2-N(C_2H_5)_2$ | H | OH | $CH_3$ | H |
| n-$C_3H_7$ | H | $-CH_2-CH_2-N(C_4H_9)_2$ | H | OH | $CH_3$ | H |
| n-$C_3H_7$ | H | $-CH_2-CH_2-CH_2-N(CH_3)_2$ | H | OH | $CH_3$ | H |
| n-$C_3H_7$ | H | $-CH_2-CH_2-CH_2-N(C_2H_5)_2$ | H | OH | $CH_3$ | H |
| n-$C_3H_7$ | H | $-CH_2-CON(CH_3)_2$ | H | OH | $CH_3$ | H |
| n-$C_3H_7$ | H | $-CH_2-CH_2-CON(CH_3)_2$ | H | OH | $CH_3$ | H |
| n-$C_3H_7$ | H | $-CH_2-CON(C_2H_5)_2$ | H | OH | $CH_3$ | H |
| n-$C_3H_7$ | H | $-CH_2-C_6H_5$ | H | OH | $CH_3$ | H |
| n-$C_3H_7$ | H | $-CH_2-CH_2-C_6H_5$ | H | OH | $CH_3$ | H |
| n-$C_3H_7$ | H | $-CH_2-CH_2-N$(pyrrolidinyl) | H | OH | $CH_3$ | H |
| n-$C_3H_7$ | H | $-CH_2-CH_2-N$(morpholinyl) | H | OH | $CH_3$ | H |
| n-$C_3H_7$ | H | $-CH_2-CH_2-N$(piperidinyl) | H | OH | $CH_3$ | H |
| n-$C_3H_7$ | H | $-CH_2-CH_2-N$(N-methylpiperazinyl)$-CH_3$ | H | OH | $CH_3$ | H |
| n-$C_3H_7$ | n-$C_5H_{11}$ | n-$C_5H_{11}$ | H | OH | $CH_3$ | H |
| n-$C_3H_7$ | n-$C_6H_{13}$ | n-$C_6H_{13}$ | H | OH | $CH_3$ | H |
| n-$C_3H_7$ | i-$C_3H_7$ | i-$C_3H_7$ | H | OH | $CH_3$ | H |
| n-$C_3H_7$ | i-$C_4H_9$ | i-$C_4H_9$ | H | OH | $CH_3$ | H |
| n-$C_3H_7$ | $C_2H_4OH$ | $C_2H_4OH$ | H | OH | $CH_3$ | H |

Table IB-continued

| $R_1, R_2$ | $R_3$ | $R_4$ | $R_5$ | $R_6$ | $R_7$ | $R_8$ |
|---|---|---|---|---|---|---|
| n-$C_3H_7$ | —$CH_2$—CH(OH)—$CH_3$ | —$CH_2$—CH(OH)—$CH_3$ | H | OH | $CH_3$ | H |
| n-$C_3H_7$ | —$CH_3$ | $C_2H_4OH$ | H | OH | $CH_3$ | H |
| n-$C_3H_7$ | —$CH_2$—$CH_2$—$CH_2OH$ | —$CH_2$—$CH_2$—$CH_2OH$ | H | OH | $CH_3$ | H |
| n-$C_3H_7$ | —$CH_2$—$C_6H_5$ | —$CH_2$—$C_6H_5$ | H | OH | $CH_3$ | H |
| n-$C_3H_7$ | —$CH_2$—$CH_2$—$C_6H_5$ | —$CH_2$—$CH_2$—$C_6H_5$ | H | OH | $CH_3$ | H |
| n-$C_3H_7$ | H | cyclopentyl | H | OH | $CH_3$ | H |
| n-$C_3H_7$ | H | cyclohexyl | H | OH | $CH_3$ | H |
| n-$C_3H_7$ | H | cyclooctyl | H | OH | $CH_3$ | H |
| n-$C_3H_7$ | | cyclohexyl-COOH | H | OH | $CH_3$ | H |
| n-$C_3H_7$ | | cyclohexyl-$CH_2$-COOH | H | OH | $CH_3$ | H |
| n-$C_3H_7$ | | cyclohexyl-$CH_2$-$CH_2$-COOH | H | OH | $CH_3$ | H |
| n-$C_3H_7$ | | cyclopentyl-COOH | H | OH | $CH_3$ | H |
| n-$C_3H_7$ | | 2-hydroxy-cyclopentyl-COOH | H | OH | $CH_3$ | H |
| n-$C_4H_9$ | H | H | H | OH | $CH_3$ | H |
| n-$C_4H_9$ | H | $CH_3$ | H | OH | $CH_3$ | H |
| n-$C_4H_9$ | H | $C_2H_5$ | H | OH | $CH_3$ | H |
| n-$C_4H_9$ | H | n-$C_3H_7$ | H | OH | $CH_3$ | H |
| n-$C_4H_9$ | H | n-$C_4H_9$ | H | OH | $CH_3$ | H |
| n-$C_4H_9$ | H | i-$C_3H_7$ | H | OH | $CH_3$ | H |
| n-$C_4H_9$ | H | i-$C_4H_9$ | H | OH | $CH_3$ | H |
| n-$C_4H_9$ | H | n-$C_5H_{11}$ | H | OH $CH_3$ | H | |
| n-$C_4H_9$ | H | n-$C_6H_{13}$ | H | OH | $CH_3$ | H |
| n-$C_4H_9$ | H | $C_2H_4OH$ | H | OH | $CH_3$ | H |

Table IB-continued

| $R_1, R_2$ | $R_3$ | $R_4$ | $R_5$ | $R_6$ | $R_7$ | $R_8$ |
|---|---|---|---|---|---|---|
| n-$C_4H_9$ | H | —$CH_2$—CH—$CH_3$<br>　　　　　OH | H | OH | $CH_3$ | H |
| n-$C_4H_9$ | H | —$CH_2$—$CH_2$—$CH_2OH$ | H | OH | $CH_3$ | H |
| n-$C_4H_9$ | H | —$CH_2$—$CH_2$—$N(CH_3)_2$ | H | OH | $CH_3$ | H |
| n-$C_4H_9$ | H | —$CH_2$—$CH_2$—$N(C_2H_5)_2$ | H | OH | $CH_3$ | H |
| n-$C_4H_9$ | H | —$CH_2$—$CH_2$—$N(C_4H_9)_2$ | H | OH | $CH_3$ | H |
| n-$C_4H_9$ | H | —$CH_2$—$CH_2$—$CH_2$—$N(CH_3)_2$ | H | OH | $CH_3$ | H |
| n-$C_4H_9$ | H | —$CH_2$—$CH_2$—$CH_2$—$N(C_2H_5)_2$ | H | OH | $CH_3$ | H |
| n-$C_4H_9$ | H | —$CH_2$—$CON(CH_3)_2$ | H | OH | $CH_3$ | H |
| n-$C_4H_9$ | H | —$CH_2$—$CH_2$—$CON(CH_3)_2$ | H | OH | $CH_3$ | H |
| n-$C_4H_9$ | H | —$CH_2$—$CON(C_2H_5)_2$ | H | OH | $CH_3$ | H |
| n-$C_4H_9$ | H | —$CH_2$—$C_6H_5$ | H | OH | $CH_3$ | H |
| n-$C_4H_9$ | H | —$CH_2$—$CH_2$—$C_6H_5$ | H | OH | $CH_3$ | H |
| n-$C_4H_9$ | H | —$CH_2$—$CH_2$—N⟨pyrrolidinyl⟩ | H | OH | $CH_3$ | H |
| n-$C_4H_9$ | H | —$CH_2$—$CH_2$—N⟨morpholinyl⟩O | H | OH | $CH_3$ | H |
| n-$C_4H_9$ | H | —$CH_2$—$CH_2$—N⟨piperidinyl⟩ | H | OH | $CH_3$ | H |
| n-$C_4H_9$ | H | —$CH_2$—$CH_2$—N⟨piperazinyl⟩N—$CH_3$ | H | OH | $CH_3$ | H |
| n-$C_4H_9$ | n-$C_5H_{11}$ | n-$C_5H_{11}$ | H | OH | $CH_3$ | H |
| n-$C_4H_9$ | n-$C_6H_{13}$ | n-$C_6H_{13}$ | H | OH | $CH_3$ | H |
| n-$C_4H_9$ | i-$C_3H_7$ | i-$C_3H_7$ | H | OH | $CH_3$ | H |
| n-$C_4H_9$ | i-$C_4H_9$ | i-$C_4H_9$ | H | OH | $CH_3$ | H |
| n-$C_4H_9$ | $C_2H_4OH$ | $C_2H_4OH$ | H | OH | $CH_3$ | H |
| n-$C_4H_9$ | —$CH_2$—CH—$CH_3$<br>　　　　OH | —$CH_2$—CH—$CH_3$<br>　　　　OH | H | OH | $CH_3$ | H |
| n-$C_4H_9$ | —$CH_3$ | $C_2H_4OH$ | H | OH | $CH_3$ | H |
| n-$C_4H_9$ | —$CH_2$—$CH_2$—$CH_2OH$ | —$CH_2$—$CH_2$—$CH_2OH$ | H | OH | $CH_3$ | H |
| n-$C_4H_9$ | —$CH_2$—$C_6H_5$ | —$CH_2$—$C_6H_5$ | H | OH | $CH_3$ | H |
| n-$C_4H_9$ | —$CH_2$—$CH_2$—$C_6H_5$ | —$CH_2$—$CH_2$—$C_6H_5$ | H | OH | $CH_3$ | H |
| n-$C_4H_9$ | H | cyclopentyl | H | OH | $CH_3$ | H |
| n-$C_4H_9$ | H | cyclohexyl | H | OH | $CH_3$ | H |

Table IB-continued

| $R_1$, $R_2$ | $R_3$ | $R_4$ | $R_5$ | $R_6$ | $R_7$ | $R_8$ |
|---|---|---|---|---|---|---|
| n-C$_4$H$_9$ | H |  | H | OH | CH$_3$ | H |
| n-C$_4$H$_9$ | | 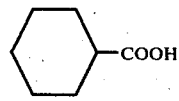 | H | OH | CH$_3$ | H |
| n-C$_4$H$_9$ | | 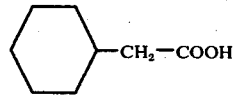 | H | OH | CH$_3$ | H |
| n-C$_4$H$_9$ | | 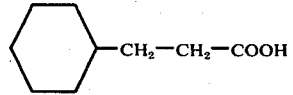 | H | OH | CH$_3$ | H |
| n-C$_4$H$_9$ | |  | H | OH | CH$_3$ | H |
| n-C$_4$H$_9$ | | 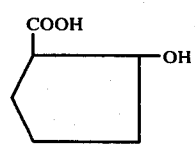 | H | OH | CH$_3$ | H |
| —(CH$_2$)$_2$— | H | H | H | OH | CH$_3$ | H |
| —(CH$_2$)$_2$— | H | CH$_3$ | H | OH | CH$_3$ | H |
| —(CH$_2$)$_2$— | H | C$_2$H$_5$ | H | OH | CH$_3$ | H |
| —(CH$_2$)$_2$— | H | n-C$_3$H$_7$ | H | OH | CH$_3$ | H |
| —(CH$_2$)$_2$— | H | n-C$_4$H$_9$ | H | OH | CH$_3$ | H |
| —(CH$_2$)$_2$— | H | i-C$_3$H$_7$ | H | OH | CH$_3$ | H |
| —(CH$_2$)$_2$— | H | i-C$_4$H$_9$ | H | OH | CH$_3$ | H |
| —(CH$_2$)$_2$— | H | n-C$_5$H$_{11}$ | H | OH | CH$_3$ | H |
| —(CH$_2$)$_2$— | H | n-C$_6$H$_{13}$ | H | OH | CH$_3$ | H |
| —(CH$_2$)$_2$— | H | C$_2$H$_4$OH | H | OH | CH$_3$ | H |
| —(CH$_2$)$_2$— | H | —CH$_2$—CH(OH)—CH$_3$ | H | OH | CH$_3$ | H |
| —(CH$_2$)$_2$— | H | —CH$_2$—CH$_2$—CH$_2$OH | H | OH | CH$_3$ | H |
| —(CH$_2$)$_2$— | H | —CH$_2$—CH$_2$—N(CH$_3$)$_2$ | H | OH | CH$_3$ | H |
| —(CH$_2$)$_2$— | H | —CH$_2$—CH$_2$—N(C$_2$H$_5$)$_2$ | H | OH | CH$_3$ | H |
| —(CH$_2$)$_2$— | H | —CH$_2$—CH$_2$—N(C$_4$H$_9$)$_2$ | H | OH | CH$_3$ | H |
| —(CH$_2$)$_2$— | H | —CH$_2$—CH$_2$—CH$_2$—N(CH$_3$)$_2$ | H | OH | CH$_3$ | H |
| —(CH$_2$)$_2$— | H | —CH$_2$—CH 2—CH$_2$—N(C$_2$H$_5$)$_2$ | H | OH | CH$_3$ | H |
| —(CH$_2$)$_2$— | H | —CH$_2$—CON(CH$_3$)$_2$ | H | OH | CH$_3$ | H |
| —(CH$_2$)$_2$— | H | —CH$_2$—CH$_2$—CON(CH$_3$)$_2$ | H | OH | CH$_3$ | H |
| —(CH$_2$)$_2$— | H | —CH$_2$—CON(C$_2$H$_5$)$_2$ | H | OH | CH$_3$ | H |
| —(CH$_2$)$_2$— | H | —CH$_2$—C$_6$H$_5$ | H | OH | CH$_3$ | H |
| —(CH$_2$)$_2$— | H | —CH$_2$—CH$_2$—C$_6$H$_5$ | H | OH | CH$_3$ | H |

Table IB-continued

| $R_1, R_2$ | $R_3$ | $R_4$ | $R_5$ | $R_6$ | $R_7$ | $R_8$ |
|---|---|---|---|---|---|---|
| —(CH$_2$)$_2$— | H | H | OH | CH$_3$ | H | |
| | —CH$_2$—CH$_2$—N⟨ ⟩ | | | | | |
| —(CH$_2$)$_2$— | H | —CH$_2$—CH$_2$—N⟨O⟩ | H | OH | CH$_3$ | H |
| —(CH$_2$)$_2$— | H | —CH$_2$—CH$_2$—N⟨ ⟩ | H | OH | CH$_3$ | H |
| —(CH$_2$)$_2$— | H | —CH$_2$—CH$_2$—N⟨ ⟩N—CH$_3$ | H | OH | CH$_3$ | H |
| —(CH$_2$)$_2$— | n-C$_5$H$_{11}$ | n-C$_5$H$_{11}$ | H | OH | CH$_3$ | H |
| —(CH$_2$)$_2$— | n-C$_6$H$_{13}$ | n-C$_6$H$_{13}$ | H | OH | CH$_3$ | H |
| —(CH$_2$)$_2$— | i-C$_3$H$_7$ | i-C$_3$H$_7$ | H | OH | CH$_3$ | H |
| —(CH$_2$)$_2$— | i-C$_4$H$_9$ | i-C$_4$H$_9$ | H | OH | CH$_3$ | H |
| —(CH$_2$)$_2$— | C$_2$H$_4$OH | C$_2$H$_4$OH | H | OH | CH$_3$ | H |
| —(CH$_2$)$_2$— | —CH$_2$—CH—CH$_3$<br>　　　　　OH | —CH$_2$—CH—CH$_3$<br>　　　　　OH | H | OH<br>CH$_3$ | H | |
| —(CH$_2$)$_2$— | —CH$_3$ | C$_2$H$_4$OH | H | OH | CH$_3$ | H |
| —(CH$_2$)$_2$— | —CH$_2$—CH$_2$—CH$_2$OH | —CH$_2$—CH$_2$—CH$_2$OH | H | OH | CH$_3$ | H |
| —(CH$_2$)$_2$— | —CH$_2$—C$_6$H$_5$ | —CH$_2$—C$_6$H$_5$ | H | OH | CH$_3$ | H |
| —(CH$_2$)$_2$— | —CH$_2$—CH$_2$—C$_6$H$_5$ | —CH$_2$—CH$_2$—C$_6$H$_5$ | H | OH | CH$_3$ | H |
| —(CH$_2$)$_2$— | H | ⟨cyclopentyl⟩ | H | OH | CH$_3$ | H |
| —(CH$_2$)$_2$— | H | ⟨cyclohexyl⟩ | H | OH | CH$_3$ | H |
| —(CH$_2$)$_2$— | H | ⟨cycloheptyl⟩ | H | OH | CH$_3$ | H |
| —(CH$_2$)$_2$— | ⟨cyclohexyl⟩—COOH | | H | OH | CH$_3$ | H |
| —(CH$_2$)$_2$— | ⟨cyclohexyl⟩—CH$_2$—COOH | | H | OH | CH$_3$ | H |
| —(CH$_2$)$_2$— | ⟨cyclohexyl⟩—CH$_2$—CH$_2$—COOH | | H | OH | CH$_3$ | H |

Table IB-continued

| $R_1, R_2$ | $R_3$ | $R_4$ | $R_5$ | $R_6$ | $R_7$ | $R_8$ |
|---|---|---|---|---|---|---|
| —(CH$_2$)$_2$— | | cyclopentyl-COOH | H | OH | CH$_3$ | H |
| —(CH$_2$)$_2$— | | cyclopentyl (COOH, OH) | H | OH | CH$_3$ | H |
| —(CH$_2$)$_3$— | H | H | H | OH | CH$_3$ | H |
| —(CH$_2$)$_3$— | H | CH$_3$ | H | OH | CH$_3$ | H |
| —(CH$_2$)$_3$— | H | C$_2$H$_5$ | H | OH | CH$_3$ | H |
| —(CH$_2$)$_3$— | H n-C$_3$H$_7$ | H | OH | CH$_3$ | H | |
| —(CH$_2$)$_3$— | H | n-C$_4$H$_9$ | H | OH | CH$_3$ | H |
| —(CH$_2$)$_3$— | H | i-C$_3$H$_7$ | H | OH | CH$_3$ | H |
| —(CH$_2$)$_3$— | H | i-C$_4$H$_9$ | H | OH | CH$_3$ | H |
| —(CH$_2$)$_3$— | H | n-C$_5$H$_{11}$ | H | OH | CH$_3$ | H |
| —(CH$_2$)$_3$— | H | n-C$_6$H$_{13}$ | H | OH | CH$_3$ | H |
| —(CH$_2$)$_3$— | H | C$_2$H$_4$OH | H | OH | CH$_3$ | H |
| —(CH$_2$)$_3$— | H | —CH$_2$—CH(OH)—CH$_3$ | H | OH | CH$_3$ | H |
| —(CH$_2$)$_3$— | H | —CH$_2$—CH$_2$—CH$_2$OH | H | OH | CH$_3$ | H |
| —(CH$_2$)$_3$— | H | —CH$_2$—CH$_2$—N(CH$_3$)$_2$ | H | OH | CH$_3$ | H |
| —(CH$_2$)$_3$— | H | —CH$_2$—CH$_2$—N(C$_2$H$_5$)$_2$ | H | OH | CH$_3$ | H |
| —(CH$_2$)$_3$— | H | —CH$_2$—CH$_2$—N(C$_4$H$_9$)$_2$ | H | OH | CH$_3$ | H |
| —(CH$_2$)$_3$— | H | —CH$_2$—CH$_2$—CH$_2$—N(CH$_3$)$_2$ | H | OH | CH$_3$ | H |
| —(CH$_2$)$_3$— | H | —CH$_2$—CH$_2$—CH$_2$—N(C$_2$H$_5$)$_2$ | H | OH | CH$_3$ | H |
| —(CH$_2$)$_3$— | H | —CH$_2$—CON(CH$_3$)$_2$ | H | OH | CH$_3$ | H |
| —(CH$_2$)$_3$— | H | —CH$_2$—CH$_2$—CON(CH$_3$)$_2$ | H | OH | CH$_3$ | H |
| —(CH$_2$)$_3$— | H | —CH$_2$—CON(C$_2$H$_5$)$_2$ | H | OH | CH$_3$ | H |
| —(CH$_2$)$_3$— | H | —CH$_2$—C$_6$H$_5$ | H | OH | CH$_3$ | H |
| —(CH$_2$)$_3$— | H | —CH$_2$—CH$_2$—C$_6$H$_5$ | H | OH | CH$_3$ | H |
| —(CH$_2$)$_3$— | H | —CH$_2$—CH$_2$—N(pyrrolidinyl) | H | OH | CH$_3$ | H |
| —(CH$_2$)$_3$— | H | —CH$_2$—CH$_2$—N(morpholinyl) | H | OH | CH$_3$ | H |
| —(CH$_2$)$_3$— | H | —CH$_2$—CH$_2$—N(piperidinyl) | H | OH | CH$_3$ | H |
| —(CH$_2$)$_3$— | H | —CH$_2$—CH$_2$—N(N'-methylpiperazinyl) | H | OH | CH$_3$ | H |
| —(CH$_2$)$_3$— | n-C$_5$H$_{11}$ | n-C$_5$H$_{11}$ | H | OH | CH$_3$ | H |

Table IB-continued

| $R_1, R_2$ | $R_3$ | $R_4$ | $R_5$ | $R_6$ | $R_7$ | $R_8$ |
|---|---|---|---|---|---|---|
| $-(CH_2)_3-$ | $n-C_6H_{13}$ | $n-C_6H_{13}$ | H | OH | $CH_3$ | H |
| $-(CH_2)_3-$ | $i-C_3H_7$ | $i-C_3H_7$ | H | OH | $CH_3$ | H |
| $-(CH_2)_3-$ | $i-C_4H_9$ | $i-C_4H_9$ | H | OH | $CH_3$ | H |
| $-(CH_2)_3-$ | $C_2H_4OH$ | $C_2H_4OH$ | H | OH | $CH_3$ | H |
| $-(CH_2)_3-$ | $-CH_2-\underset{\underset{OH}{\mid}}{CH}-CH_3$ | $-CH_2-\underset{\underset{OH}{\mid}}{CH}-CH_3$ | H | OH | $CH_3$ | H |
| $-(CH_2)_3-$ | $-CH_3$ | $C_2H_4OH$ | H | OH | $CH_3$ | H |
| $-(CH_2)_3-$ | $-CH_2-CH_2-CH_2OH$ | $-CH_2-CH_2-CH_2OH$ | H | OH | $CH_3$ | H |
| $-(CH_2)_3-$ | $-CH_2-C_6H_5$ | $-CH_2-C_6H_5$ | H | OH | $CH_3$ | H |
| $-(CH_2)_3-$ | $-CH_2-CH_2-C_6H_5$ | $-CH_2-CH_2-C_6H_5$ | H | OH | $CH_3$ | H |
| $-(CH_2)_3-$ | H |  | H | OH | $CH_3$ | H |
| $-(CH_2)_3-$ | H |  | H | OH | $CH_3$ | H |
| $-(CH_2)_3-$ | H |  | H | OH | $CH_3$ | H |
| $-(CH_2)_3-$ | | 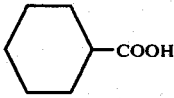 | H | OH | $CH_3$ | H |
| $-(CH_2)_3-$ | | 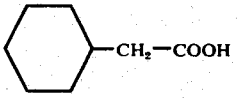 | H | OH | $CH_3$ | H |
| $-(CH_2)_3-$ | | 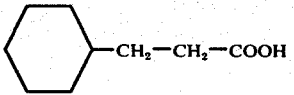 | H | OH | $CH_3$ | H |
| $-(CH_2)_3$ | |  | H | OH | $CH_3$ | H |
| $-(CH_2)_3-$ | | 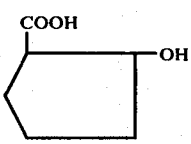 | H | OH | $CH_3$ | H |

TABLE IIA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | OH | OH | $CH_3$ | H |
| $CH_3$ | $CH_3$ | $C_2H_5$ | OH | OH | $CH_3$ | H |
| $CH_3$ | $C_2H_5$ | $C_2H_5$ | OH | OH | $CH_3$ | H |

TABLE IIA-continued

| R₁, R₂ | R₃ | R₄ | R₅ | R₆ | R₇ | R₈ |
|---|---|---|---|---|---|---|
| CH₃ | n-C₃H₇ | n-C₃H₇ | OH | OH | CH₃ | H |
| CH₃ | n-C₄H₉ | n-C₄H₉ | OH | OH | CH₃ | H |
| CH₃ | H | CH₂—COOH | OH | OH | CH₃ | H |
| CH₃ | H | CH₂—COOC₂H₅ | OH | OH | CH₃ | H |
| CH₃ | H | CH₃—CH—COOH | OH | OH | CH₃ | H |
| CH₃ | H | CH₃—CH—COOC₂H₅ | OH | OH | CH₃ | H |
| CH₃ | H | —CH₂—CH₂—COOH | OH | OH | CH₃ | H |
| CH₃ | H | —CH₂—CH₂—COOC₂H₅ | OH | OH | CH₃ | H |
| CH₃ | H | —(CH₂)₄—CH(NH₂)—COOH | OH | OH | CH₃ | H |
| CH₃ | \multicolumn{2}{c}{cyclopentyl ring (R₃+R₄)} | OH | OH | CH₃ | H |
| CH₃ | \multicolumn{2}{c}{cyclohexyl ring (R₃+R₄)} | OH | OH | CH₃ | H |
| CH₃ | \multicolumn{2}{c}{tetrahydropyranyl ring with O (R₃+R₄)} | OH | OH | CH₃ | H |
| CH₃ | \multicolumn{2}{c}{piperidyl ring N—H (R₃+R₄)} | OH | OH | CH₃ | H |
| CH₃ | \multicolumn{2}{c}{piperidyl ring N—CH₃ (R₃+R₄)} | OH | OH | CH₃ | H |
| CH₃ | \multicolumn{2}{c}{piperidyl ring N—C₂H₅ (R₃+R₄)} | OH | OH | CH₃ | H |
| CH₃ | \multicolumn{2}{c}{piperidyl ring N—C₂H₅OH (R₃+R₄)} | OH | OH | CH₃ | H |
| C₂H₅ | CH₃ | CH₃ | OH | OH | CH₃ | H |
| C₂H₅ | CH₃ | C₂H₅ | OH | OH | CH₃ | H |
| C₂H₅ | C₂H₅ | C₂H₅ | OH | OH | CH₃ | H |
| C₂H₅ | n-C₃H₇ | n-C₃H₇ | OH | OH | CH₃ | H |
| C₂H₅ | n-C₄H₉ | n-C₄H₉ | OH | OH | CH₃ | H |
| C₂H₅ | H | CH₂—COOH | OH | OH | CH₃ | H |
| C₂H₅ | H | CH₂—COOC₂H₅ | OH | OH | CH₃ | H |
| C₂H₅ | H | CH₃—CH—COOH | OH | OH | CH₃ | H |

TABLE IIA-continued

| $R_1, R_2$ | $R_3$ | $R_4$ | $R_5$ | $R_6$ | $R_7$ | $R_8$ |
|---|---|---|---|---|---|---|
| $C_2H_5$ | H | $CH_3-\underset{|}{CH}-COOC_2H_5$ | OH | OH | $CH_3$ | H |
| $C_2H_5$ | H | $-CH_2-CH_2-COOH$ | OH | OH | $CH_3$ | H |
| $C_2H_5$ | H | $-CH_2-CH_2-COOC_2H_5$ | OH | OH | $CH_3$ | H |
| $C_2H_5$ | H | $-(CH_2)_4-\underset{NH_2}{\overset{|}{CH}}-COOH$ | OH | OH | $CH_3$ | H |
| $C_2H_5$ | cyclopentyl | | OH | OH | $CH_3$ | H |
| $C_2H_5$ | cyclohexyl | | OH | OH | $CH_3$ | H |
| $C_2H_5$ | tetrahydropyranyl (O) | | OH | OH | $CH_3$ | H |
| $C_2H_5$ | piperidinyl (NH) | | OH | OH | $CH_3$ | H |
| $C_2H_5$ | N-methylpiperidinyl | | OH | OH | $CH_3$ | H |
| $C_2H_5$ | N-ethylpiperidinyl | | OH | OH | $CH_3$ | H |
| $C_2H_5$ | N-($C_2H_5OH$)piperidinyl | | OH | OH | $CH_3$ | H |
| $n-C_3H_7$ | $CH_3$ | $CH_3$ | OH | OH | $CH_3$ | H |
| $n-C_3H_7$ | $CH_3$ | $C_2H_5$ | OH | OH | $CH_3$ | H |
| $n-C_3H_7$ | $C_2H_5$ | $C_2H_5$ | OH | OH | $CH_3$ | H |
| $n-C_3H_7$ | $n-C_3H_7$ | $n-C_3H_7$ | OH | OH | $CH_3$ | H |
| $n-C_3H_7$ | $n-C_4H_9$ | $n-C_4H_9$ | OH | OH | $CH_3$ | H |
| $n-C_3H_7$ | H | $CH_2-COOH$ | OH | OH | $CH_3$ | H |
| $n-C_3H_7$ | H | $CH_2-COOC_2H_5$ | OH | OH | $CH_3$ | H |
| $n-C_3H_7$ | H | $CH_3-\underset{|}{CH}-COOH$ | OH | OH | $CH_3$ | H |
| $n-C_3H_7$ | H | $CH_3-\underset{|}{CH}-COOC_2H_5$ | OH | OH | $CH_3$ | H |
| $n-C_3H_7$ | H | $-CH_2-CH_2-COOH$ | OH | OH | $CH_3$ | H |
| $n-C_3H_7$ | H | $-CH_2-CH_2-COOC_2H_5$ | OH | OH | $CH_3$ | H |
| $n-C_3H_7$ | H | $-(CH_2)_4-\underset{NH_2}{\overset{|}{CH}}-COOH$ | OH | OH | $CH_3$ | H |

TABLE IIA-continued

| R₁, R₂ | R₃ | R₄ | R₅ | R₆ | R₇ | R₈ |
|---|---|---|---|---|---|---|
| n-C₃H₇ | \multicolumn{2}{c|}{cyclopentyl ring} | OH | OH | CH₃ | H |
| n-C₃H₇ | \multicolumn{2}{c|}{cyclohexyl ring} | OH | OH | CH₃ | H |
| n-C₃H₇ | \multicolumn{2}{c|}{tetrahydropyranyl (O)} | OH | OH | CH₃ | H |
| n-C₃H₇ | \multicolumn{2}{c|}{piperidinyl (NH)} | OH | OH | CH₃ | H |
| n-C₃H₇ | \multicolumn{2}{c|}{N—CH₃ piperidinyl} | OH | OH | CH₃ | H |
| n-C₃H₇ | \multicolumn{2}{c|}{N—C₂H₅ piperidinyl} | OH | OH | CH₃ | H |
| n-C₃H₇ | \multicolumn{2}{c|}{N—C₂H₅OH piperidinyl} | OH | OH | CH₃ | H |
| n-C₄H₉ | CH₃ | CH₃ | OH | OH | CH₃ | H |
| n-C₄H₉ | CH₃ | C₂H₅ | OH | OH | CH₃ | H |
| n-C₄H₉ | C₂H₅ | C₂H₅ | OH | OH | CH₃ | H |
| n-C₄H₉ | n-C₃H₇ | n-C₃H₇ | OH | OH | CH₃ | H |
| n-C₄H₉ | n-C₄H₉ | n-C₄H₉ | OH | OH | CH₃ | H |
| n-C₄H₉ | H | CH₂—COOH | OH | OH | CH₃ | H |
| n-C₄H₉ | H | CH₂—COOC₂H₅ | OH | OH | CH₃ | H |
| n-C₄H₉ | H | CH₃—CH—COOH | OH | OH | CH₃ | H |
| n-C₄H₉ | H | CH₃—CH—COOC₂H₅ | OH | OH | CH₃ | H |
| n-C₄H₉ | H | —CH₂—CH₂—COOH | OH | OH | CH₃ | H |
| n-C₄H₉ | H | —CH₂—CH₂—COOC₂H₅ | OH | OH | CH₃ | H |
| n-C₄H₉ | H | —(CH₂)₄—CH(NH₂)—COOH | OH | OH | CH₃ | H |
| n-C₄H₉ | \multicolumn{2}{c|}{cyclopentyl ring} | OH | OH | CH₃ | H |

TABLE IIA-continued

| $R_1, R_2$ | $R_3$ | $R_4$ | $R_5$ | $R_6$ | $R_7$ | $R_8$ |
|---|---|---|---|---|---|---|
| n-$C_4H_9$ | 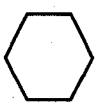 | | OH | OH | $CH_3$ | H |
| n-$C_4H_9$ | 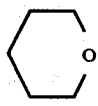 | | OH | OH | $CH_3$ | H |
| n-$C_4H_9$ |  | | OH | OH | $CH_3$ | H |
| n-$C_4H_9$ | 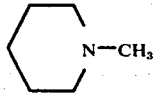 | | OH | OH | $CH_3$ | H |
| n-$C_4H_9$ | 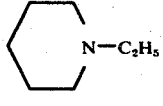 | | OH | OH | $CH_3$ | H |
| n-$C_4H_9$ | 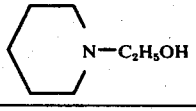 | | OH | OH | $CH_3$ | H |

Table IIB

| $R_1, R_2$ | $R_3$ | $R_4$ | $R_5$ | $R_6$ | $R_7$ | $R_8$ |
|---|---|---|---|---|---|---|
| $CH_3$ | H | H | OH | OH | $CH_3$ | H |
| $CH_3$ | H | $CH_3$ | OH | OH | $CH_3$ | H |
| $CH_3$ | H | $C_2H_5$ | OH | OH | $CH_3$ | H |
| $CH_3$ | H | n-$C_3H_7$ | OH | OH | $CH_3$ | H |
| $CH_3$ | H | n-$C_4H_9$ | OH | OH | $CH_3$ | H |
| $CH_3$ | H | i-$C_3H_7$ | OH | OH | $CH_3$ | H |
| $CH_3$ | H | i-$C_4H_9$ | OH | OH | $CH_3$ | H |
| $CH_3$ | H | n-$C_5H_{11}$ | OH | OH | $CH_3$ | H |
| $CH_3$ | H | n-$C_6H_{13}$ | OH | OH | $CH_3$ | H |
| $CH_3$ | H | $C_2H_4OH$ | OH | OH | $CH_3$ | H |
| $CH_3$ | H | $-CH_2-CH(OH)-CH_3$ | OH | OH | $CH_3$ | H |
| $CH_3$ | H | $-CH_2-CH_2-CH_2OH$ | OH | OH | $CH_3$ | H |
| $CH_3$ | H | $-CH_2-CH_2-N(CH_3)_2$ | OH | OH | $CH_3$ | H |
| $CH_3$ | H | $-CH_2-CH_2-N(C_2H_5)_2$ | OH | OH | $CH_3$ | H |
| $CH_3$ | H | $-CH_2-CH_2-N(C_4H_9)_2$ | OH | OH | $CH_3$ | H |
| $CH_3$ | H | $-CH_2-CH_2-CH_2-N(CH_3)_2$ | OH | OH | $CH_3$ | H |
| $CH_3$ | H | $-CH_2-CH_2-CH_2-N(C_2H_5)_2$ | OH | OH | $CH_3$ | H |
| $CH_3$ | H | $-CH_2-CON(CH_3)_2$ | OH | OH | $CH_3$ | H |
| $CH_3$ | H | $-CH_2-CH_2-CON(CH_3)_2$ | OH | OH | $CH_3$ | H |
| $CH_3$ | H | $-CH_2-CON(C_2H_5)_2$ | OH | OH | $CH_3$ | H |
| $CH_3$ | H | $-CH_2-C_6H_5$ | OH | OH | $CH_3$ | H |
| $CH_3$ | H | $-CH_2-CH_2-C_6H_5$ | OH | OH | $CH_3$ | H |

Table IIB-continued

| R₁, R₂ | R₃ | R₄ | R₅ | R₆ | R₇ | R₈ |
|---|---|---|---|---|---|---|
| CH₃ | H | -CH₂-CH₂-N(pyrrolidine) | OH | OH | CH₃ | H |
| CH₃ | H | -CH₂-CH₂-N(morpholine)O | OH | OH | CH₃ | H |
| CH₃ | H | -CH₂-CH₂-N(piperidine) | OH | OH | CH₃ | H |
| CH₃ | H | -CH₂-CH₂-N(piperazine)N-CH₃ | OH | OH | CH₃ | H |
| CH₃ | n-C₅H₁₁ | n-C₅H₁₁ | OH | OH | CH₃ | H |
| CH₃ | n-C₆H₁₃ | n-C₆H₁₃ | OH | OH | CH₃ | H |
| CH₃ | i-C₃H₇ | i-C₃H₇ | OH | OH | CH₃ | H |
| CH₃ | i-C₄H₉ | i-C₄H₉ | OH | OH | CH₃ | H |
| CH₃ | C₂H₄OH | C₂H₄OH | OH | OH | CH₃ | H |
| CH₃ | -CH₂-CH(OH)-CH₃ | -CH₂-CH(OH)-CH₃ | OH | OH | CH₃ | H |
| CH₃ | -CH₃ | C₂H₄OH | OH | OH | CH₃ | H |
| CH₃ | -CH₂-CH₂-CH₂OH | -CH₂-CH₂-CH₂OH | OH | OH | CH₃ | H |
| CH₃ | -CH₂-C₆H₅ | -CH₂-C₆H₅ | OH | OH | CH₃ | H |
| CH₃ | -CH₂-CH₂-C₆H₅ | -CH₂-CH₂-C₆H₅ | OH | OH | CH₃ | H |
| CH₃ | H | cyclopentyl | OH | OH | CH₃ | H |
| CH₃ | H | cyclohexyl | OH | OH | CH₃ | H |
| CH₃ | H | cycloheptyl | OH | OH | CH₃ | H |
| CH₃ | CH | cyclohexyl-COOH | OH | OH | CH₃ | H |
| CH₃ |  | cyclohexyl-CH₂-COOH | OH | OH | CH₃ | H |
| CH₃ |  | cyclohexyl-CH₂-CH₂-COOH | OH | OH | CH₃ | H |

Table IIB-continued

| $R_1, R_2$ | $R_3$ | $R_4$ | $R_5$ | $R_6$ | $R_7$ | $R_8$ |
|---|---|---|---|---|---|---|
| $CH_3$ | | cyclopentyl-COOH | OH | OH | $CH_3$ | H |
| $CH_3$ | COOH | cyclopentyl-OH | OH | OH | $CH_3$ | H |
| $C_2H_5$ | H | H | OH | OH | $CH_3$ | H |
| $C_2H_5$ | H | $CH_3$ | OH | OH | $CH_3$ | H |
| $C_2H_5$ | H | $C_2H_5$ | OH | OH | $CH_3$ | H |
| $C_2H_5$ | H | $n\text{-}C_3H_7$ | OH | OH | $CH_3$ | H |
| $C_2H_5$ | H | $n\text{-}C_4H_9$ | OH | OH | $CH_3$ | H |
| $C_2H_5$ | H | $i\text{-}C_3H_7$ | OH | OH | $CH_3$ | H |
| $C_2H_5$ | H | $i\text{-}C_4H_9$ | OH | OH | $CH_3$ | H |
| $C_2H_5$ | H | $n\text{-}C_5H_{11}$ | OH | OH | $CH_3$ | H |
| $C_2H_5$ | H | $n\text{-}C_6H_{13}$ | OH | OH | $CH_3$ | H |
| $C_2H_5$ | H | $C_2H_4OH$ | OH | OH | $CH_3$ | H |
| $C_2H_5$ | H | $-CH_2-CH(OH)-CH_3$ | OH | OH | $CH_3$ | H |
| $C_2H_5$ | H | $-CH_2-CH_2-CH_2OH$ | OH | OH | $CH_3$ | H |
| $C_2H_5$ | H | $-CH_2-CH_2-N(CH_3)_2$ | OH | OH | $CH_3$ | H |
| $C_2H_5$ | H | $-CH_2-CH_2-N(C_2H_5)_2$ | OH | OH | $CH_3$ | H |
| $C_2H_5$ | H | $-CH_2-CH_2-N(C_4H_9)_2$ | OH | OH | $CH_3$ | H |
| $C_2H_5$ | H | $-CH_2-CH_2-CH_2-N(CH_3)_2$ | OH | OH | $CH_3$ | H |
| $C_2H_5$ | H | $-CH_2-CH_2-CH_2-N(C_2H_5)_2$ | OH | OH | $CH_3$ | H |
| $C_2H_5$ | H | $-CH_2-CON(CH_3)_2$ | OH | OH | $CH_3$ | H |
| $C_2H_5$ | H | $-CH_2-CH_2-CON(CH_3)_2$ | OH | OH | $CH_3$ | H |
| $C_2H_5$ | H | $-CH_2-CON(C_2H_5)_2$ | OH | OH | $CH_3$ | H |
| $C_2H_5$ | H | $-CH_2-C_6H_5$ | OH | OH | $CH_3$ | H |
| $C_2H_5$ | H | $-CH_2-CH_2-C_6H_5$ | OH | OH | $CH_3$ | H |
| $C_2H_5$ | H | $-CH_2-CH_2-N\text{(pyrrolidinyl)}$ | OH | OH | $CH_3$ | H |
| $C_2H_5$ | H | $-CH_2-CH_2-N\text{(morpholinyl)}$ | OH | OH | $CH_3$ | H |
| $C_2H_5$ | H | $-CH_2-CH_2-N\text{(piperidinyl)}$ | OH | OH | $CH_3$ | H |
| $C_2H_5$ | H | $-CH_2-CH_2-N\text{(4-methylpiperazinyl)}$ | OH | OH | $CH_3$ | H |
| $C_2H_5$ | $n\text{-}C_5H_{11}$ | $n\text{-}C_5H_{11}$ | OH | OH | $CH_3$ | H |

Table IIB-continued

| $R_1, R_2$ | $R_3$ | $R_4$ | $R_5$ | $R_6$ | $R_7$ | $R_8$ |
|---|---|---|---|---|---|---|
| $C_2H_5$ | n-$C_6H_{13}$ | n-$C_6H_{13}$ | OH | OH | $CH_3$ | H |
| $C_2H_5$ | i-$C_3H_7$ | i-$C_3H_7$ | OH | OH | $CH_3$ | H |
| $C_2H_5$ | i-$C_4H_9$ | i-$C_4H_9$ | OH | OH | $CH_3$ | H |
| $C_2H_5$ | $C_2H_4OH$ | $C_2H_4OH$ | OH | OH | $CH_3$ | H |
| $C_2H_5$ | —CH$_2$—CH(OH)—CH$_3$ | —CH$_2$—CH(OH)—CH$_3$ | OH | OH | $CH_3$ | H |
| $C_2H_5$ | —CH$_3$ | $C_2H_4OH$ | OH | OH | $CH_3$ | H |
| $C_2H_5$ | —CH$_2$—CH$_2$—CH$_2$OH | —CH$_2$—CH$_2$—CH$_2$OH | OH | OH | $CH_3$ | H |
| $C_2H_5$ | —CH$_2$—$C_6H_5$ | —CH$_2$—$C_6H_5$ | OH | OH | $CH_3$ | H |
| $C_2H_5$ | —CH$_2$—CH$_2$—$C_6H_5$ | —CH$_2$—CH$_2$—$C_6H_5$ | OH | OH | $CH_3$ | H |
| $C_2H_5$ | H | cyclopentyl | OH | OH | $CH_3$ | H |
| $C_2H_5$ | H | cyclohexyl | OH | OH | $CH_3$ | H |
| $C_2H_5$ | H | cycloheptyl | OH | OH | $CH_3$ | H |
| $C_2H_5$ | | cyclohexyl-COOH | OH | OH | $CH_3$ | H |
| $C_2H_5$ | | cyclohexyl-CH$_2$-COOH | OH | OH | $CH_3$ | H |
| $C_2H_5$ | | cyclohexyl-CH$_2$-CH$_2$-COOH | OH | OH | $CH_3$ | H |
| $C_2H_5$ | | cyclopentyl-COOH | OH | OH | $CH_3$ | H |
| $C_2H_5$ | | cyclopentyl(COOH)(OH) | OH | OH | $CH_3$ | H |
| n-$C_3H_7$ | H | H | OH | OH | $CH_3$ | H |
| n-$C_3H_7$ | H | $CH_3$ | OH | OH | $CH_3$ | H |
| n-$C_3H_7$ | H | $C_2H_5$ | OH | OH | $CH_3$ | H |
| n-$C_3H_7$ | H | n-$C_3H_7$ | OH | OH | $CH_3$ | H |
| n-$C_3H_7$ | H | n-$C_4H_9$ | OH | OH | $CH_3$ | H |
| n-$C_3H_7$ | H | i-$C_3H_7$ | OH | OH | $CH_3$ | H |
| n-$C_3H_7$ | H | i-$C_4H_9$ | OH | OH | $CH_3$ | H |

Table IIB-continued

| R₁, R₂ | R₃ | R₄ | R₅ | R₆ | R₇ | R₈ |
|---|---|---|---|---|---|---|
| n-C₃H₇ | H | n-C₅H₁₁ | OH | OH | CH₃ | H |
| n-C₃H₇ | H | n-C₆H₁₃ | OH | OH | CH₃ | H |
| n-C₃H₇ | H | C₂H₄OH | OH | OH | CH₃ | H |
| n-C₃H₇ | H | —CH₂—CH(OH)—CH₃ | OH | OH | CH₃ | H |
| n-C₃H₇ | H | —CH₂—CH₂—CH₂OH | OH | OH | CH₃ | H |
| n-C₃H₇ | H | —CH₂—CH₂—N(CH₃)₂ | OH | OH | CH₃ | H |
| n-C₃H₇ | H | —CH₂—CH₂—N(C₂H₅)₂ | OH | OH | CH₃ | H |
| n-C₃H₇ | H | —CH₂—CH₂—N(C₄H₉)₂ | OH | OH | CH₃ | H |
| n-C₃H₇ | H | —CH₂—CH₂—CH₂—N(CH₃)₂ | OH | OH | CH₃ | H |
| n-C₃H₇ | H | —CH₂—CH₂—CH₂—N(C₂H₅)₂ | OH | OH | CH₃ | H |
| n-C₃H₇ | H | —CH₂—CON(CH₃)₂ | OH | OH | CH₃ | H |
| n-C₃H₇ | H | —CH₂—CH₂—CON(CH₃)₂ | OH | OH | CH₃ | H |
| n-C₃H₇ | H | —CH₂—CON(C₂H₅)₂ | OH | OH | CH₃ | H |
| n-C₃H₇ | H | —CH₂—C₆H₅ | OH | OH | CH₃ | H |
| n-C₃H₇ | H | —CH₂—CH₂—C₆H₅ | OH | OH | CH₃ | H |
| n-C₃H₇ | H | —CH₂—CH₂—N(pyrrolidinyl) | OH | OH | CH₃ | H |
| n-C₃H₇ | H | —CH₂—CH₂—N(morpholinyl) | OH | OH | CH₃ | H |
| n-C₃H₇ | H | —CH₂—CH₂—N(piperidinyl) | OH | OH | CH₃ | H |
| n-C₃H₇ | H | —CH₂—CH₂—N(4-methylpiperazinyl) | OH | OH | CH₃ | H |
| n-C₃H₇ | n-C₅H₁₁ | n-C₅H₁₁ | OH | OH | CH₃ | H |
| n-C₃H₇ | n-C₆H₁₃ | n-C₆H₁₃ | OH | OH | CH₃ | H |
| n-C₃H₇ | i-C₃H₇ | i-C₃H₇ | OH | OH | CH₃ | H |
| n-C₃H₇ | i-C₄H₉ | i-C₄H₉ | OH | OH | CH₃ | H |
| n-C₃H₇ | C₂H₄OH | C₂H₄OH | OH | OH | CH₃ | H |
| n-C₃H₇ | —CH₂—CH(OH)—CH₃ | —CH₂—CH(OH)—CH₃ | OH | OH | CH₃ | H |
| n-C₃H₇ | —CH₃ | C₂H₄OH | OH | OH | CH₃ | H |
| n-C₃H₇ | —CH₂—CH₂—CH₂OH | —CH₂—CH₂—CH₂OH | OH | OH | CH₃ | H |
| n-C₃H₇ | —CH₂—C₆H₅ | —CH₂—C₆H₅ | OH | OH | CH₃ | H |
| n-C₃H₇ | —CH₂—CH₂—C₆H₅ | —CH₂—CH₂—C₆H₅ | OH | OH | CH₃ | H |
| n-C₃H₇ | H | (cyclopentyl) | OH | OH | CH₃ | H |

… Table IIB-continued

| $R_1$, $R_2$ | $R_3$ | $R_4$ | $R_5$ | $R_6$ | $R_7$ | $R_8$ |
|---|---|---|---|---|---|---|
| n-$C_3H_7$ | H |  | OH | OH | $CH_3$ | H |
| n-$C_3H_7$ | H |  | OH | OH | $CH_3$ | H |
| n-$C_3H_7$ | H | 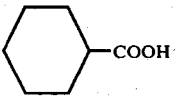 —COOH | OH | OH | $CH_3$ | H |
| n-$C_3H_7$ | H | —$CH_2$—COOH (cyclohexyl) | OH | OH | $CH_3$ | H |
| n-$C_3H_7$ | H | —$CH_2$—$CH_2$—COOH (cyclohexyl) | OH | OH | $CH_3$ | H |
| n-$C_3H_7$ | H | 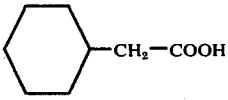 | OH | OH | $CH_3$ | H |
| n-$C_3H_7$ | H | 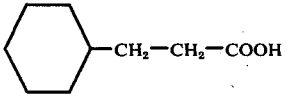 | OH | OH | $CH_3$ | H |
| n-$C_4H_9$ | H | H | OH | OH | $CH_3$ | H |
| n-$C_4H_9$ | H | $CH_3$ | OH | OH | $CH_3$ | H |
| n-$C_4H_9$ | H | $C_2H_5$ | OH | OH | $CH_3$ | H |
| n-$C_4H_9$ | H | n-$C_3H_7$ | OH | OH | $CH_3$ | H |
| n-$C_4H_9$ | H | n-$C_4H_9$ | OH | OH | $CH_3$ | H |
| n-$C_4H_9$ | H | i-$C_3H_7$ | OH | OH | $CH_3$ | H |
| n-$C_4H_9$ | H | i-$C_4H_9$ | OH | OH | $CH_3$ | H |
| n-$C_4H_9$ | H | n-$C_5H_{11}$ | OH | OH | $CH_3$ | H |
| n-$C_4H_9$ | H | n-$C_6H_{13}$ | OH | OH | $CH_3$ | H |
| n-$C_4H_9$ | H | $C_2H_4OH$ | OH | OH | $CH_3$ | H |
| n-$C_4H_9$ | H | —$CH_2$—CH(OH)—$CH_3$ | OH | OH | $CH_3$ | H |
| n-$C_4H_9$ | H | —$CH_2$—$CH_2$—$CH_2OH$ | OH | OH | $CH_3$ | H |
| n-$C_4H_9$ | H | —$CH_2$—$CH_2$—$N(CH_3)_2$ | OH | OH | $CH_3$ | H |
| n-$C_4H_9$ | H | —$CH_2$—$CH_2$—$N(C_2H_5)_2$ | OH | OH | $CH_3$ | H |
| n-$C_4H_9$ | H | —$CH_2$—$CH_2$—$N(C_4H_9)_2$ | OH | OH | $CH_3$ | H |
| n-$C_4H_9$ | H | —$CH_2$—$CH_2$—$CH_2$—$N(CH_3)_2$ | OH | OH | $CH_3$ | H |
| n-$C_4H_9$ | H | —$CH_2$—$CH_2$—$CH_2$—$N(C_2H_5)_2$ | OH | OH | $CH_3$ | H |
| n-$C_4H_9$ | H | —$CH_2$—$CON(CH_3)_2$ | OH | OH | $CH_3$ | H |
| n-$C_4H_9$ | H | —$CH_2$—$CH_2$—$CON(CH_3)_2$ | OH | OH | $CH_3$ | H |

Table IIB-continued

| R₁, R₂ | R₃ | R₄ | R₅ | R₆ | R₇ | R₈ |
|---|---|---|---|---|---|---|
| n-C₄H₉ | H | —CH₂—CON(C₂H₅)₂ | OH | OH | CH₃ | H |
| n-C₄H₉ | H | —CH₂—C₆H₅ | OH | OH | CH₃ | H |
| n-C₄H₉ | H | —CH₂—CH₂—C₆H₅ | OH | OH | CH₃ | H |
| n-C₄H₉ | H | —CH₂—CH₂—N<pyrrolidinyl> | OH | OH | CH₃ | H |
| n-C₄H₉ | H | —CH₂—CH₂—N(morpholino)O | H | OH | CH₃ | H |
| n-C₄H₉ | H | —CH₂—CH₂—N(piperidinyl) | OH | OH | CH₃ | H |
| n-C₄H₉ | H | —CH₂—CH₂—N(piperazinyl)N—CH₃ | OH | OH | CH₃ | H |
| n-C₄H₉ | n-C₅H₁₁ | n-C₅H₁₁ | OH | OH | CH₃ | H |
| n-C₄H₉ | n-C₆H₁₃ | n-C₆H₁₃ | OH | OH | CH₃ | H |
| n-C₄H₉ | i-C₃H₇ | i-C₃H₇ | OH | OH | CH₃ | H |
| n-C₄H₉ | i-C₄H₉ | i-C₄H₉ | OH | OH | CH₃ | H |
| n-C₄H₉ | C₂H₄OH | C₂H₄OH | OH | OH | CH₃ | H |
| n-C₄H₉ | —CH₂—CH(OH)—CH₃ | —CH₂—CH(OH)—CH₃ | OH | OH | CH₃ | H |
| n-C₄H₉ | —CH₃ | C₂H₄OH | OH | OH | CH₃ | H |
| n-C₄H₉ | —CH₂—CH₂—CH₂OH | —CH₂—CH₂—CH₂OH | OH | OH | CH₃ | H |
| n-C₄H₉ | —CH₂—C₆H₅ | —CH₂—C₆H₅ | OH | OH | CH₃ | H |
| n-C₄H₉ | —CH₂—CH₂—C₆H₅ | —CH₂—CH₂—C₆H₅ | OH | OH | CH₃ | H |
| n-C₄H₉ | H | cyclopentyl | OH | OH | CH₃ | H |
| n-C₄H₉ | H | cyclohexyl | OH | OH | CH₃ | H |
| n-C₄H₉ | H | cyclooctyl | OH | OH | CH₃ | H |
| n-C₄H₉ | \{cyclohexyl—COOH\} | | OH | OH | CH₃ | H |
| n-C₄H₉ | \{cyclohexyl—CH₂—COOH\} | | OH | OH | CH₃ | H |

Table IIB-continued

| $R_1, R_2$ | $R_3$ | $R_4$ | $R_5$ | $R_6$ | $R_7$ | $R_8$ |
|---|---|---|---|---|---|---|
| n-$C_4H_9$ | | cyclohexyl-$CH_2$-$CH_2$-COOH | OH | OH | $CH_3$ | H |
| n-$C_4H_9$ | | cyclopentyl-COOH | OH | OH | $CH_3$ | H |
| n-$C_4H_9$ | | cyclopentyl(COOH)(OH) | OH | OH | $CH_3$ | H |
| —$(CH_2)_2$— | H | H | OH | OH | $CH_3$ | H |
| —$(CH_2)_2$— | H | $CH_3$ | OH | OH | $CH_3$ | H |
| —$(CH_2)_2$— | H | $C_2H_5$ | OH | OH | $CH_3$ | H |
| —$(CH_2)_2$— | H | n-$C_3H_7$ | OH | OH | $CH_3$ | H |
| —$(CH_2)_2$— | H | n-$C_4H_9$ | OH | OH | $CH_3$ | H |
| —$(CH_2)_2$— | H | i-$C_3H_7$ | OH | OH | $CH_3$ | H |
| —$(CH_2)_2$— | H | i-$C_4H_9$ | OH | OH | $CH_3$ | H |
| —$(CH_2)_2$— | H | n-$C_5H_{11}$ | OH | OH | $CH_3$ | H |
| —$(CH_2)_2$— | H | n-$C_6H_{13}$ | OH | OH | $CH_3$ | H |
| —$(CH_2)_2$— | H | $C_2H_4OH$ | OH | OH | $CH_3$ | H |
| —$(CH_2)_2$— | H | —$CH_2$—CH(OH)—$CH_3$ | OH | OH | $CH_3$ | H |
| —$(CH_2)_2$— | H | —$CH_2$—$CH_2$—$CH_2OH$ | OH | OH | $CH_3$ | H |
| —$(CH_2)_2$— | H | —$CH_2$—$CH_2$—$N(CH_3)_2$ | OH | OH | $CH_3$ | H |
| —$(CH_2)_2$— | H | —$CH_2$—$CH_2$—$N(C_2H_5)_2$ | OH | OH | $CH_3$ | H |
| —$(CH_2)_2$— | H | —$CH_2$—$CH_2$—$N(C_4H_9)_2$ | OH | OH | $CH_3$ | H |
| —$(CH_2)_2$— | H | —$CH_2$—$CH_2$—$CH_2$—$N(CH_3)_2$ | OH | OH | $CH_3$ | H |
| —$(CH_2)_2$— | H | —$CH_2$—$CH_2$—$CH_2$—$N(C_2H_5)_2$ | OH | OH | $CH_3$ | H |
| —$(CH_2)_2$— | H | —$CH_2$—$CON(CH_3)_2$ | OH | OH | $CH_3$ | H |
| —$(CH_2)_2$— | H | —$CH_2$—$CH_2$—$CON(CH_3)_2$ | OH | OH | $CH_3$ | H |
| —$(CH_2)_2$— | H | —$CH_2$—$CON(C_2H_5)_2$ | OH | OH | $CH_3$ | H |
| —$(CH_2)_2$— | H | —$CH_2$—$C_6H_5$ | OH | OH | $CH_3$ | H |
| —$(CH_2)_2$— | H | —$CH_2$—$CH_2$—$C_6H_5$ | OH | OH | $CH_3$ | H |
| —$(CH_2)_2$— | H | —$CH_2$—$CH_2$—N(pyrrolidinyl) | OH | OH | $CH_3$ | H |
| —$(CH_2)_2$— | H | —$CH_2$—$CH_2$—N(morpholinyl) | OH | OH | $CH_3$ | H |
| —$(CH_2)_2$— | H | —$CH_2$—$CH_2$—N(piperidinyl) | OH | OH | $CH_3$ | H |
| —$(CH_2)_2$— | H | —$CH_2$—$CH_2$—N(4-methylpiperazinyl) | OH | OH | $CH_3$ | H |
| —$(CH_2)_2$— | n-$C_5H_{11}$ | n-$C_5H_{11}$ | OH | OH | $CH_3$ | H |
| —$(CH_2)_2$— | n-$C_6H_{13}$ | n-$C_6H_{13}$ | OH | OH | $CH_3$ | H |
| —$(CH_2)_2$— | i-$C_3H_7$ | i-$C_3H_7$ | OH | OH | $CH_3$ | H |

Table IIB-continued

| $R_1, R_2$ | $R_3$ | $R_4$ | $R_5$ | $R_6$ | $R_7$ | $R_8$ |
|---|---|---|---|---|---|---|
| $-(CH_2)_2-$ | $i-C_4H_9$ | $i-C_4H_9$ | OH | OH | $CH_3$ | H |
| $-(CH_2)_2-$ | $C_2H_4OH$ | $C_2H_4OH$ | OH | OH | $CH_3$ | H |
| $-(CH_2)_2-$ | $-CH_2-\underset{OH}{CH}-CH_3$ | $-CH_2-\underset{OH}{CH}-CH_3$ | OH | OH | $CH_3$ | H |
| $-(CH_2)_2-$ | $-CH_3$ | $C_2H_4OH$ | OH | OH | $CH_3$ | H |
| $-(CH_2)_2-$ | $-CH_2-CH_2-CH_2OH$ | $-CH_2-CH_2-CH_2OH$ | OH | OH | $CH_3$ | H |
| $-(CH_2)_2-$ | $-CH_2-C_6H_5$ | $-CH_2-C_6H_5$ | OH | OH | $CH_3$ | H |
| $-(CH_2)_2-$ | $-CH_2-CH_2-C_6H_5$ | $-CH_2-CH_2-C_6H_5$ | OH | OH | $CH_3$ | H |
| $-(CH_2)_2-$ | H |  | OH | OH | $CH_3$ | H |
| $-(CH_2)_2-$ | H |  | OH | OH | $CH_3$ | H |
| $-(CH_2)_2-$ | H |  | OH | OH | $CH_3$ | H |
| $-(CH_2)_2-$ |   | 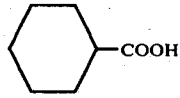 | OH | OH | $CH_3$ | H |
| $-(CH_2)_2-$ |   | 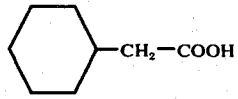 | OH | OH | $CH_3$ | H |
| $-(CH_2)_2-$ |   | 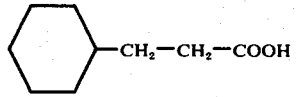 | OH | OH | $CH_3$ | H |
| $-(CH_2)_2-$ |   |  | OH | OH | $CH_3$ | H |
| $-(CH_2)_2-$ |   | 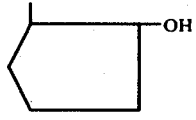 | OH | OH | $CH_3$ | H |
| $-(CH_2)_3-$ | H | H | OH | OH | $CH_3$ | H |
| $-(CH_2)_3-$ | H | $CH_3$ | OH | OH | $CH_3$ | H |
| $-(CH_2)_3-$ | H | $C_2H_5$ | OH | OH | $CH_3$ | H |
| $-(CH_2)_3-$ | H | $n-C_3H_7$ | OH | OH | $CH_3$ | H |
| $-(CH_2)_3-$ | H | $n-C_4H_9$ | OH | OH | $CH_3$ | H |
| $-(CH_2)_3-$ | H | $i-C_3H_7$ | OH | OH | $CH_3$ | H |
| $-(CH_2)_3-$ | H | $i-C_4H_9$ | OH | OH | $CH_3$ | H |
| $-(CH_2)_3-$ | H | $n-C_5H_{11}$ | OH | OH | $CH_3$ | H |

Table IIB-continued

| $R_1, R_2$ | $R_3$ | $R_4$ | $R_5$ | $R_6$ | $R_7$ | $R_8$ |
|---|---|---|---|---|---|---|
| $-(CH_2)_3-$ | H | n-$C_6H_{13}$ | OH | OH | $CH_3$ | H |
| $-(CH_2)_3-$ | H | $C_2H_4OH$ | OH | OH | $CH_3$ | H |
| $-(CH_2)_3-$ | H | $-CH_2-CH(OH)-CH_3$ | OH | OH | $CH_3$ | H |
| $-(CH_2)_3-$ | H | $-CH_2-CH_2-CH_2OH$ | OH | OH | $CH_3$ | H |
| $-(CH_2)_3-$ | H | $-CH_2-CH_2-N(CH_3)_2$ | OH | OH | $CH_3$ | H |
| $-(CH_2)_3-$ | H | $-CH_2-CH_2-N(C_2H_5)_2$ | OH | OH | $CH_3$ | H |
| $-(CH_2)_3-$ | H | $-CH_2-CH_2-N(C_4H_9)_2$ | OH | OH | $CH_3$ | H |
| $-(CH_2)_3-$ | H | $-CH_2-CH_2-CH_2-N(CH_3)_2$ | OH | OH | $CH_3$ | H |
| $-(CH_2)_3-$ | H | $-CH_2-CH_2-CH_2-N(C_2H_5)_2$ | OH | OH | $CH_3$ | H |
| $-(CH_2)_3-$ | H | $-CH_2-CON(CH_3)_2$ | OH | OH | $CH_3$ | H |
| $-(CH_2)_3-$ | H | $-CH_2-CH_2-CON(CH_3)_2$ | OH | OH | $CH_3$ | H |
| $-(CH_2)_3-$ | H | $-CH_2-CON(C_2H_5)_2$ | OH | OH | $CH_3$ | H |
| $-(CH_2)_3-$ | H | $-CH_2-C_6H_5$ | OH | OH | $CH_3$ | H |
| $-(CH_2)_3-$ | H | $-CH_2-CH_2-C_6H_5$ | OH | OH | $CH_3$ | H |
| $-(CH_2)_3-$ | H | $-CH_2-CH_2-N\text{(pyrrolidinyl)}$ | OH | OH | $CH_3$ | H |
| $-(CH_2)_3-$ | H | $-CH_2-CH_2-N\text{(morpholinyl)}$ | OH | OH | $CH_3$ | H |
| $-(CH_2)_3-$ | H | $-CH_2-CH_2-N\text{(piperidinyl)}$ | OH | OH | $CH_3$ | H |
| $-(CH_2)_3-$ | H | $-CH_2-CH_2-N\text{(4-methylpiperazinyl)}$ | OH | OH | $CH_3$ | H |
| $-(CH_2)_3-$ | n-$C_5H_{11}$ | n-$C_5H_{11}$ | OH | OH | $CH_3$ | H |
| $-(CH_2)_3-$ | n-$C_6H_{13}$ | n-$C_6H_{13}$ | OH | OH | $CH_3$ | H |
| $-(CH_2)_3-$ | i-$C_3H_7$ | i-$C_3H_7$ | OH | OH | $CH_3$ | H |
| $-(CH_2)_3-$ | i-$C_4H_9$ | i-$C_4H_9$ | OH | OH | $CH_3$ | H |
| $-(CH_2)_3-$ | $C_2H_4OH$ | $C_2H_4OH$ | OH | OH | $CH_3$ | H |
| $-(CH_2)_3-$ | $-CH_2-CH(OH)-CH_3$ | $-CH_2-CH(OH)-CH_3$ | OH | OH | $CH_3$ | H |
| $-(CH_2)_3-$ | $-CH_3$ | $C_2H_4OH$ | OH | OH | $CH_3$ | H |
| $-(CH_2)_3-$ | $-CH_2-CH_2-CH_2OH$ | $-CH_2-CH_2-CH_2OH$ | OH | OH | $CH_3$ | H |
| $-(CH_2)_3-$ | $-CH_2-C_6H_5$ | $-CH_2-C_6H_5$ | OH | OH | $CH_3$ | H |
| $-(CH_2)_3-$ | $-CH_2-CH_2-C_6H_5$ | $-CH_2-CH_2-C_6H_5$ | OH | OH | $CH_3$ | H |
| $-(CH_2)_3-$ | H | cyclopentyl | OH | OH | $CH_3$ | H |
| $-(CH_2)_3-$ | H | cyclohexyl | OH | OH | $CH_3$ | H |

Table IIB-continued

| $R_1, R_2$ | $R_3$ | $R_4$ | $R_5$ | $R_6$ | $R_7$ | $R_8$ |
|---|---|---|---|---|---|---|
| $-(CH_2)_3-$ | H | cycloheptyl | OH | OH | $CH_3$ | H |
| $-(CH_2)_3-$ | H | cyclohexyl-COOH | OH | OH | $CH_3$ | H |
| $-(CH_2)_3-$ | H | cyclohexyl-$CH_2$-COOH | OH | OH | $CH_3$ | H |
| $-(CH_2)_3-$ | H | cyclohexyl-$CH_2$-$CH_2$-COOH | OH | OH | $CH_3$ | H |
| $-(CH_2)_3-$ | H | cyclopentyl with COOH, COOH | OH | OH | $CH_3$ | H |
| $-(CH_2)_3-$ | H | cyclohexyl with OH | OH | OH | $CH_3$ | H |

Table IIIA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | H | OH | $CH_3$ | Cl |
| $CH_3$ | $CH_3$ | $C_2H_5$ | H | OH | $CH_3$ | Cl |
| $CH_3$ | $C_2H_5$ | $C_2H_5$ | H | OH | $CH_3$ | Cl |
| $CH_3$ | $n-C_3H_7$ | $n-C_3H_7$ | H | OH | $CH_3$ | Cl |
| $CH_3$ | $n-C_4H_9$ | $n-C_4H_9$ | H | OH | $CH_3$ | Cl |
| $CH_3$ | H | $CH_2-COOH$ | H | OH | $CH_3$ | Cl |
| $CH_3$ | H | $CH_2-COOC_2H_5$ | H | OH | $CH_3$ | Cl |
| $CH_3$ | H | $CH_3-CH-COOH$ | H | OH | $CH_3$ | Cl |
| $CH_3$ | H | $CH_3-CH-COOC_2H_5$ | H | OH | $CH_3$ | Cl |
| $CH_3$ | H | $-CH_2-CH_2-COOH$ | H | OH | $CH_3$ | Cl |
| $CH_3$ | H | $-CH_2-CH_2-COOC_2H_5$ | H | OH | $CH_3$ | Cl |
| $CH_3$ | H | $-(CH_2)_4-CH(NH_2)-COOH$ | H | OH | $CH_3$ | Cl |
| $CH_3$ | \multicolumn{2}{c}{cyclopentyl} | H | OH | $CH_3$ | Cl |

Table IIIA-continued

| $R_1, R_2$ | $R_3$ | $R_4$ | $R_5$ | $R_6$ | $R_7$ | $R_8$ |
|---|---|---|---|---|---|---|
| $CH_3$ |  | | H | OH | $CH_3$ | Cl |
| $CH_3$ |  | | H | OH | $CH_3$ | Cl |
| $CH_3$ |  | | H | OH | $CH_3$ | Cl |
| $CH_3$ | 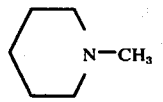 | | H | OH | $CH_3$ | Cl |
| $CH_3$ | 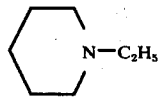 | | H | OH | $CH_3$ | Cl |
| $CH_3$ | 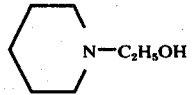 | | H | OH | $CH_3$ | Cl |
| $C_2H_5$ | $CH_3$ | $CH_3$ | H | OH | $CH_3$ | Cl |
| $C_2H_5$ | $CH_3$ | $C_2H_5$ | H | OH | $CH_3$ | Cl |
| $C_2H_5$ | $C_2H_5$ | $C_2H_5$ | H | OH | $CH_3$ | Cl |
| $C_2H_5$ | n-$C_3H_7$ | n-$C_3H_7$ | H | OH | $CH_3$ | Cl |
| $C_2H_5$ | n-$C_4H_9$ | n-$C_4H_9$ | H | OH | $CH_3$ | Cl |
| $C_2H_5$ | H | $CH_2$—COOH | H | OH | $CH_3$ | Cl |
| $C_2H_5$ | H | $CH_2$—$COOC_2H_5$ | H | OH | $CH_3$ | Cl |
| $C_2H_5$ | H | $CH_3$—CH—COOH<br>\|  | H | OH | $CH_3$ | Cl |
| $C_2H_5$ | H | $CH_3$—CH—$COOC_2H_5$<br>\| | H | OH | $CH_3$ | Cl |
| $C_2H_5$ | H | —$CH_2$—$CH_2$—COOH | H | OH | $CH_3$ | Cl |
| $C_2H_5$ | H | —$CH_2$—$CH_2$—$COOC_2H_5$ | H | OH | $CH_3$ | Cl |
| $C_2H_5$ | H | —$(CH_2)_4$—CH—COOH<br>\|<br>$NH_2$ | H | OH | $CH_3$ | Cl |
| $C_2H_5$ |  | | H | OH | $CH_3$ | Cl |
| $C_2H_5$ |  | | H | OH | $CH_3$ | Cl |
| $C_2H_5$ |  | | H | OH | $CH_3$ | Cl |

Table IIIA-continued

| $R_1, R_2$ | $R_3$ | $R_4$ | $R_5$ | $R_6$ | $R_7$ | $R_8$ |
|---|---|---|---|---|---|---|
| $C_2H_5$ | | piperidino | H | OH | $CH_3$ | Cl |
| $C_2H_5$ | | 4-methylpiperazino (N—$CH_3$) | H | OH | $CH_3$ | Cl |
| $C_2H_5$ | | 4-ethylpiperazino (N—$C_2H_5$) | H | OH | $CH_3$ | Cl |
| $C_2H_5$ | | 4-(2-hydroxyethyl)piperazino (N—$C_2H_5OH$) | H | OH | $CH_3$ | Cl |
| n-$C_3H_7$ | $CH_3$ | $CH_3$ | H | OH | $CH_3$ | Cl |
| n-$C_3H_7$ | $CH_3$ | $C_2H_5$ | H | OH | $CH_3$ | Cl |
| n-$C_3H_7$ | $C_2H_5$ | $C_2H_5$ | H | OH | $CH_3$ | Cl |
| n-$C_3H_7$ | n-$C_3H_7$ | n-$C_3H_7$ | H | OH | $CH_3$ | Cl |
| n-$C_3H_7$ | n-$C_4H_9$ | n-$C_4H_9$ | H | OH | $CH_3$ | Cl |
| n-$C_3H_7$ | H | $CH_2$—COOH | H | OH | $CH_3$ | Cl |
| n-$C_3H_7$ | H | $CH_2$—$COOC_2H_5$ | H | OH | $CH_3$ | Cl |
| n-$C_3H_7$ | H | $CH_3$—CH—COOH | H | OH | $CH_3$ | Cl |
| n-$C_3H_7$ | H | $CH_3$—CH—$COOC_2H_5$ | H | OH | $CH_3$ | Cl |
| n-$C_3H_7$ | H | —$CH_2$—$CH_2$—COOH | H | OH | $CH_3$ | Cl |
| n-$C_3H_7$ | H | —$CH_2$—$CH_2$—$COOC_2H_5$ | H | OH | $CH_3$ | Cl |
| n-$C_3H_7$ | H | —$(CH_2)_4$—CH(—$NH_2$)—COOH | H | OH | $CH_3$ | Cl |
| n-$C_3H_7$ | \{ pyrrolidino \} | | H | OH | $CH_3$ | Cl |
| n-$C_3H_7$ | \{ piperidino \} | | H | OH | $CH_3$ | Cl |
| n-$C_3H_7$ | \{ morpholino (O) \} | | H | OH | $CH_3$ | Cl |
| n-$C_3H_7$ | \{ piperazino (N) \} | | H | OH | $CH_3$ | Cl |
| n-$C_3H_7$ | \{ 4-methylpiperazino (N—$CH_3$) \} | | H | OH | $CH_3$ | Cl |

Table IIIA-continued

| R₁, R₂ | R₃ | R₄ | R₅ | R₆ | R₇ | R₈ |
|---|---|---|---|---|---|---|
| n-C₃H₇ | | ⬡N—C₂H₅ | H | OH | CH₃ | Cl |
| n-C₃H₇ | | ⬡N—C₂H₅OH | H | OH | CH₃ | Cl |
| n-C₄H₉ | CH₃ | CH₃ | H | OH | CH₃ | Cl |
| n-C₄H₉ | CH₃ | C₂H₅ | H | OH | CH₃ | Cl |
| n-C₄H₉ | C₂H₅ | C₂H₅ | H | OH | CH₃ | Cl |
| n-C₄H₉ | n-C₃H₇ | n-C₃H₇ | H | OH | CH₃ | Cl |
| n-C₄H₉ | n-C₄H₉ | n-C₄H₉ | H | OH | CH₃ | Cl |
| n-C₄H₉ | H | CH₂—COOH | H | OH | CH₃ | Cl |
| n-C₄H₉ | H | CH₂—COOC₂H₅ | H | OH | CH₃ | Cl |
| n-C₄H₉ | H | CH₃—CH—COOH | H | OH | CH₃ | Cl |
| n-C₄H₉ | H | CH₃—CH—COOC₂H₅ | H | OH | CH₃ | Cl |
| n-C₄H₉ | H | —CH₂—CH₂—COOH | H | OH | CH₃ | Cl |
| n-C₄H₉ | H | —CH₂—CH₂—COOC₂H₅ | H | OH | CH₃ | Cl |
| n-C₄H₉ | H | —(CH₂)₄—CH(NH₂)—COOH | H | OH | CH₃ | Cl |
| n-C₄H₉ | | ⬠ (cyclopentyl) | H | OH | CH₃ | Cl |
| n-C₄H₉ | | ⬡ (cyclohexyl) | H | OH | CH₃ | Cl |
| n-C₄H₉ | | ⬡O | H | OH | CH₃ | Cl |
| n-C₄H₉ | | ⬡N | H | OH | CH₃ | Cl |
| n-C₄H₉ | | ⬡N—CH₃ | H | OH | CH₃ | Cl |
| n-C₄H₉ | | ⬡N—C₂H₅ | H | OH | CH₃ | Cl |
| n-C₄H₉ | | ⬡N—C₂H₅OH | H | OH | CH₃ | Cl |

TABLE IIIB

| $R_1, R_2$ | $R_3$ | $R_4$ | $R_5$ | $R_6$ | $R_7$ | $R_8$ |
|---|---|---|---|---|---|---|
| $CH_3$ | H | H | H | OH | $CH_3$ | Cl |
| $CH_3$ | H | $CH_3$ | H | OH | $CH_3$ | Cl |
| $CH_3$ | H | $C_2H_5$ | H | OH | $CH_3$ | Cl |
| $CH_3$ | H | n-$C_3H_7$ | H | OH | $CH_3$ | Cl |
| $CH_3$ | H | n-$C_4H_9$ | H | OH | $CH_3$ | Cl |
| $CH_3$ | H | i-$C_3H_7$ | H | OH | $CH_3$ | Cl |
| $CH_3$ | H | i-$C_4H_9$ | H | OH | $CH_3$ | Cl |
| $CH_3$ | H | n-$C_5H_{11}$ | H | OH | $CH_3$ | Cl |
| $CH_3$ | H | n-$C_6H_{13}$ | H | OH | $CH_3$ | Cl |
| $CH_3$ | H | $C_2H_4OH$ | H | OH | $CH_3$ | Cl |
| $CH_3$ | H | $-CH_2-CH(OH)-CH_3$ | H | OH | $CH_3$ | Cl |
| $CH_3$ | H | $-CH_2-CH_2-CH_2OH$ | H | OH | $CH_3$ | Cl |
| $CH_3$ | H | $-CH_2-CH_2-N(CH_3)_2$ | H | OH | $CH_3$ | Cl |
| $CH_3$ | H | $-CH_2-CH_2-N(C_2H_5)_2$ | H | OH | $CH_3$ | Cl |
| $CH_3$ | H | $-CH_2-CH_2-N(C_4H_9)_2$ | H | OH | $CH_3$ | Cl |
| $CH_3$ | H | $-CH_2-CH_2-CH_2-N(CH_3)_2$ | H | OH | $CH_3$ | Cl |
| $CH_3$ | H | $-CH_2-CH_2-CH_2-N(C_2H_5)_2$ | H | OH | $CH_3$ | Cl |
| $CH_3$ | H | $-CH_2-CON(CH_3)_2$ | H | OH | $CH_3$ | Cl |
| $CH_3$ | H | $-CH_2-CH_2-CON(CH_3)_2$ | H | OH | $CH_3$ | Cl |
| $CH_3$ | H | $-CH_2-CON(C_2H_5)_2$ | H | OH | $CH_3$ | Cl |
| $CH_3$ | H | $-CH_2-C_6H_5$ | H | OH | $CH_3$ | Cl |
| $CH_3$ | H | $-CH_2-CH_2-C_6H_5$ | H | OH | $CH_3$ | Cl |
| $CH_3$ | H | $-CH_2-CH_2-$N(pyrrolidinyl) | H | OH | $CH_3$ | Cl |
| $CH_3$ | H | $-CH_2-CH_2-$N(morpholinyl) | H | OH | $CH_3$ | Cl |
| $CH_3$ | H | $-CH_2-CH_2-$N(piperidinyl) | H | OH | $CH_3$ | Cl |
| $CH_3$ | H | $-CH_2-CH_2-$N(4-methylpiperazinyl) | H | OH | $CH_3$ | Cl |
| $CH_3$ | n-$C_5H_{11}$ | n-$C_5H_{11}$ | H | OH | $CH_3$ | Cl |
| $CH_3$ | n-$C_6H_{13}$ | n-$C_6H_{13}$ | H | OH | $CH_3$ | Cl |
| $CH_3$ | i-$C_3H_7$ | i-$C_3H_7$ | H | OH | $CH_3$ | Cl |
| $CH_3$ | i-$C_4H_9$ | i-$C_4H_9$ | H | OH | $CH_3$ | Cl |
| $CH_3$ | $C_2H_4OH$ | $C_2H_4OH$ | H | OH | $CH_3$ | Cl |
| $CH_3$ | $-CH_2-CH(OH)-CH_3$ | $-CH_2-CH(OH)-CH_3$ | H | OH | $CH_3$ | Cl |
| $CH_3$ | $-CH_3$ | $C_2H_4OH$ | H | OH | $CH_3$ | Cl |
| $CH_3$ | $-CH_2-CH_2-CH_2OH$ | $-CH_2-CH_2-CH_2OH$ | H | OH | $CH_3$ | Cl |

TABLE IIIB-continued

| $R_1, R_2$ | $R_3$ | $R_4$ | $R_5$ | $R_6$ | $R_7$ | $R_8$ |
|---|---|---|---|---|---|---|
| $CH_3$ | $-CH_2-C_6H_5$ | $-CH_2-C_6H_5$ | H | OH | $CH_3$ | Cl |
| $CH_3$ | $-CH_2-CH_2-C_6H_5$ | $-CH_2-CH_2-C_6H_5$ | H | OH | $CH_3$ | Cl |
| $CH_3$ | H |  | H | OH | $CH_3$ | Cl |
| $CH_3$ | H |  | H | OH | $CH_3$ | Cl |
| $CH_3$ | H |  | H | OH | $CH_3$ | Cl |
| $CH_3$ | | 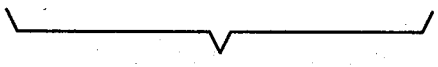 | H | OH | $CH_3$ | Cl |
| $CH_3$ | | 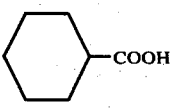 | H | OH | $CH_3$ | Cl |
| $CH_3$ | | 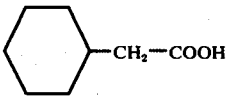 | H | OH | $CH_3$ | Cl |
| $CH_3$ | 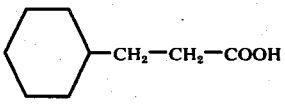 | | H | OH | $CH_3$ | Cl |
| $CH_3$ |  | | H | OH | $CH_3$ | Cl |
| $C_2H_5$ | H | H | H | OH | $CH_3$ | Cl |
| $C_2H_5$ | H | $CH_3$ | H | OH | $CH_3$ | Cl |
| $C_2H_5$ | H | $C_2H_5$ | H | OH | $CH_3$ | Cl |
| $C_2H_5$ | H | $n-C_3H_7$ | H | OH | $CH_3$ | Cl |
| $C_2H_5$ | H | $n-C_4H_9$ | H | OH | $CH_3$ | Cl |
| $C_2H_5$ | H | $i-C_3H_7$ | H | OH | $CH_3$ | Cl |
| $C_2H_5$ | H | $i-C_4H_9$ | H | OH | $CH_3$ | Cl |
| $C_2H_5$ | H | $n-C_5H_{11}$ | H | OH | $CH_3$ | Cl |
| $C_2H_5$ | H | $n-C_6H_{13}$ | H | OH | $CH_3$ | Cl |
| $C_2H_5$ | H | $C_2H_4OH$ | H | OH | $CH_3$ | Cl |
| $C_2H_5$ | H | 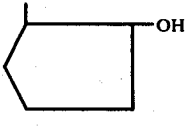 | H | OH | $CH_3$ | Cl |
| $C_2H_5$ | H | $-CH_2-CH_2-CH_2OH$ | H | OH | $CH_3$ | Cl |
| $C_2H_5$ | H | $-CH_2-CH_2-N(CH_3)_2$ | H | OH | $CH_3$ | Cl |
| $C_2H_5$ | H | $-CH_2-CH_2-N(C_2H_5)_2$ | H | OH | $CH_3$ | Cl |

TABLE IIIB-continued

| R₁, R₂ | R₃ | R₄ | R₅ | R₆ | R₇ | R₈ |
|---|---|---|---|---|---|---|
| C₂H₅ | H | —CH₂—CH₂—N(C₄H₉)₂ | H | OH | CH₃ | Cl |
| C₂H₅ | H | —CH₂—CH₂—CH₂—N(CH₃)₂ | H | OH | CH₃ | Cl |
| C₂H₅ | H | —CH₂—CH₂—CH₂—N(C₂H₅)₂ | H | OH | CH₃ | Cl |
| C₂H₅ | H | —CH₂—CON(CH₃)₂ | H | OH | CH₃ | Cl |
| C₂H₅ | H | —CH₂—CH₂—CON(CH₃)₂ | H | OH | CH₃ | Cl |
| C₂H₅ | H | —CH₂—CON(C₂H₅)₂ | H | OH | CH₃ | Cl |
| C₂H₅ | H | —CH₂—C₆H₅ | H | OH | CH₃ | Cl |
| C₂H₅ | H | —CH₂—CH₂—C₆H₅ | H | OH | CH₃ | Cl |
| C₂H₅ | H | —CH₂—CH₂—N(pyrrolidinyl) | H | OH | CH₃ | Cl |
| C₂H₅ | H | —CH₂—CH₂—N(morpholinyl) | H | OH | CH₃ | Cl |
| C₂H₅ | H | —CH₂—CH₂—N(piperidinyl) | H | OH | CH₃ | Cl |
| C₂H₅ | H | —CH₂—CH₂—N(N'-methylpiperazinyl) | H | OH | CH₃ | Cl |
| C₂H₅ | n-C₅H₁₁ | n-C₅H₁₁ | H | OH | CH₃ | Cl |
| C₂H₅ | n-C₆H₁₃ | n-C₆H₁₃ | H | OH | CH₃ | Cl |
| C₂H₅ | i-C₃H₇ | i-C₃H₇ | H | OH | CH₃ | Cl |
| C₂H₅ | i-C₄H₉ | i-C₄H₉ | H | OH | CH₃ | Cl |
| C₂H₅ | C₂H₄OH | C₂H₄OH | H | OH | CH₃ | Cl |
| C₂H₅ | —CH₂—CH(OH)—CH₃ | —CH₂—CH(OH)—CH₃ | H | OH | CH₃ | Cl |
| C₂H₅ | —CH₃ | C₂H₄OH | H | OH | CH₃ | Cl |
| C₂H₅ | —CH₂—CH₂—CH₂OH | —CH₂—CH₂—CH₂OH | H | OH | CH₃ | Cl |
| C₂H₅ | —CH₂—C₆H₅ | —CH₂—C₆H₅ | H | OH | CH₃ | Cl |
| C₂H₅ | —CH₂—CH₂—C₆H₅ | —CH₂—CH₂—C₆H₅ | H | OH | CH₃ | Cl |
| C₂H₅ | H | cyclopentyl | H | OH | CH₃ | Cl |
| C₂H₅ | H | cyclohexyl | H | OH | CH₃ | Cl |
| C₂H₅ | H | cycloheptyl | H | OH | CH₃ | Cl |

TABLE IIIB-continued

| R₁, R₂ | R₃ | R₄ | R₅ | R₆ | R₇ | R₈ |
|---|---|---|---|---|---|---|
| $C_2H_5$ | | cyclohexyl–COOH | H | OH | $CH_3$ | Cl |
| $C_2H_5$ | | cyclohexyl–$CH_2$–COOH | H | OH | $CH_3$ | Cl |
| $C_2H_5$ | | cyclohexyl–$CH_2$–$CH_2$–COOH | H | OH | $CH_3$ | Cl |
| $C_2H_5$ | | cyclopentyl–COOH | H | OH | $CH_3$ | Cl |
| $C_2H_5$ | | cyclopentyl(COOH)(OH) | H | OH | $CH_3$ | Cl |
| $n\text{-}C_3H_7$ | H | H | H | OH | $CH_3$ | Cl |
| $n\text{-}C_3H_7$ | H | $CH_3$ | H | OH | $CH_3$ | Cl |
| $n\text{-}C_3H_7$ | H | $C_2H_5$ | H | OH | $CH_3$ | Cl |
| $n\text{-}C_3H_7$ | H | $n\text{-}C_3H_7$ | H | OH | $CH_3$ | Cl |
| $n\text{-}C_3H_7$ | H | $n\text{-}C_4H_9$ | H | OH | $CH_3$ | Cl |
| $n\text{-}C_3H_7$ | H | $i\text{-}C_3H_7$ | H | OH | $CH_3$ | Cl |
| $n\text{-}C_3H_7$ | H | $i\text{-}C_4H_9$ | H | OH | $CH_3$ | Cl |
| $n\text{-}C_3H_7$ | H | $n\text{-}C_5H_{11}$ | H | OH | $CH_3$ | Cl |
| $n\text{-}C_3H_7$ | H | $n\text{-}C_6H_{13}$ | H | OH | $CH_3$ | Cl |
| $n\text{-}C_3H_7$ | H | $C_2H_4OH$ | H | OH | $CH_3$ | Cl |
| $n\text{-}C_3H_7$ | H | $-CH_2-CH(OH)-CH_3$ | H | OH | $CH_3$ | Cl |
| $n\text{-}C_3H_7$ | H | $-CH_2-CH_2-CH_2OH$ | H | OH | $CH_3$ | Cl |
| $n\text{-}C_3H_7$ | H | $-CH_2-CH_2-N(CH_3)_2$ | H | OH | $CH_3$ | Cl |
| $n\text{-}C_3H_7$ | H | $-CH_2-CH_2-N(C_2H_5)_2$ | H | OH | $CH_3$ | Cl |
| $n\text{-}C_3H_7$ | H | $-CH_2-CH_2-N(C_4H_9)_2$ | H | OH | $CH_3$ | Cl |
| $n\text{-}C_3H_7$ | H | $-CH_2-CH_2-CH_2-N(CH_3)_2$ | H | OH | $CH_3$ | Cl |
| $n\text{-}C_3H_7$ | H | $-CH_2-CH_2-CH_2-N(C_2H_5)_2$ | H | OH | $CH_3$ | Cl |
| $n\text{-}C_3H_7$ | H | $-CH_2-CON(CH_3)_2$ | H | OH | $CH_3$ | Cl |
| $n\text{-}C_3H_7$ | H | $-CH_2-CH_2-CON(CH_3)_2$ | H | OH | $CH_3$ | Cl |
| $n\text{-}C_3H_7$ | H | $-CH_2-CON(C_2H_5)_2$ | H | OH | $CH_3$ | Cl |
| $n\text{-}C_3H_7$ | H | $-CH_2-C_6H_5$ | H | OH | $CH_3$ | Cl |
| $n\text{-}C_3H_7$ | H | $-CH_2-CH_2-C_6H_5$ | H | OH | $CH_3$ | Cl |
| $n\text{-}C_3H_7$ | H | $-CH_2-CH_2-N\text{(pyrrolidinyl)}$ | H | OH | $CH_3$ | Cl |

TABLE IIIB-continued

| R₁, R₂ | R₃ | R₄ | R₅ | R₆ | R₇ | R₈ |
|---|---|---|---|---|---|---|
| n-C₃H₇ | H | —CH₂—CH₂—N(morpholino) | H | OH | CH₃ | Cl |
| n-C₃H₇ | H | —CH₂—CH₂—N(piperidino) | H | OH | CH₃ | Cl |
| n-C₃H₇ | H | —CH₂—CH₂—N(N'-methylpiperazino) | H | OH | CH₃ | Cl |
| n-C₃H₇ | n-C₅H₁₁ | n-C₅H₁₁ | H | OH | CH₃ | Cl |
| n-C₃H₇ | n-C₆H₁₃ | N-C₆H₁₃ | H | OH | CH₃ | Cl |
| n-C₃H₇ | i-C₃H₇ | i-C₃H₇ | H | OH | CH₃ | Cl |
| n-C₃H₇ | i-C₄H₉ | i-C₄H₉ | H | OH | CH₃ | Cl |
| n-C₃H₇ | C₂H₄OH | C₂H₄OH | H | OH | CH₃ | Cl |
| n-C₃H₇ | —CH₂—CH(OH)—CH₃ | —CH₂—CH(OH)—CH₃ | H | OH | CH₃ | Cl |
| n-C₃H₇ | —CH₃ | C₂H₄OH | H | OH | CH₃ | Cl |
| n-C₃H₇ | —CH₂—CH₂—CH₂OH | —CH₂—CH₂—CH₂OH | H | OH | CH₃ | Cl |
| n-C₃H₇ | —CH₂—C₆H₅ | —CH₂—C₆H₅ | H | OH | CH₃ | Cl |
| n-C₃H₇ | —CH₂—CH₂—C₆H₅ | —CH₂—CH₂—C₆H₅ | H | OH | CH₃ | Cl |
| n-C₃H₇ | H | cyclopentyl | H | OH | CH₃ | Cl |
| n-C₃H₇ | H | cyclohexyl | H | OH | CH₃ | Cl |
| n-C₃H₇ | H | cyclooctyl | H | OH | CH₃ | Cl |
| n-C₃H₇ | | cyclohexyl—COOH | H | OH | CH₃ | Cl |
| n-C₃H₇ | | cyclohexyl—CH₂—COOH | H | OH | CH₃ | Cl |
| n-C₃H₇ | | cyclohexyl—CH₂—CH₂—COOH | H | OH | CH₃ | Cl |
| n-C₃H₇ | | cyclopentyl—COOH | H | OH | CH₃ | Cl |

TABLE IIIB-continued

| $R_1, R_2$ | $R_3$ | $R_4$ | $R_5$ | $R_6$ | $R_7$ | $R_8$ |
|---|---|---|---|---|---|---|
| n-$C_3H_7$ | | 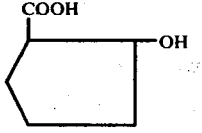 COOH, OH (cyclohexane) | H | OH | $CH_3$ | Cl |
| n-$C_4H_9$ | H | H | H | OH | $CH_3$ | Cl |
| n-$C_4H_9$ | H | $CH_3$ | H | OH | $CH_3$ | Cl |
| n-$C_4H_9$ | H | $C_2H_5$ | H | OH | $CH_3$ | Cl |
| n-$C_4H_9$ | H | n-$C_3H_7$ | H | OH | $CH_3$ | Cl |
| n-$C_4H_9$ | H | n-$C_4H_9$ | H | OH | $CH_3$ | Cl |
| n-$C_4H_9$ | H | i-$C_3H_7$ | H | OH | $CH_3$ | Cl |
| n-$C_4H_9$ | H | i-$C_4H_9$ | H | OH | $CH_3$ | Cl |
| n-$C_4H_9$ | H | n-$C_5H_{11}$ | H | OH | $CH_3$ | Cl |
| n-$C_4H_9$ | H | n-$C_6H_{13}$ | H | OH | $CH_3$ | Cl |
| n-$C_4H_9$ | H | $C_2H_4OH$ | H | OH | $CH_3$ | Cl |
| n-$C_4H_9$ | H | $-CH_2-CH(OH)-CH_3$ | H | OH | $CH_3$ | Cl |
| n-$C_4H_9$ | H | $-CH_2-CH_2-CH_2OH$ | H | OH | $CH_3$ | Cl |
| n-$C_4H_9$ | H | $-CH_2-CH_2-N(CH_3)_2$ | H | OH | $CH_3$ | Cl |
| n-$C_4H_9$ | H | $-CH_2-CH_2-N(C_2H_5)_2$ | H | OH | $CH_3$ | Cl |
| n-$C_4H_9$ | H | $-CH_2-CH_2-N(C_4H_9)_2$ | H | OH | $CH_3$ | Cl |
| n-$C_4H_9$ | H | $-CH_2-CH_2-CH_2-N(CH_3)_2$ | H | OH | $CH_3$ | Cl |
| n-$C_4H_9$ | H | $-CH_2-CH_2-CH_2-N(C_2H_5)_2$ | H | OH | $CH_3$ | Cl |
| n-$C_4H_9$ | H | $-CH_2-CON(CH_3)_2$ | H | OH | $CH_3$ | Cl |
| n-$C_4H_9$ | H | $-CH_2-CH_2-CON(CH_3)_2$ | H | OH | $CH_3$ | Cl |
| n-$C_4H_9$ | H | $-CH_2-CON(C_2H_5)_2$ | H | OH | $CH_3$ | Cl |
| n-$C_4H_9$ | H | $-CH_2-C_6H_5$ | H | OH | $CH_3$ | Cl |
| n-$C_4H_9$ | H | $-CH_2-CH_2-C_6H_5$ | H | OH | $CH_3$ | Cl |
| n-$C_4H_9$ | H | $-CH_2-CH_2-N$ 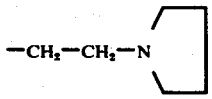 (pyrrolidine) | H | OH | $CH_3$ | Cl |
| n-$C_4H_9$ | H | $-CH_2-CH_2-N$ 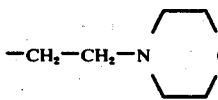 O (morpholine) | H | OH | $CH_3$ | Cl |
| n-$C_4H_9$ | H | $-CH_2-CH_2-N$ 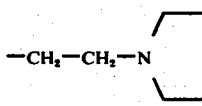 (piperidine) | H | OH | $CH_3$ | Cl |
| n-$C_4H_9$ | H | $-CH_2-CH_2-N$ 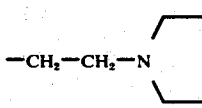 (piperidine) | H | OH | $CH_3$ | Cl |
| n-$C_4H_9$ | n-$C_5H_{11}$ | n-$C_5H_{11}$ | H | OH | $CH_3$ | Cl |
| n-$C_4H_9$ | n-$C_6H_{13}$ | n-$C_6H_{13}$ | H | OH | $CH_3$ | Cl |
| n-$C_4H_9$ | i-$C_3H_7$ | i-$C_3H_7$ | H | OH | $CH_3$ | Cl |
| n-$C_4H_9$ | i-$C_4H_9$ | i-$C_4H_9$ | H | OH | $CH_3$ | Cl |
| n-$C_4H_9$ | $C_2H_4OH$ | $C_2H_4OH$ | H | OH | $CH_3$ | Cl |

TABLE IIIB-continued

| $R_1, R_2$ | $R_3$ | $R_4$ | $R_5$ | $R_6$ | $R_7$ | $R_8$ |
|---|---|---|---|---|---|---|
| n-$C_4H_9$ | —$CH_2$—CH(OH)—$CH_3$ | —$CH_2$—CH(OH)—$CH_3$ | H | OH | $CH_3$ | Cl |
| n-$C_4H_9$ | —$CH_3$ | $C_2H_4OH$ | H | OH | $CH_3$ | Cl |
| n-$C_4H_9$ | —$CH_2$—$CH_2$—$CH_2OH$ | —$CH_2$—$CH_2$—$CH_2OH$ | H | OH | $CH_3$ | Cl |
| n-$C_4H_9$ | —$CH_2$—$C_6H_5$ | —$CH_2$—$C_6H_5$ | H | OH | $CH_3$ | Cl |
| n-$C_4H_9$ | —$CH_2$—$CH_2$—$C_6H_5$ | —$CH_2$—$CH_2$—$C_6H_5$ | H | OH | $CH_3$ | Cl |
| n-$C_4H_9$ | H |  (cyclopentyl) | H | OH | $CH_3$ | Cl |
| n-$C_4H_9$ | H |  (cyclohexyl) | H | OH | $CH_3$ | Cl |
| n-$C_4H_9$ | H |  (cycloheptyl) | H | OH | $CH_3$ | Cl |
| n-$C_4H_9$ | 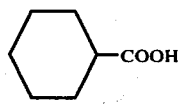 cyclohexyl-COOH | | H | OH | $CH_3$ | Cl |
| n-$C_4H_9$ | cyclohexyl-$CH_2$—COOH | | H | OH | $CH_3$ | Cl |
| n-$C_4H_9$ | cyclohexyl-$CH_2$—$CH_2$—COOH | | H | OH | $CH_3$ | Cl |
| n-$C_4H_9$ | 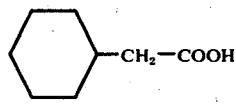 cyclopentyl-COOH | | H | OH | $CH_3$ | Cl |
| n-$C_4H_9$ | 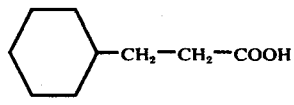 2-hydroxycyclohexyl-COOH | | H | OH | $CH_3$ | Cl |
| —$(CH_2)_2$— | H | H | H | OH | $CH_3$ | Cl |
| —$(CH_2)_2$— | H | $CH_3$ | H | OH | $CH_3$ | Cl |
| —$(CH_2)_2$— | H | $C_2H_5$ | H | OH | $CH_3$ | Cl |
| —$(CH_2)_2$— | H | n-$C_3H_7$ | H | OH | $CH_3$ | Cl |
| —$(CH_2)_2$— | H | n-$C_4H_9$ | H | OH | $CH_3$ | Cl |
| —$(CH_2)_2$— | H | i-$C_3H_7$ | H | OH | $CH_3$ | Cl |
| —$(CH_2)_2$— | H | i-$C_4H_9$ | H | OH | $CH_3$ | Cl |
| —$(CH_2)_2$— | H | n-$C_5H_{11}$ | H | OH | $CH_3$ | Cl |
| —$(CH_2)_2$— | H | n-$C_6H_{13}$ | H | OH | $CH_3$ | Cl |
| —$(CH_2)_2$— | H | $C_2H_4OH$ | H | OH | $CH_3$ | Cl |

TABLE IIIB-continued

| $R_1, R_2$ | $R_3$ | $R_4$ | $R_5$ | $R_6$ | $R_7$ | $R_8$ |
|---|---|---|---|---|---|---|
| $-(CH_2)_2-$ | H | $-CH_2-CH(OH)-CH_3$ | H | OH | $CH_3$ | Cl |
| $-(CH_2)_2-$ | H | $-CH_2-CH_2-CH_2OH$ | H | OH | $CH_3$ | Cl |
| $-(CH_2)_2-$ | H | $-CH_2-CH_2-N(CH_3)_2$ | H | OH | $CH_3$ | Cl |
| $-(CH_2)_2-$ | H | $-CH_2-CH_2-N(C_2H_5)_2$ | H | OH | $CH_3$ | Cl |
| $-(CH_2)_2-$ | H | $-CH_2-CH_2-N(C_4H_9)_2$ | H | OH | $CH_3$ | Cl |
| $-(CH_2)_2-$ | H | $-CH_2-CH_2-CH_2-N(CH_3)_2$ | H | OH | $CH_3$ | Cl |
| $-(CH_2)_2-$ | H | $-CH_2-CH_2-CH_2-N(C_2H_5)_2$ | H | OH | $CH_3$ | Cl |
| $-(CH_2)_2-$ | H | $-CH_2-CON(CH_3)_2$ | H | OH | $CH_3$ | Cl |
| $-(CH_2)_2-$ | H | $-CH_2-CH_2-CON(CH_3)_2$ | H | OH | $CH_3$ | Cl |
| $-(CH_2)_2-$ | H | $-CH_2-CON(C_2H_5)_2$ | H | OH | $CH_3$ | Cl |
| $-(CH_2)_2-$ | H | $-CH_2-C_6H_5$ | H | OH | $CH_3$ | Cl |
| $-(CH_2)_2-$ | H | $-CH_2-CH_2-C_6H_5$ | H | OH | $CH_3$ | Cl |
| $-(CH_2)_2-$ | H | $-CH_2-CH_2-N\text{(pyrrolidinyl)}$ | H | OH | $CH_3$ | Cl |
| $-(CH_2)_2-$ | H | $-CH_2-CH_2-N\text{(morpholinyl)}$ | H | OH | $CH_3$ | Cl |
| $-(CH_2)_2-$ | H | $-CH_2-CH_2-N\text{(piperidinyl)}$ | H | OH | $CH_3$ | Cl |
| $-(CH_2)_2-$ | H | $-CH_2-CH_2-N\text{(4-methylpiperazinyl)}$ | H | OH | $CH_3$ | Cl |
| $-(CH_2)_2-$ | $n\text{-}C_5H_{11}$ | $n\text{-}C_5H_{11}$ | H | OH | $CH_3$ | Cl |
| $-(CH_2)_2-$ | $n\text{-}C_6H_{13}$ | $n\text{-}C_6H_{13}$ | H | OH | $CH_3$ | Cl |
| $-(CH_2)_2-$ | $i\text{-}C_3H_7$ | $i\text{-}C_3H_7$ | H | OH | $CH_3$ | Cl |
| $-(CH_2)_2-$ | $i\text{-}C_4H_9$ | $i\text{-}C_4H_9$ | H | OH | $CH_3$ | Cl |
| $-(CH_2)_2-$ | $C_2H_4OH$ | $C_2H_4OH$ | H | OH | $CH_3$ | Cl |
| $-(CH_2)_2-$ | $-CH_2-CH(OH)-CH_3$ | $-CH_2-CH(OH)-CH_3$ | H | OH | $CH_3$ | Cl |
| $-(CH_2)_2-$ | $-CH_3$ | $C_2H_4OH$ | H | OH | $CH_3$ | Cl |
| $-(CH_2)_2-$ | $-CH_2-CH_2-CH_2OH$ | $-CH_2-CH_2-CH_2OH$ | H | OH | $CH_3$ | Cl |
| $-(CH_2)_2-$ | $-CH_2-C_6H_5$ | $-CH_2-C_6H_5$ | H | OH | $CH_3$ | Cl |
| $-(CH_2)_2-$ | $-CH_2-CH_2-C_6H_5$ | $-CH_2-CH_2-C_6H_5$ | H | OH | $CH_3$ | Cl |
| $-(CH_2)_2-$ | H | cyclopentyl | H | OH | $CH_3$ | Cl |
| $-(CH_2)_2-$ | H | cyclohexyl | H | OH | $CH_3$ | Cl |

TABLE IIIB-continued

| R₁, R₂ | R₃ | R₄ | R₅ | R₆ | R₇ | R₈ |
|---|---|---|---|---|---|---|
| —(CH₂)₂— | H | cyclohexyl | H | OH | CH₃ | Cl |
| —(CH₂)₂— | | cyclohexyl-COOH | H | OH | CH₃ | Cl |
| —(CH₂)₂— | | cyclohexyl-CH₂-COOH | H | OH | CH₃ | Cl |
| —(CH₂)₂— | | cyclohexyl-CH₂-CH₂-COOH | H | OH | CH₃ | Cl |
| —(CH₂)₂— | | cyclopentyl-COOH | H | OH | CH₃ | Cl |
| —(CH₂)₂— | | cyclohexyl(COOH)(OH) | H | OH | CH₃ | Cl |
| —(CH₂)₃— | H | H | H | OH | CH₃ | Cl |
| —(CH₂)₃— | H | CH₃ | H | OH | CH₃ | Cl |
| —(CH₂)₃— | H | C₂H₅ | H | OH | CH₃ | Cl |
| —(CH₂)₃— | H | n-C₃H₇ | H | OH | CH₃ | Cl |
| —(CH₂)₃— | H | n-C₄H₉ | H | OH | CH₃ | Cl |
| —(CH₂)₃— | H | i-C₃H₇ | H | OH | CH₃ | Cl |
| —(CH₂)₃— | H | i-C₄H₉ | H | OH | CH₃ | Cl |
| —(CH₂)₃— | H | n-C₅H₁₁ | H | OH | CH₃ | Cl |
| —(CH₂)₃— | H | n-C₆H₁₃ | H | OH | CH₃ | Cl |
| —(CH₂)₃— | H | C₂H₄OH | H | OH | CH₃ | Cl |
| —(CH₂)₃— | H | —CH₂—CH(OH)—CH₃ | H | OH | CH₃ | Cl |
| —(CH₂)₃— | H | —CH₂—CH₂—CH₂OH | H | OH | CH₃ | Cl |
| —(CH₂)₃— | H | —CH₂—CH₂—N(CH₃)₂ | H | OH | CH₃ | Cl |
| —(CH₂)₃— | H | —CH₂—CH₂—N(C₂H₅)₂ | H | OH | CH₃ | Cl |
| —(CH₂)₃— | H | —CH₂—CH₂—N(C₄H₉)₂ | H | OH | CH₃ | Cl |
| —(CH₂)₃— | H | —CH₂—CH₂—CH₂—N(CH₃)₂ | H | OH | CH₃ | Cl |
| —(CH₂)₃— | H | —CH₂—CH₂—CH₂—N(C₂H₅)₂ | H | OH | CH₃ | Cl |
| —(CH₂)₃— | H | —CH₂—CON(CH₃)₂ | H | OH | CH₃ | Cl |
| —(CH₂)₃— | H | —CH₂—CH₂—CON(CH₃)₂ | H | OH | CH₃ | Cl |
| —(CH₂)₃— | H | —CH₂—CON(C₂H₅)₂ | H | OH | CH₃ | Cl |
| —(CH₂)₃— | H | —CH₂—C₆H₅ | H | OH | CH₃ | Cl |
| —(CH₂)₃— | H | —CH₂—CH₂—C₆H₅ | H | OH | CH₃ | Cl |

TABLE IIIB-continued

| R₁, R₂ | R₃ | R₄ | R₅ | R₆ | R₇ | R₈ |
|---|---|---|---|---|---|---|
| —(CH₂)₃— | H | —CH₂—CH₂—N⟨pyrrolidine⟩ | H | OH | CH₃ | Cl |
| —(CH₂)₃— | H | —CH₂—CH₂—N⟨morpholine, O⟩ | H | OH | CH₃ | Cl |
| —(CH₂)₃— | H | —CH₂—CH₂—N⟨piperidine⟩ | H | OH | CH₃ | Cl |
| —(CH₂)₃— | H | —CH₂—CH₂—N⟨N-methylpiperazine⟩N—CH₃ | H | OH | CH₃ | Cl |
| —(CH₂)₃— | n-C₅H₁₁ | n-C₅H₁₁ | H | OH | CH₃ | Cl |
| —(CH₂)₃— | n-C₆H₁₃ | n-C₆H₁₃ | H | OH | CH₃ | Cl |
| —(CH₂)₃— | i-C₃H₇ | i-C₃H₇ | H | OH | CH₃ | Cl |
| —(CH₂)₃— | i-C₄H₉ | i-C₄H₉ | H | OH | CH₃ | Cl |
| —(CH₂)₃— | C₂H₄OH | C₂H₄OH | H | OH | CH₃ | Cl |
| —(CH₂)₃— | —CH₂—CH(OH)—CH₃ | —CH₂—CH(OH)—CH₃ | H | OH | CH₃ | Cl |
| —(CH₂)₃— | —CH₃ | C₂H₄OH | H | OH | CH₃ | Cl |
| —(CH₂)₃— | —CH₂—CH₂—CH₂OH | —CH₂—CH₂—CH₂OH | H | OH | CH₃ | Cl |
| —(CH₂)₃— | —CH₂—C₆H₅ | —CH₂—C₆H₅ | H | OH | CH₃ | Cl |
| —(CH₂)₃— | —CH₂—CH₂—C₆H₅ | —CH₂—CH₂—C₆H₅ | H | OH | CH₃ | Cl |
| —(CH₂)₃— | H | cyclopentyl | H | OH | CH₃ | Cl |
| —(CH₂)₃— | H | cyclohexyl | H | OH | CH₃ | Cl |
| —(CH₂)₃— | H | cycloheptyl | H | OH | CH₃ | Cl |
| —(CH₂)₃— |  | cyclohexyl—COOH | H | OH | CH₃ | Cl |
| —(CH₂)₃— |  | cyclohexyl—CH₂—COOH | H | OH | CH₃ | Cl |
| —(CH₂)₃— |  | cyclohexyl—CH₂—CH₂—COOH | H | OH | CH₃ | Cl |

TABLE IIIB-continued

| $R_1, R_2$ | $R_3$ | $R_4$ | $R_5$ | $R_6$ | $R_7$ | $R_8$ |
|---|---|---|---|---|---|---|
| $-(CH_2)_3-$ | | cyclopentyl-COOH | H | OH | $CH_3$ | Cl |
| $-(CH_2)_3-$ | | COOH, cyclohexyl-OH | H | OH | $CH_3$ | Cl |

Table IVA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | OH | H | $CH_3$ | H |
| $CH_3$ | $CH_3$ | $C_2H_5$ | OH | H | $CH_3$ | H |
| $CH_3$ | $C_2H_5$ | $C_2H_5$ | OH | H | $CH_3$ | H |
| $CH_3$ | $n$-$C_3H_7$ | $n$-$C_3H_7$ | OH | H | $CH_3$ | H |
| $CH_3$ | $n$-$C_4H_9$ | $n$-$C_4H_9$ | OH | H | $CH_3$ | H |
| $CH_3$ | H | $CH_2-COOH$ | OH | H | $CH_3$ | H |
| $CH_3$ | H | $CH_2-COOC_2H_5$ | OH | H | $CH_3$ | H |
| $CH_3$ | H | $CH_3-CH-COOH$ | OH | H | $CH_3$ | H |
| $CH_3$ | H | $CH_3-CH-COOC_2H_5$ | OH | H | $CH_3$ | H |
| $CH_3$ | H | $-CH_2-CH_2-COOH$ | OH | H | $CH_3$ | H |
| $CH_3$ | H | $-CH_2-CH_2-COOC_2H_5$ | OH | H | $CH_3$ | H |
| $CH_3$ | H | $-(CH_2)_4-CH(NH_2)-COOH$ | OH | H | $CH_3$ | H |
| $CH_3$ | \multicolumn{2}{c|}{cyclopentyl ($R_3$+$R_4$)} | OH | H | $CH_3$ | H |
| $CH_3$ | \multicolumn{2}{c|}{cyclohexyl ($R_3$+$R_4$)} | OH | H | $CH_3$ | H |
| $CH_3$ | \multicolumn{2}{c|}{tetrahydropyranyl (O)} | OH | H | $CH_3$ | H |
| $CH_3$ | \multicolumn{2}{c|}{piperidinyl (NH)} | OH | H | $CH_3$ | H |
| $CH_3$ | \multicolumn{2}{c|}{N-methylpiperidinyl (N-$CH_3$)} | OH | H | $CH_3$ | H |

Table IVA-continued

| R₁, R₂ | R₃ | R₄ | R₅ | R₆ | R₇ | R₈ |
|---|---|---|---|---|---|---|
| $CH_3$ | | piperidine-N—$C_2H_5$ | OH | H | $CH_3$ | H |
| $CH_3$ | | piperidine-N—$C_2H_5OH$ | OH | H | $CH_3$ | H |
| $C_2H_5$ | $CH_3$ | $CH_3$ | OH | H | $CH_3$ | H |
| $C_2H_5$ | $CH_3$ | $C_2H_5$ | OH | H | $CH_3$ | H |
| $C_2H_5$ | $C_2H_5$ | $C_2H_5$ | OH | H | $CH_3$ | H |
| $C_2H_5$ | n-$C_3H_7$ | n-$C_3H_7$ | OH | H | $CH_3$ | H |
| $C_2H_5$ | n-$C_4H_9$ | n-$C_4H_9$ | OH | H | $CH_3$ | H |
| $C_2H_5$ | H | $CH_2$—COOH | OH | H | $CH_3$ | H |
| $C_2H_5$ | H | $CH_2$—$COOC_2H_5$ | OH | H | $CH_3$ | H |
| $C_2H_5$ | H | $CH_3$—CH—COOH | OH | H | $CH_3$ | H |
| $C_2H_5$ | H | $CH_3$—CH—$COOC_2H_5$ | OH | H | $CH_3$ | H |
| $C_2H_5$ | H | —$CH_2$—$CH_2$—COOH | OH | H | $CH_3$ | H |
| $C_2H_5$ | H | —$CH_2$—$CH_2$—$COOC_2H_5$ | OH | H | $CH_3$ | H |
| $C_2H_5$ | H | —$(CH_2)_4$—CH(NH₂)—COOH | OH | H | $CH_3$ | H |
| $C_2H_5$ | \{ R₃ and R₄ together: cyclopentyl \} | | OH | H | $CH_3$ | H |
| $C_2H_5$ | \{ R₃ and R₄ together: cyclohexyl \} | | OH | H | $CH_3$ | H |
| $C_2H_5$ | \{ R₃ and R₄ together: tetrahydropyranyl (O) \} | | OH | H | $CH_3$ | H |
| $C_2H_5$ | \{ R₃ and R₄ together: piperidino (N) \} | | OH | H | $CH_3$ | H |
| $C_2H_5$ | \{ R₃ and R₄ together: N—$CH_3$ piperazine \} | | OH | H | $CH_3$ | H |
| $C_2H_5$ | \{ R₃ and R₄ together: N—$C_2H_5$ piperazine \} | | OH | H | $CH_3$ | H |
| $C_2H_5$ | \{ R₃ and R₄ together: N—$C_2H_5OH$ piperazine \} | | OH | H | $CH_3$ | H |

Table IVA-continued

| R₁, R₂ | R₃ | R₄ | R₅ | R₆ | R₇ | R₈ |
|---|---|---|---|---|---|---|
| n-C₃H₇ | CH₃ | CH₃ | OH | H | CH₃ | H |
| n-C₃H₇ | CH₃ | C₂H₅ | OH | H | CH₃ | H |
| n-C₃H₇ | C₂H₅ | C₂H₅ | OH | H | CH₃ | H |
| n-C₃H₇ | n-C₃H₇ | n-C₃H₇ | OH | H | CH₃ | H |
| n-C₃H₇ | n-C₄H₉ | n-C₄H₉ | OH | H | CH₃ | H |
| n-C₃H₇ | H | CH₂—COOH | OH | H | CH₃ | H |
| n-C₃H₇ | H | CH₂—COOC₂H₅ | OH | H | CH₃ | H |
| n-C₃H₇ | H | CH₃—CH(—)—COOH | OH | H | CH₃ | H |
| n-C₃H₇ | H | CH₃—CH(—)—COOC₂H₅ | OH | H | CH₃ | H |
| n-C₃H₇ | H | —CH₂—CH₂—COOH | OH | H | CH₃ | H |
| n-C₃H₇ | H | —CH₂—CH₂—COOC₂H₅ | OH | H | CH₃ | H |
| n-C₃H₇ | H | —(CH₂)₄—CH(NH₂)—COOH | OH | H | CH₃ | H |
| n-C₃H₇ | \multicolumn{2}{c}{cyclopentyl (R₃ and R₄ together)} | OH | H | CH₃ | H |
| n-C₃H₇ | \multicolumn{2}{c}{cyclohexyl} | OH | H | CH₃ | H |
| n-C₃H₇ | \multicolumn{2}{c}{tetrahydropyranyl (O in ring)} | OH | H | CH₃ | H |
| n-C₃H₇ | \multicolumn{2}{c}{piperidinyl (NH)} | OH | H | CH₃ | H |
| n-C₃H₇ | \multicolumn{2}{c}{N—CH₃ piperidinyl} | OH | H | CH₃ | H |
| n-C₃H₇ | \multicolumn{2}{c}{N—C₂H₅ piperidinyl} | OH | H | CH₃ | H |
| n-C₃H₇ | \multicolumn{2}{c}{N—C₂H₅OH piperidinyl} | OH | H | CH₃ | H |
| n-C₄H₉ | CH₃ | CH₃ | OH | H | CH₃ | H |
| n-C₄H₉ | CH₃ | C₂H₅ | OH | H | CH₃ | H |
| n-C₄H₉ | C₂H₅ | C₂H₅ | OH | H | CH₃ | H |
| n-C₄H₉ | n-C₃H₇ | n-C₃H₇ | OH | H | CH₃ | H |
| n-C₄H₉ | n-C₄H₉ | n-C₄H₉ | OH | H | CH₃ | H |
| n-C₄H₉ | H | CH₂—COOH | OH | H | CH₃ | H |

Table IVA-continued

| $R_1, R_2$ | $R_3$ | $R_4$ | $R_5$ | $R_6$ | $R_7$ | $R_8$ |
|---|---|---|---|---|---|---|
| n-$C_4H_9$ | H | $CH_2-COOC_2H_5$ | OH | H | $CH_3$ | H |
| n-$C_4H_9$ | H | $CH_3-CH-COOH$ <br> $\quad\quad\;\;\,\vert$ | OH | H | $CH_3$ | H |
| n-$C_4H_9$ | H | $CH_3-CH-COOC_2H_5$ <br> $\quad\quad\;\;\,\vert$ | OH | H | $CH_3$ | H |
| n-$C_4H_9$ | H | $-CH_2-CH_2-COOH$ | OH | H | $CH_3$ | H |
| n-$C_4H_9$ | H | $-CH_2-CH_2-COOC_2H_5$ | OH | H | $CH_3$ | H |
| n-$C_4H_9$ | H | $-(CH_2)_4-CH-COOH$ <br> $\quad\quad\quad\quad\quad\;\vert$ <br> $\quad\quad\quad\quad\quad NH_2$ | OH | H | $CH_3$ | H |
| n-$C_4H_9$ | H | cyclopentyl | OH | H | $CH_3$ | H |
| n-$C_4H_9$ | H | cyclohexyl | OH | H | $CH_3$ | H |
| n-$C_4H_9$ | H | tetrahydropyranyl (O) | OH | H | $CH_3$ | H |
| n-$C_4H_9$ | H | piperidinyl (N-H) | OH | H | $CH_3$ | H |
| n-$C_4H_9$ | H | N-methylpiperidinyl ($N-CH_3$) | OH | H | $CH_3$ | H |
| n-$C_4H_9$ | H | N-ethylpiperidinyl ($N-C_2H_5$) | OH | H | $CH_3$ | H |
| n-$C_4H_9$ | H | N-(2-hydroxyethyl)piperidinyl ($N-C_2H_5OH$) | OH | H | $CH_3$ | H |

TABLE IVB

| $R_1, R_2$ | $R_3$ | $R_4$ | $R_5$ | $R_6$ | $R_7$ | $R_8$ |
|---|---|---|---|---|---|---|
| $CH_3$ | H | H | OH | H | $CH_3$ | H |
| $CH_3$ | H | $CH_3$ | OH | H | $CH_3$ | H |
| $CH_3$ | H | $C_2H_5$ | OH | H | $CH_3$ | H |
| $CH_3$ | H | n-$C_3H_7$ | OH | H | $CH_3$ | H |
| $CH_3$ | H | n-$C_4H_9$ | OH | H | $CH_3$ | H |
| $CH_3$ | H | i-$C_3H_7$ | OH | H | $CH_3$ | H |
| $CH_3$ | H | i-$C_4H_9$ | OH | H | $CH_3$ | H |
| $CH_3$ | H | n-$C_5H_{11}$ | OH | H | $CH_3$ | H |
| $CH_3$ | H | n-$C_6H_{13}$ | OH | H | $CH_3$ | H |

TABLE IVB-continued

| $R_1, R_2$ | $R_3$ | $R_4$ | $R_5$ | $R_6$ | $R_7$ | $R_8$ |
|---|---|---|---|---|---|---|
| $CH_3$ | H | $C_2H_4OH$ | OH | H | $CH_3$ | H |
| $CH_3$ | H | $-CH_2-\underset{\underset{OH}{\vert}}{CH}-CH_3$ | OH | H | $CH_3$ | H |
| $CH_3$ | H | $-CH_2-CH_2-CH_2OH$ | OH | H | $CH_3$ | H |
| $CH_3$ | H | $-CH_2-CH_2-N(CH_3)_2$ | OH | H | $CH_3$ | H |
| $CH_3$ | H | $-CH_2-CH_2-N(C_2H_5)_2$ | OH | H | $CH_3$ | H |
| $CH_3$ | H | $-CH_2-CH_2-N(C_4H_9)_2$ | OH | H | $CH_3$ | H |
| $CH_3$ | H | $-CH_2-CH_2-CH_2-N(CH_3)_2$ | OH | H | $CH_3$ | H |
| $CH_3$ | H | $-CH_2-CH_2-CH_2-N(C_2H_5)_2$ | OH | H | $CH_3$ | H |
| $CH_3$ | H | $-CH_2-CON(CH_3)_2$ | OH | H | $CH_3$ | H |
| $CH_3$ | H | $-CH_2-CH_2-CON(CH_3)_2$ | OH | H | $CH_3$ | H |
| $CH_3$ | H | $-CH_2-CON(C_2H_5)_2$ | OH | H | $CH_3$ | H |
| $CH_3$ | H | $-CH_2-C_6H_5$ | OH | H | $CH_3$ | H |
| $CH_3$ | H | $-CH_2-CH_2-C_6H_5$ | OH | H | $CH_3$ | H |
| $CH_3$ | H | 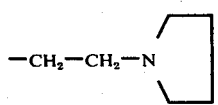 | OH | H | $CH_3$ | H |
| $CH_3$ | H | 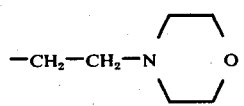 | OH | H | $CH_3$ | H |
| $CH_3$ | H | 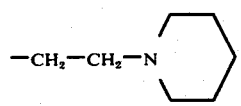 | OH | H | $CH_3$ | H |
| $CH_3$ | H | 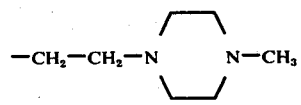 | OH | H | $CH_3$ | H |
| $CH_3$ | $n-C_5H_{11}$ | $n-C_5H_{11}$ | OH | H | $CH_3$ | H |
| $CH_3$ | $n-C_6H_{13}$ | $n-C_6H_{13}$ | OH | H | $CH_3$ | H |
| $CH_3$ | $i-C_3H_7$ | $i-C_3H_7$ | OH | H | $CH_3$ | H |
| $CH_3$ | $i-C_4H_9$ | $i-C_4H_9$ | OH | H | $CH_3$ | H |
| $CH_3$ | $C_2H_4OH$ | $C_2H_4OH$ | OH | H | $CH_3$ | H |
| $CH_3$ | $-CH_2-\underset{\underset{OH}{\vert}}{CH}-CH_3$ | $-CH_2-\underset{\underset{OH}{\vert}}{CH}-CH_3$ | OH | H | $CH_3$ | H |
| $CH_3$ | $-CH_3$ | $C_2H_4OH$ | OH | H | $CH_3$ | H |
| $CH_3$ | $-CH_2-CH_2-CH_2OH$ | $-CH_2-CH_2-CH_2OH$ | OH | H | $CH_3$ | H |
| $CH_3$ | $-CH_2-C_6H_5$ | $-CH_2-C_6H_5$ | OH | H | $CH_3$ | H |
| $CH_3$ | $-CH_2-CH_2-C_6H_5$ | $-CH_2-CH_2-C_6H_5$ | OH | H | $CH_3$ | H |
| $CH_3$ | H | 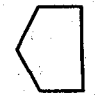 | OH | H | $CH_3$ | H |
| $CH_3$ | H | 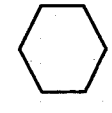 | OH | H | $CH_3$ | H |

TABLE IVB-continued

| $R_1, R_2$ | $R_3$ | $R_4$ | $R_5$ | $R_6$ | $R_7$ | $R_8$ |
|---|---|---|---|---|---|---|
| $CH_3$ | H | cycloheptyl ⎫ | OH | H | $CH_3$ | H |
| $CH_3$ |  | cyclohexyl-COOH ⎬ | OH | H | $CH_3$ | H |
| $CH_3$ |  | cyclohexyl-$CH_2$-COOH | OH | H | $CH_3$ | H |
| $CH_3$ |  | cyclohexyl-$CH_2$-$CH_2$-COOH | OH | H | $CH_3$ | H |
| $CH_3$ |  | cyclopentyl-COOH | OH | H | $CH_3$ | H |
| $CH_3$ |  | COOH, cyclohexyl-OH | OH | H | $CH_3$ | H |
| $C_2H_5$ | H | H | OH | H | $CH_3$ | H |
| $C_2H_5$ | H | $CH_3$ | OH | H | $CH_3$ | H |
| $C_2H_5$ | H | $C_2H_5$ | OH | H | $CH_3$ | H |
| $C_2H_5$ | H | n-$C_3H_7$ | OH | H | $CH_3$ | H |
| $C_2H_5$ | H | n-$C_4H_9$ | OH | H | $CH_3$ | H |
| $C_2H_5$ | H | i-$C_3H_7$ | OH | H | $CH_3$ | H |
| $C_2H_5$ | H | i-$C_4H_9$ | OH | H | $CH_3$ | H |
| $C_2H_5$ | H | n-$C_5H_{11}$ | OH | H | $CH_3$ | H |
| $C_2H_5$ | H | n-$C_6H_{13}$ | OH | H | $CH_3$ | H |
| $C_2H_5$ | H | $C_2H_4OH$ | OH | H | $CH_3$ | H |
| $C_2H_5$ | H | $-CH_2-CH-CH_3$<br>     $\|$<br>     OH | OH | H | $CH_3$ | H |
| $CH_2H_5$ | H | $-CH_2-CH_2-CH_2OH$ | OH | H | $CH_3$ | H |
| $C_2H_5$ | H | $-CH_2-CH_2-N(CH_3)_2$ | OH | H | $CH_3$ | H |
| $C_2H_5$ | H | $-CH_2-CH_2-N(C_2H_5)_2$ | OH | H | $CH_3$ | H |
| $C_2H_5$ | H | $-CH_2-CH_2-N(C_4H_9)_2$ | OH | H | $CH_3$ | H |
| $C_2H_5$ | H | $-CH_2-CH_2-CH_2-N(CH_3)_2$ | OH | H | $CH_3$ | H |
| $C_2H_5$ | H | $-CH_2-CH_2-CH_2-N(C_2H_5)_2$ | OH | H | $CH_3$ | H |
| $C_2H_5$ | H | $-CH_2-CON(CH_3)_2$ | OH | H | $CH_3$ | H |
| $C_2H_5$ | H | $-CH_2-CH_2-CON(CH_3)_2$ | OH | H | $CH_3$ | H |
| $C_2H_5$ | H | $-CH_2-CON(C_2H_5)_2$ | OH | H | $CH_3$ | H |
| $C_2H_5$ | H | $-CH_2-C_6H_5$ | OH | H | $CH_3$ | H |
| $C_2H_5$ | H | $-CH_2-CH_2-C_6H_5$ | OH | H | $CH_3$ | H |

TABLE IVB-continued

| R₁, R₂ | R₃ | R₄ | R₅ | R₆ | R₇ | R₈ |
|---|---|---|---|---|---|---|
| $C_2H_5$ | H | $-CH_2-CH_2-N\begin{pmatrix}\text{pyrrolidinyl}\end{pmatrix}$ | OH | H | $CH_3$ | H |
| $C_2H_5$ | H | $-CH_2-CH_2-N\begin{pmatrix}\text{morpholinyl}\end{pmatrix}O$ | OH | H | $CH_3$ | H |
| $C_2H_5$ | H | $-CH_2-CH_2-N\begin{pmatrix}\text{piperidinyl}\end{pmatrix}$ | OH | H | $CH_3$ | H |
| $C_2H_5$ | H | $-CH_2-CH_2-N\begin{pmatrix}\text{piperazinyl}\end{pmatrix}N-CH_3$ | OH | H | $CH_3$ | H |
| $C_2H_5$ | n-$C_5H_{11}$ | n-$C_5H_{11}$ | OH | H | $CH_3$ | H |
| $C_2H_5$ | n-$C_6H_{13}$ | n-$C_6H_{13}$ | OH | H | $CH_3$ | H |
| $C_2H_5$ | i-$C_3H_7$ | i-$C_3H_7$ | OH | H | $CH_3$ | H |
| $C_2H_5$ | i-$C_4H_9$ | i-$C_4H_9$ | OH | H | $CH_3$ | H |
| $C_2H_5$ | $C_2H_4OH$ | $C_2H_4OH$ | OH | H | $CH_3$ | H |
| $C_2H_5$ | $-CH_2-\underset{OH}{CH}-CH_3$ | $-CH_2-\underset{OH}{CH}-CH_3$ | OH | H | $CH_3$ | H |
| $C_2H_5$ | $-CH_3$ | $C_2H_4OH$ | OH | H | $CH_3$ | H |
| $C_2H_5$ | $-CH_2-CH_2-CH_2OH$ | $-CH_2-CH_2-CH_2OH$ | OH | H | $CH_3$ | H |
| $C_2H_5$ | $-CH_2-C_6H_5$ | $-CH_2-C_6H_5$ | OH | H | $CH_3$ | H |
| $C_2H_5$ | $-CH_2-CH_2-C_6H_5$ | $-CH_2-CH_2-C_6H_5$ | OH | H | $CH_3$ | H |
| $C_2H_5$ | H | cyclopentyl | OH | H | $CH_3$ | H |
| $C_2H_5$ | H | cyclohexyl | OH | H | $CH_3$ | H |
| $C_2H_5$ | H | cyclooctyl | OH | H | $CH_3$ | H |
| $C_2H_5$ | | cyclohexyl-COOH | OH | H | $CH_3$ | H |
| $C_2H_5$ | | cyclohexyl-$CH_2$-COOH | OH | H | $CH_3$ | H |
| $C_2H_5$ | | cyclohexyl-$CH_2-CH_2$-COOH | OH | H | $CH_3$ | H |

TABLE IVB-continued

| $R_1$, $R_2$ | $R_3$ | $R_4$ | $R_5$ | $R_6$ | $R_7$ | $R_8$ |
|---|---|---|---|---|---|---|
| $C_2H_5$ | | cyclopentyl-COOH | OH | H | $CH_3$ | H |
| $C_2H_5$ | COOH | cyclohexyl-OH | OH | H | $CH_3$ | H |
| n-$C_3H_7$ | H | H | OH | H | $CH_3$ | H |
| n-$C_3H_7$ | H | $CH_3$ | OH | H | $CH_3$ | H |
| n-$C_3H_7$ | H | $C_2H_5$ | OH | H | $CH_3$ | H |
| n-$C_3H_7$ | H | n-$C_3H_7$ | OH | H | $CH_3$ | H |
| n-$C_3H_7$ | H | n-$C_4H_9$ | OH | H | $CH_3$ | H |
| n-$C_3H_7$ | H | i-$C_3H_7$ | OH | H | $CH_3$ | H |
| n-$C_3H_7$ | H | i-$C_4H_9$ | OH | H | $CH_3$ | H |
| n-$C_3H_7$ | H | n-$C_5H_{11}$ | OH | H | $CH_3$ | H |
| n-$C_3H_7$ | H | n-$C_6H_{13}$ | OH | H | $CH_3$ | H |
| n-$C_3H_7$ | H | $C_2H_4OH$ | OH | H | $CH_3$ | H |
| n-$C_3H_7$ | H | $-CH_2-CH(OH)-CH_3$ | OH | H | $CH_3$ | H |
| n-$C_3H_7$ | H | $-CH_2-CH_2-CH_2OH$ | OH | H | $CH_3$ | H |
| n-$C_3H_7$ | H | $-CH_2-CH_2-N(CH_3)_2$ | OH | H | $CH_3$ | H |
| n-$C_3H_7$ | H | $-CH_2-CH_2-N(C_2H_5)_2$ | OH | H | $CH_3$ | H |
| n-$C_3H_7$ | H | $-CH_2-CH_2-N(C_4H_9)_2$ | OH | H | $CH_3$ | H |
| n-$C_3H_7$ | H | $-CH_2-CH_2-CH_2-N(CH_3)_2$ | OH | H | $CH_3$ | H |
| n-$C_3H_7$ | H | $-CH_2-CH_2-CH_2-N(C_2H_5)_2$ | OH | H | $CH_3$ | H |
| n-$C_3H_7$ | H | $-CH_2-CON(CH_3)_2$ | OH | H | $CH_3$ | H |
| n-$C_3H_7$ | H | $-CH_2-CH_2-CON(CH_3)_2$ | OH | H | $CH_3$ | H |
| n-$C_3H_7$ | H | $-CH_2-CON(C_2H_5)_2$ | OH | H | $CH_3$ | H |
| n-$C_3H_7$ | H | $-CH_2-C_6H_5$ | OH | H | $CH_3$ | H |
| n-$C_3H_7$ | H | $-CH_2-CH_2-C_6H_5$ | OH | H | $CH_3$ | H |
| n-$C_3H_7$ | H | $-CH_2-CH_2-N$(pyrrolidino) | OH | H | $CH_3$ | H |
| n-$C_3H_7$ | H | $-CH_2-CH_2-N$(morpholino) | OH | H | $CH_3$ | H |
| n-$C_3H_7$ | H | $-CH_2-CH_2-N$(piperidino) | OH | H | $CH_3$ | H |
| n-$C_3H_7$ | H | $-CH_2-CH_2-N$(N-methylpiperazino)$-CH_3$ | OH | H | $CH_3$ | H |
| n-$C_3H_7$ | n-$C_5H_{11}$ | n-$C_5H_{11}$ | OH | H | $CH_3$ | H |

TABLE IVB-continued

| $R_1$, $R_2$ | $R_3$ | $R_4$ | $R_5$ | $R_6$ | $R_7$ | $R_8$ |
|---|---|---|---|---|---|---|
| n-$C_3H_7$ | n-$C_6H_{13}$ | n-$C_6H_{13}$ | OH | H | $CH_3$ | H |
| n-$C_3H_7$ | i-$C_3H_7$ | i-$C_3H_7$ | OH | H | $CH_3$ | H |
| n-$C_3H_7$ | i-$C_4H_9$ | i-$C_4H_9$ | OH | H | $CH_3$ | H |
| n-$C_3H_7$ | $C_2H_4OH$ | $C_2H_4OH$ | OH | H | $CH_3$ | H |
| n-$C_3H_7$ | —$CH_2$—CH(OH)—$CH_3$ | —$CH_2$—CH(OH)—$CH_3$ | OH | H | $CH_3$ | H |
| n-$C_3H_7$ | —$CH_3$ | $C_2H_4OH$ | OH | H | $CH_3$ | H |
| n-$C_3H_7$ | —$CH_2$—$CH_2$—$CH_2OH$ | —$CH_2$—$CH_2$—$CH_2OH$ | OH | H | $CH_3$ | H |
| n-$C_3H_7$ | —$CH_2$—$C_6H_5$ | —$CH_2$—$C_6H_5$ | OH | H | $CH_3$ | H |
| n-$C_3H_7$ | —$CH_2$—$CH_2$—$C_6H_5$ | —$CH_2$—$CH_2$—$C_6H_5$ | OH | H | $CH_3$ | H |
| n-$C_3H_7$ | H | cyclopentyl | OH | H | $CH_3$ | H |
| n-$C_3H_7$ | H | cyclohexyl | OH | H | $CH_3$ | H |
| n-$C_3H_7$ | H | cyclooctyl | OH | H | $CH_3$ | H |
| n-$C_3H_7$ | \multicolumn{2}{c|}{cyclohexyl-COOH} | OH | H | $CH_3$ | H |
| n-$C_3H_7$ | \multicolumn{2}{c|}{cyclohexyl-$CH_2$-COOH} | OH | H | $CH_3$ | H |
| n-$C_3H_7$ | \multicolumn{2}{c|}{cyclohexyl-$CH_2$-$CH_2$-COOH} | OH | H | $CH_3$ | H |
| n-$C_3H_7$ | \multicolumn{2}{c|}{cyclopentyl-COOH} | OH | H | $CH_3$ | H |
| n-$C_3H_7$ | \multicolumn{2}{c|}{2-hydroxycyclopentyl-COOH} | OH | H | $CH_3$ | H |
| n-$C_4H_9$ | H | H | OH | H | $CH_3$ | H |
| n-$C_4H_9$ | H | $CH_3$ | OH | H | $CH_3$ | H |
| n-$C_4H_9$ | H | $C_2H_5$ | OH | H | $CH_3$ | H |
| n-$C_4H_9$ | H | n-$C_3H_7$ | OH | H | $CH_3$ | H |
| n-$C_4H_9$ | H | n-$C_4H_9$ | OH | H | $CH_3$ | H |
| n-$C_4H_9$ | H | i-$C_3H_7$ | OH | H | $CH_3$ | H |
| n-$C_4H_9$ | H | i-$C_4H_9$ | OH | H | $CH_3$ | H |

TABLE IVB-continued

| $R_1, R_2$ | $R_3$ | $R_4$ | $R_5$ | $R_6$ | $R_7$ | $R_8$ |
|---|---|---|---|---|---|---|
| n-$C_4H_9$ | H | n-$C_5H_{11}$ | OH | H | $CH_3$ | H |
| n-$C_4H_9$ | H | n-$C_6H_{13}$ | OH | H | $CH_3$ | H |
| n-$C_4H_9$ | H | $C_2H_4OH$ | OH | H | $CH_3$ | H |
| n-$C_4H_9$ | H | —$CH_2$—CH(OH)—$CH_3$ | OH | H | $CH_3$ | H |
| n-$C_4H_9$ | H | —$CH_2$—$CH_2$—$CH_2OH$ | OH | H | $CH_3$ | H |
| n-$C_4H_9$ | H | —$CH_2$—$CH_2$—$N(CH_3)_2$ | OH | H | $CH_3$ | H |
| n-$C_4H_9$ | H | —$CH_2$—$CH_2$—$N(C_2H_5)_2$ | OH | H | $CH_3$ | H |
| n-$C_4H_9$ | H | —$CH_2$—$CH_2$—$N(C_4H_9)_2$ | OH | H | $CH_3$ | H |
| n-$C_4H_9$ | H | —$CH_2$—$CH_2$—$CH_2$—$N(CH_3)_2$ | OH | H | $CH_3$ | H |
| n-$C_4H_9$ | H | —$CH_2$—$CH_2$—$CH_2$—$N(C_2H_5)_2$ | OH | H | $CH_3$ | H |
| n-$C_4H_9$ | H | —$CH_2$—$CON(CH_3)_2$ | OH | H | $CH_3$ | H |
| n-$C_4H_9$ | H | —$CH_2$—$CH_2$—$CON(CH_3)_2$ | OH | H | $CH_3$ | H |
| n-$C_4H_9$ | H | —$CH_2$—$CON(C_2H_5)_2$ | OH | H | $CH_3$ | H |
| n-$C_4H_9$ | H | —$CH_2$—$C_6H_5$ | OH | H | $CH_3$ | H |
| n-$C_4H_9$ | H | —$CH_2$—$CH_2$—$C_6H_5$ | OH | H | $CH_3$ | H |
| n-$C_4H_9$ | H | —$CH_2$—$CH_2$—N(pyrrolidinyl) | OH | H | $CH_3$ | H |
| n-$C_4H_9$ | H | —$CH_2$—$CH_2$—N(morpholinyl) | OH | H | $CH_3$ | H |
| n-$C_4H_9$ | H | —$CH_2$—$CH_2$—N(piperidinyl) | OH | H | $CH_3$ | H |
| n-$C_4H_9$ | H | —$CH_2$—$CH_2$—N(N′-methylpiperazinyl) | OH | H | $CH_3$ | H |
| n-$C_4H_9$ | n-$C_5H_{11}$ | n-$C_5H_{11}$ | OH | H | $CH_3$ | H |
| n-$C_4H_9$ | n-$C_6H_{13}$ | n-$C_6H_{13}$ | OH | H | $CH_3$ | H |
| n-$C_4H_9$ | i-$C_3H_7$ | i-$C_3H_7$ | OH | H | $CH_3$ | H |
| n-$C_4H_9$ | i-$C_4H_9$ | i-$C_4H_9$ | OH | H | $CH_3$ | H |
| n-$C_4H_9$ | $C_2H_4OH$ | $C_2H_4OH$ | OH | H | $CH_3$ | H |
| n-$C_4H_9$ | —$CH_2$—CH(OH)—$CH_3$ | —$CH_2$—CH(OH)—$CH_3$ | OH | H | $CH_3$ | H |
| n-$C_4H_9$ | —$CH_3$ | $C_2H_4OH$ | OH | H | $CH_3$ | H |
| n-$C_4H_9$ | —$CH_2$—$CH_2$—$CH_2OH$ | —$CH_2$—$CH_2$—$CH_2OH$ | OH | H | $CH_3$ | H |
| n-$C_4H_9$ | —$CH_2$—$C_6H_5$ | —$CH_2$—$C_6H_5$ | OH | H | $CH_3$ | H |
| n-$C_4H_9$ | —$CH_2$—$CH_2$—$C_6H_5$ | —$CH_2$—$CH_2$—$C_6H_5$ | OH | H | $CH_3$ | H |
| n-$C_4H_9$ | H | cyclohexyl | OH | H | $CH_3$ | H |

TABLE IVB-continued

| $R_1, R_2$ | $R_3$ | $R_4$ | $R_5$ | $R_6$ | $R_7$ | $R_8$ |
|---|---|---|---|---|---|---|
| n-$C_4H_9$ | H |  | OH | H | $CH_3$ | H |
| n-$C_4H_9$ | H |  | OH | H | $CH_3$ | H |
| n-$C_4H_9$ | | 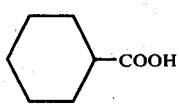—COOH | OH | H | $CH_3$ | H |
| n-$C_4H_9$ | | 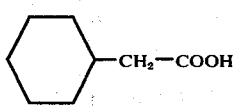—$CH_2$—COOH | OH | H | $CH_3$ | H |
| n-$C_4H_9$ | | 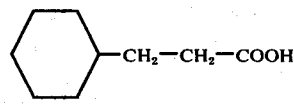—$CH_2$—$CH_2$—COOH | OH | H | $CH_3$ | H |
| n-$C_4H_9$ | | 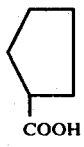 COOH | OH | H | $CH_3$ | H |
| n-$C_4H_9$ | COOH | 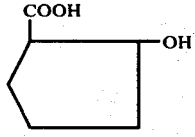 OH | OH | H | $CH_3$ | H |
| —$(CH_2)_2$— | H | H | OH | H | $CH_3$ | H |
| —$(CH_2)_2$— | H | $CH_3$ | OH | H | $CH_3$ | H |
| —$(CH_2)_2$— | H | $C_2H_5$ | OH | H | $CH_3$ | H |
| —$(CH_2)_2$— | H | n-$C_3H_7$ | OH | H | $CH_3$ | H |
| —$(CH_2)_2$— | H | n-$C_4H_9$ | OH | H | $CH_3$ | H |
| —$(CH_2)_2$— | H | i-$C_3H_7$ | OH | H | $CH_3$ | H |
| —$(CH_2)_2$— | H | i-$C_4H_9$ | OH | H | $CH_3$ | H |
| —$(CH_2)_2$— | H | n-$C_5H_{11}$ | OH | H | $CH_3$ | H |
| —$(CH_2)_2$— | H | n-$C_6H_{13}$ | OH | H | $CH_3$ | H |
| —$(CH_2)_2$— | H | $C_2H_4OH$ | OH | H | $CH_3$ | H |
| —$(CH_2)_2$— | H | —$CH_2$—CH—$CH_3$<br>　　　　　OH | OH | H | $CH_3$ | H |
| —$(CH_2)_2$— | H | —$CH_2$—$CH_2$—$CH_2OH$ | OH | H | $CH_3$ | H |
| —$(CH_2)_2$— | H | —$CH_2$—$CH_2$—$N(CH_3)_2$ | OH | H | $CH_3$ | H |
| —$(CH_2)_2$— | H | —$CH_2$—$CH_2$—$N(C_2H_5)_2$ | OH | H | $CH_3$ | H |
| —$(CH_2)_2$— | H | —$CH_2$—$CH_2$—$N(C_4H_9)_2$ | OH | H | $CH_3$ | H |
| —$(CH_2)_2$— | H | —$CH_2$—$CH_2$—$CH_2$—$N(CH_3)_2$ | OH | H | $CH_3$ | H |
| —$(CH_2)_2$— | H | —$CH_2$—$CH_2$—$CH_2$—$N(C_2H_5)_2$ | OH | H | $CH_3$ | H |
| —$(CH_2)_2$— | H | —$CH_2$—$CON(CH_3)_2$ | OH | H | $CH_3$ | H |
| —$(CH_2)_2$— | H | —$CH_2$—$CH_2$—$CON(CH_3)_2$ | OH | H | $CH_3$ | H |

TABLE IVB-continued

| R₁, R₂ | R₃ | R₄ | R₅ | R₆ | R₇ | R₈ |
|---|---|---|---|---|---|---|
| —(CH₂)₂— | H | —CH₂—CON(C₂H₅)₂ | OH | H | CH₃ | H |
| —(CH₂)₂— | H | —CH₂—C₆H₅ | OH | H | CH₃ | H |
| —(CH₂)₂— | H | —CH₂—CH₂—C₆H₅ | OH | H | CH₃ | H |
| —(CH₂)₂— | H | —CH₂—CH₂—N⟨pyrrolidine⟩ | OH | H | CH₃ | H |
| —(CH₂)₂— | H | —CH₂—CH₂—N⟨morpholine⟩O | OH | H | CH₃ | H |
| —(CH₂)₂— | H | —CH₂—CH₂—N⟨piperidine⟩ | OH | H | CH₃ | H |
| —(CH₂)₂— | H | —CH₂—CH₂—N⟨piperazine⟩N—CH₃ | OH | H | CH₃ | H |
| —(CH₂)₂— | n-C₅H₁₁ | n-C₅H₁₁ | OH | H | CH₃ | H |
| —(CH₂)₂— | n-C₆H₁₃ | n-C₆H₁₃ | OH | H | CH₃ | H |
| —(CH₂)₂— | i-C₃H₇ | i-C₃H₇ | OH | H | CH₃ | H |
| —(CH₂)₂— | i-C₄H₉ | i-C₄H₉ | OH | H | CH₃ | H |
| —(CH₂)₂— | C₂H₄OH | C₂H₄OH | OH | H | CH₃ | H |
| —(CH₂)₂— | —CH₂—CH(OH)—CH₃ | —CH₂—CH(OH)—CH₃ | OH | H | CH₃ | H |
| —(CH₂)₂— | —CH₃ | C₂H₄OH | OH | H | CH₃ | H |
| —(CH₂)₂— | —CH₂—CH₂—CH₂OH | —CH₂—CH₂—CH₂OH | OH | H | CH₃ | H |
| —(CH₂)₂— | —CH₂—C₆H₅ | —CH₂—C₆H₅ | OH | H | CH₃ | H |
| —(CH₂)₂— | —CH₂—CH₂—C₆H₅ | —CH₂—CH₂—C₆H₅ | OH | H | CH₃ | H |
| —(CH₂)₂— | H | cyclopentyl | OH | H | CH₃ | H |
| —(CH₂)₂— | H | cyclohexyl | OH | H | CH₃ | H |
| —(CH₂)₂— | H | cycloheptyl | OH | H | CH₃ | H |
| —(CH₂)₂— | H | cyclohexyl-COOH | OH | H | CH₃ | H |
| —(CH₂)₂— | H | cyclohexyl-CH₂—COOH | OH | H | CH₃ | H |

TABLE IVB-continued

| R₁, R₂ | R₃ | R₄ | R₅ | R₆ | R₇ | R₈ |
|---|---|---|---|---|---|---|
| —(CH₂)₂— | | cyclohexyl–CH₂–CH₂–COOH | OH | H | CH₃ | H |
| —(CH₂)₂— | | cyclopentyl–COOH | OH | H | CH₃ | H |
| —(CH₂)₂— | | cyclopentyl(COOH)(OH) | OH | H | CH₃ | H |
| —(CH₂)₃— | H | H | OH | H | CH₃ | H |
| —(CH₂)₃— | H | CH₃ | OH | H | CH₃ | H |
| —(CH₂)₃— | H | C₂H₅ | OH | H | CH₃ | H |
| —(CH₂)₃— | H | n-C₃H₇ | OH | H | CH₃ | H |
| —(CH₂)₃— | H | n-C₄H₉ | OH | H | CH₃ | H |
| —(CH₂)₃— | H | i-C₃H₇ | OH | H | CH₃ | H |
| —(CH₂)₃— | H | i-C₄H₉ | OH | H | CH₃ | H |
| —(CH₂)₃— | H | n-C₅H₁₁ | OH | H | CH₃ | H |
| —(CH₂)₃— | H | n-C₆H₁₃ | OH | H | CH₃ | H |
| —(CH₂)₃— | H | C₂H₄OH | OH | H | CH₃ | H |
| —(CH₂)₃— | H | —CH₂—CH(OH)—CH₃ | OH | H | CH₃ | H |
| —(CH₂)₃— | H | —CH₂—CH₂—CH₂OH | OH | H | CH₃ | H |
| —(CH₂)₃— | H | —CH₂—CH₂—N(CH₃)₂ | OH | H | CH₃ | H |
| —(CH₂)₃— | H | —CH₂—CH₂—N(C₂H₅)₂ | OH | H | CH₃ | H |
| —(CH₂)₃— | H | —CH₂—CH₂—N(C₄H₉)₂ | OH | H | CH₃ | H |
| —(CH₂)₃— | H | —CH₂—CH₂—CH₂—N(CH₃)₂ | OH | H | CH₃ | H |
| —(CH₂)₃— | H | —CH₂—CH₂—CH₂—N(C₂H₅)₂ | OH | H | CH₃ | H |
| —(CH₂)₃— | H | —CH₂—CON(CH₃)₂ | OH | H | CH₃ | H |
| —(CH₂)₃— | H | —CH₂—CH₂—CON(CH₃)₂ | OH | H | CH₃ | H |
| —(CH₂)₃— | H | —CH₂—CH₂—CON(C₂H₅)₂ | OH | H | CH₃ | H |
| —(CH₂)₃— | H | —CH₂—C₆H₅ | OH | H | CH₃ | H |
| —(CH₂)₃— | H | —CH₂—CH₂—C₆H₅ | OH | H | CH₃ | H |
| —(CH₂)₃— | H | —CH₂—CH₂—N(pyrrolidino) | OH | H | CH₃ | H |
| —(CH₂)₃— | H | —CH₂—CH₂—N(morpholino) | OH | H | CH₃ | H |
| —(CH₂)₃— | H | —CH₂—CH₂—N(piperidino) | OH | H | CH₃ | H |

TABLE IVB-continued

| R₁, R₂ | R₃ | R₄ | R₅ | R₆ | R₇ | R₈ |
|---|---|---|---|---|---|---|
| —(CH₂)₃— | H | —CH₂—CH₂—N(piperazine)N—CH₃ | OH | H | CH₃ | H |
| —(CH₂)₃— | n-C₅H₁₁ | n-C₅H₁₁ | OH | H | CH₃ | H |
| —(CH₂)₃— | n-C₆H₁₃ | n-C₆H₁₃ | OH | H | CH₃ | H |
| —(CH₂)₃— | i-C₃H₇ | i-C₃H₇ | OH | H | CH₃ | |
| —(CH₂)₃— | i-C₄H₉ | i-C₄H₉ | OH | H | CH₃ | H |
| —(CH₂)₃— | C₂H₄OH | C₂H₄OH | OH | H | CH₃ | H |
| —(CH₂)₃— | —CH₂—CH(OH)—CH₃ | —CH₂—CH(OH)—CH₃ | OH | H | CH₃ | H |
| —(CH₂)₃— | —CH₃ | C₂H₄OH | OH | H | CH₃ | H |
| —(CH₂)₃— | —CH₂—CH₂—CH₂OH | —CH₂—CH₂—CH₂OH | OH | H | CH₃ | H |
| —(CH₂)₃— | —CH₂—C₆H₅ | —CH₂—C₆H₅ | OH | H | CH₃ | H |
| —(CH₂)₃— | —CH₂—CH₂—C₆H₅ | —CH₂—CH₂—C₆H₅ | OH | H | CH₃ | H |
| —(CH₂)₃— | H | cyclopentyl | OH | H | CH₃ | H |
| —(CH₂)₃— | H | cyclohexyl | OH | H | CH₃ | H |
| —(CH₂)₃— | H | cyclooctyl | OH | H | CH₃ | H |
| —(CH₂)₃— | | cyclohexyl-COOH | OH | H | CH₃ | H |
| —(CH₂)₃— | | cyclohexyl-CH₂-COOH | OH | H | CH₃ | H |
| —(CH₂)₃— | | cyclohexyl-CH₂-CH₂-COOH | OH | H | CH₃ | H |
| —(CH₂)₃— | | cyclopentyl-COOH | OH | H | CH₃ | H |
| —(CH₂)₃— | | cyclopentyl(COOH)(OH) | OH | H | CH₃ | H |

TABLE VA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | H | OH | H | Cl |
| $CH_3$ | $CH_3$ | $C_2H_5$ | H | OH | H | Cl |
| $CH_3$ | $C_2H_5$ | $C_2H_5$ | H | OH | H | Cl |
| $CH_3$ | $n$-$C_3H_7$ | $n$-$C_3H_7$ | H | OH | H | Cl |
| $CH_3$ | $n$-$C_4H_9$ | $n$-$C_4H_9$ | H | OH | H | Cl |
| $CH_3$ | H | $CH_2$—COOH | H | OH | H | Cl |
| $CH_3$ | H | $CH_2$—$COOC_2H_5$ | H | OH | H | Cl |
| $CH_3$ | H | $CH_3$—CH—COOH | H | OH | H | Cl |
| $CH_3$ | H | $CH_3$—CH—$COOC_2H_5$ | H | OH | H | Cl |
| $CH_3$ | H | —$CH_2$—$CH_2$—COOH | H | OH | H | Cl |
| $CH_3$ | H | —$CH_2$—$CH_2$—$COOC_2H_5$ | H | OH | H | Cl |
| $CH_3$ | H | —$(CH_2)_4$—CH—COOH, $NH_2$ | H | OH | H | Cl |
| $CH_3$ | \multicolumn{2}{l|}{cyclopentyl} | H | OH | H | Cl |
| $CH_3$ | \multicolumn{2}{l|}{cyclohexyl} | H | OH | H | Cl |
| $CH_3$ | \multicolumn{2}{l|}{tetrahydropyranyl (O)} | H | OH | H | Cl |
| $CH_3$ | \multicolumn{2}{l|}{piperidinyl (NH)} | H | OH | H | Cl |
| $CH_3$ | \multicolumn{2}{l|}{N—$CH_3$ piperidinyl} | H | OH | H | Cl |
| $CH_3$ | \multicolumn{2}{l|}{N—$C_2H_5$ piperidinyl} | H | OH | H | Cl |
| $CH_3$ | \multicolumn{2}{l|}{N—$C_2H_5$OH piperidinyl} | H | OH | H | Cl |
| $C_2H_5$ | $CH_3$ | $CH_3$ | H | OH | H | Cl |
| $C_2H_5$ | $CH_3$ | $C_2H_5$ | H | OH | H | Cl |
| $C_2H_5$ | $C_2H_5$ | $C_2H_5$ | H | OH | H | Cl |
| $C_2H_5$ | $n$-$C_3H_7$ | $n$-$C_3H_7$ | H | OH | H | Cl |
| $C_2H_5$ | $n$-$C_4H_9$ | $n$-$C_4H_9$ | H | OH | H | Cl |
| $C_2H_5$ | H | $CH_2$—COOH | H | OH | H | Cl |

TABLE VA-continued

| $R_1, R_2$ | $R_3$ | $R_4$ | $R_5$ | $R_6$ | $R_7$ | $R_8$ |
|---|---|---|---|---|---|---|
| $C_2H_5$ | H | $CH_2-COOC_2H_5$ | H | OH | H | Cl |
| $C_2H_5$ | H | $CH_3-CH-COOH$<br>$\quad\quad\vert$ | H | OH | H | Cl |
| $C_2H_5$ | H | $CH_3-CH-COOC_2H_5$<br>$\quad\quad\vert$ | H | OH | H | Cl |
| $C_2H_5$ | H | $-CH_2-CH_2-COOH$ | H | OH | H | Cl |
| $C_2H_5$ | H | $-CH_2-CH_2-COOC_2H_5$ | H | OH | H | Cl |
| $C_2H_5$ | H | $-(CH_2)_4-CH-COOH$<br>$\quad\quad\quad\quad\vert$<br>$\quad\quad\quad\quad NH_2$ | H | OH | H | Cl |
| $C_2H_5$ |  | | H | OH | H | Cl |
| $C_2H_5$ |  | | H | OH | H | Cl |
| $C_2H_5$ |  | | H | OH | H | Cl |
| $C_2H_5$ |  | | H | OH | H | Cl |
| $C_2H_5$ | 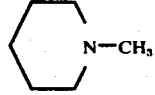 | | H | OH | H | Cl |
| $C_2H_5$ | 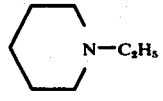 | | H | OH | H | Cl |
| $C_2H_5$ | 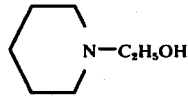 | | H | OH | H | Cl |
| $n-C_3H_7$ | $CH_3$ | $CH_3$ | H | OH | H | Cl |
| $n-C_3H_7$ | $CH_3$ | $C_2H_5$ | H | OH | H | Cl |
| $n-C_3H_7$ | $C_2H_5$ | $C_2H_5$ | H | OH | H | Cl |
| $n-C_3H_7$ | $n-C_3H_7$ | $n-C_3H_7$ | H | OH | H | Cl |
| $n-C_3H_7$ | $n-C_4H_9$ | $n-C_4H_9$ | H | OH | H | Cl |
| $n-C_3H_7$ | H | $CH_2-COOH$ | H | OH | H | Cl |
| $n-C_3H_7$ | H | $CH_2-COOC_2H_5$ | H | OH | H | Cl |
| $n-C_3H_7$ | H | $CH_3-CH-COOH$<br>$\quad\quad\vert$ | H | OH | H | Cl |
| $n-C_3H_7$ | H | $CH_3-CH-COOC_2H_5$<br>$\quad\quad\vert$ | H | OH | H | Cl |
| $n-C_3H_7$ | H | $-CH_2-CH_2-COOH$ | H | OH | H | Cl |

TABLE VA-continued

| R₁, R₂ | R₃ | R₄ | R₅ | R₆ | R₇ | R₈ |
|---|---|---|---|---|---|---|
| n-C₃H₇ | H | —CH₂—CH₂—COOC₂H₅ | H | OH | H | Cl |
| n-C₃H₇ | H | —(CH₂)₄—CH(NH₂)—COOH | H | OH | H | Cl |
| n-C₃H₇ | { cyclopentyl } | | H | OH | H | Cl |
| n-C₃H₇ | { cyclohexyl } | | H | OH | H | Cl |
| n-C₃H₇ | { tetrahydropyranyl (O) } | | H | OH | H | Cl |
| n-C₃H₇ | { piperidinyl (NH) } | | H | OH | H | Cl |
| n-C₃H₇ | { N—CH₃ piperidinyl } | | H | OH | H | Cl |
| n-C₃H₇ | { N—C₂H₅ piperidinyl } | | H | OH | H | Cl |
| n-C₃H₇ | { N—C₂H₅OH piperidinyl } | | H | OH | H | Cl |
| n-C₄H₉ | CH₃ | CH₃ | H | OH | H | Cl |
| n-C₄H₉ | CH₃ | C₂H₅ | H | OH | H | Cl |
| n-C₄H₉ | C₂H₅ | C₂H₅ | H | OH | H | Cl |
| n-C₄H₉ | n-C₃H₇ | n-C₃H₇ | H | OH | H | Cl |
| n-C₄H₉ | n-C₄H₉ | n-C₄H₉ | H | OH | H | Cl |
| n-C₄H₉ | H | CH₂—COOH | H | OH | H | Cl |
| n-C₄H₉ | H | CH₂—COOC₂H₅ | H | OH | H | Cl |
| n-C₄H₉ | H | CH₃—CH(COOH)— | H | OH | H | Cl |
| n-C₄H₉ | H | CH₃—CH(COOC₂H₅)— | H | OH | H | Cl |
| n-C₄H₉ | H | —CH₂—CH₂—COOH | H | OH | H | Cl |
| n-C₄H₉ | H | —CH₂—CH₂—COOC₂H₅ | H | OH | H | Cl |
| n-C₄H₉ | H | —(CH₂)₄—CH(NH₂)—COOH | H | OH | H | Cl |

TABLE VA-continued

| R₁, R₂ | R₃ | R₄ | R₅ | R₆ | R₇ | R₈ |
|---|---|---|---|---|---|---|
| n-C₄H₉ | |  | H | OH | H | Cl |
| n-C₄H₉ | |  | H | OH | H | Cl |
| n-C₄H₉ | | 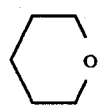 | H | OH | H | Cl |
| n-C₄H₉ | | 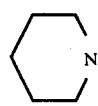 | H | OH | H | Cl |
| n-C₄H₉ | | 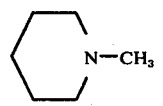 | H | OH | H | Cl |
| n-C₄H₉ | | 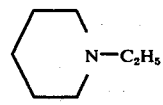 | H | OH | H | Cl |
| n-C₄H₉ | | 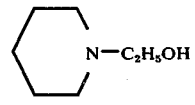 | H | OH | H | Cl |

TABLE VB

| R₁, R₂ | R₃ | R₄ | R₅ | R₆ | R₇ | R₈ |
|---|---|---|---|---|---|---|
| CH₃ | H | H | H | OH | H | Cl |
| CH₃ | H | CH₃ | H | OH | H | Cl |
| CH₃ | H | C₂H₅ | H | OH | H | Cl |
| CH₃ | H | n-C₃H₇ | H | OH | H | Cl |
| CH₃ | H | n-C₄H₉ | H | OH | H | Cl |
| CH₃ | H | i-C₃H₇ | H | OH | H | Cl |
| CH₃ | H | i-C₄H₉ | H | OH | H | Cl |
| CH₃ | H | n-C₅H₁₁ | H | OH | H | Cl |
| CH₃ | H | n-C₆H₁₃ | H | OH | H | Cl |
| CH₃ | H | C₂H₄OH | H | OH | H | Cl |
| CH₃ | H | —CH₂—CH(OH)—CH₃ | H | OH | H | Cl |
| CH₃ | H | —CH₂—CH₂—CH₂OH | H | OH | H | Cl |
| CH₃ | H | —CH₂—CH₂—N(CH₃)₂ | H | OH | H | Cl |
| CH₃ | H | —CH₂—CH₂—N(C₂H₅)₂ | H | OH | H | Cl |
| CH₃ | H | —CH₂—CH₂—N(C₄H₉)₂ | H | OH | H | Cl |
| CH₃ | H | —CH₂—CH₂—CH₂—N(CH₃)₂ | H | OH | H | Cl |
| CH₃ | H | —CH₂—CH₂—CH₂—N(C₂H₅)₂ | H | OH | H | Cl |
| CH₃ | H | —CH₂—CON(CH₃)₂ | H | OH | H | Cl |
| CH₃ | H | —CH₂—CH₂—CON(CH₃)₂ | H | OH | H | Cl |

TABLE VB-continued

| R₁, R₂ | R₃ | R₄ | R₅ | R₆ | R₇ | R₈ |
|---|---|---|---|---|---|---|
| $CH_3$ | H | $-CH_2-CON(C_2H_5)_2$ | H | OH | H | Cl |
| $CH_3$ | H | $-CH_2-C_6H_5$ | H | OH | H | Cl |
| $CH_3$ | H | $-CH_2-CH_2-C_6H_5$ | H | OH | H | Cl |
| $CH_3$ | H | $-CH-CH_2-N\underset{\phantom{x}}{\underbrace{\phantom{xxx}}}$ (pyrrolidine) | H | OH | H | Cl |
| $CH_3$ | H | $-CH_2-CH_2-N\underset{\phantom{x}}{\underbrace{\phantom{xxx}}}O$ (morpholine) | H | OH | H | Cl |
| $CH_3$ | H | $-CH_2-CH_2-N\underset{\phantom{x}}{\underbrace{\phantom{xxx}}}$ (piperidine) | H | OH | H | Cl |
| $CH_3$ | H | $-CH_2-CH_2-N\underset{\phantom{x}}{\underbrace{\phantom{xxx}}}N-CH_3$ (N-methylpiperazine) | H | OH | H | Cl |
| $CH_3$ | $n\text{-}C_5H_{11}$ | $n\text{-}C_5H_{11}$ | H | OH | H | Cl |
| $CH_3$ | $n\text{-}C_6H_{13}$ | $n\text{-}C_6H_{13}$ | H | OH | H | Cl |
| $CH_3$ | $i\text{-}C_3H_7$ | $i\text{-}C_3H_7$ | H | OH | H | Cl |
| $CH_3$ | $i\text{-}C_4H_9$ | $i\text{-}C_4H_9$ | H | OH | H | Cl |
| $CH_3$ | $C_2H_4OH$ | $C_2H_4OH$ | H | OH | H | Cl |
| $CH_3$ | $-CH_2-CH(OH)-CH_3$ | $-CH_2-CH(OH)-CH_3$ | H | OH | H | Cl |
| $CH_3$ | $-CH_3$ | $C_2H_4OH$ | H | OH | H | Cl |
| $CH_3$ | $-CH_2-CH_2-CH_2OH$ | $-CH_2-CH_2-CH_2OH$ | H | OH | H | Cl |
| $CH_3$ | $-CH_2-C_6H_5$ | $-CH_2-C_6H_5$ | H | OH | H | Cl |
| $CH_3$ | $-CH_2-CH_2-C_6H_5$ | $-CH_2-CH_2-C_6H_5$ | H | OH | H | Cl |
| $CH_3$ | H | cyclopentyl | H | OH | H | Cl |
| $CH_3$ | H | cyclohexyl | H | OH | H | Cl |
| $CH_3$ | H | cycloheptyl | H | OH | H | Cl |
| $CH_3$ | | cyclohexyl-COOH | H | OH | H | Cl |
| $CH_3$ | | cyclohexyl-$CH_2$-COOH | H | OH | H | Cl |

TABLE VB-continued

| R₁, R₂ | R₃ | R₄ | R₅ | R₆ | R₇ | R₈ |
|---|---|---|---|---|---|---|
| CH₃ | | cyclohexyl-CH₂-CH₂-COOH | H | OH | H | Cl |
| CH₃ | | cyclopentyl-COOH | H | OH | H | Cl |
| CH₃ | | cyclopentyl(COOH)(OH) | H | OH | H | Cl |
| C₂H₅ | H | H | H | OH | H | Cl |
| C₂H₅ | H | CH₃ | H | OH | H | Cl |
| C₂H₅ | H | C₂H₅ | H | OH | H | Cl |
| C₂H₅ | H | n-C₃H₇ | H | OH | H | Cl |
| C₂H₅ | H | n-C₄H₉ | H | OH | H | Cl |
| C₂H₅ | H | i-C₃H₇ | H | OH | H | Cl |
| C₂H₅ | H | i-C₄H₉ | H | OH | H | Cl |
| C₂H₅ | H | n-C₅H₁₁ | H | OH | H | Cl |
| C₂H₅ | H | n-C₆H₁₃ | H | OH | H | Cl |
| C₂H₅ | H | C₂H₄OH | H | OH | H | Cl |
| C₂H₅ | H | —CH₂—CH(OH)—CH₃ | H | OH | H | Cl |
| C₂H₅ | H | —CH₂—CH₂—CH₂OH | H | OH | H | Cl |
| C₂H₅ | H | —CH₂—CH₂—N(CH₃)₂ | H | OH | H | Cl |
| C₂H₅ | H | —CH₂—CH₂—N(C₂H₅)₂ | H | OH | H | Cl |
| C₂H₅ | H | —CH₂—CH₂—N(C₄H₉)₂ | H | OH | H | Cl |
| C₂H₅ | H | —CH₂—CH₂—CH₂—N(CH₃)₂ | H | OH | H | Cl |
| C₂H₅ | H | —CH₂—CH₂—CH₂—N(C₂H₅)₂ | H | OH | H | Cl |
| C₂H₅ | H | —CH₂—CON(CH₃)₂ | H | OH | H | Cl |
| C₂H₅ | H | —CH₂—CH₂—CON(CH₃)₂ | H | OH | H | Cl |
| C₂H₅ | H | —CH₂—CON(C₂H₅)₂ | H | OH | H | Cl |
| C₂H₅ | H | —CH₂—C₆H₅ | H | OH | H | Cl |
| C₂H₅ | H | —CH₂—CH₂—C₆H₅ | H | OH | H | Cl |
| C₂H₅ | H | —CH₂—CH₂—N(pyrrolidinyl) | H | OH | H | Cl |
| C₂H₅ | H | —CH₂—CH₂—N(morpholinyl) | H | OH | H | Cl |
| C₂H₅ | H | —CH₂—CH₂—N(piperidinyl) | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| $C_2H_5$ | H | $-CH_2-CH_2-N\underset{\phantom{x}}{\overset{\phantom{x}}{\diagup\!\!\!\diagdown}}N-CH_3$ | H | OH | H | Cl |
| $C_2H_5$ | n-$C_5H_{11}$ | n-$C_5H_{11}$ | H | OH | H | Cl |
| $C_2H_5$ | n-$C_6H_{13}$ | n-$C_6H_{13}$ | H | OH | H | Cl |
| $C_2H_5$ | i-$C_3H_7$ | i-$C_3H_7$ | H | OH | H | Cl |
| $C_2H_5$ | i-$C_4H_9$ | i-$C_4H_9$ | H | OH | H | Cl |
| $C_2H_5$ | $C_2H_4OH$ | $C_2H_4OH$ | H | OH | H | Cl |
| $C_2H_5$ | $-CH_2-\underset{OH}{CH}-CH_3$ | $-CH_2-\underset{OH}{CH}-CH_3$ | H | OH | H | Cl |
| $C_2H_5$ | $-CH_3$ | $C_2H_4OH$ | H | OH | H | Cl |
| $C_2H_5$ | $-CH_2-CH_2-CH_2OH$ | $-CH_2-CH_2-CH_2OH$ | H | OH | H | Cl |
| $C_2H_5$ | $-CH_2-C_6H_5$ | $-CH_2-C_6H_5$ | H | OH | H | Cl |
| $C_2H_5$ | $-CH_2-CH_2-C_6H_5$ | $-CH_2-CH_2-C_6H_5$ | H | OH | H | Cl |
| $C_2H_5$ | H | cyclopentyl | H | OH | H | Cl |
| $C_2H_5$ | H | cyclohexyl | H | OH | H | Cl |
| $C_2H_5$ | H | cyclooctyl | H | OH | H | Cl |
| $C_2H_5$ | | cyclohexyl-COOH | H | OH | H | Cl |
| $C_2H_5$ | | cyclohexyl-$CH_2$-COOH | H | OH | H | Cl |
| $C_2H_5$ | | cyclohexyl-$CH_2$-$CH_2$-COOH | H | OH | H Cl | |
| $C_2H_5$ | | cyclopentyl-COOH | H | OH | H | Cl |
| $C_2H_5$ | | cyclopentyl(COOH)(OH) | H | OH | H | Cl |
| n-$C_3H_7$ | H | H | H | OH | H | Cl |
| n-$C_3H_7$ | H | $CH_3$ | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| n-$C_3H_7$ | H | $C_2H_5$ | H | OH | H | Cl |
| n-$C_3H_7$ | H | n-$C_3H_7$ | H | OH | H | Cl |
| n-$C_3H_7$ | H | n-$C_4H_9$ | H | OH | H | Cl |
| n-$C_3H_7$ | H | i-$C_3H_7$ | H | OH | H | Cl |
| n-$C_3H_7$ | H | i-$C_4H_9$ | H | OH | H | Cl |
| n-$C_3H_7$ | H | n-$C_5H_{11}$ | H | OH | H | Cl |
| n-$C_3H_7$ | H | n-$C_6H_{13}$ | H | OH | H | Cl |
| n-$C_3H_7$ | H | $C_2H_4OH$ | H | OH | H | Cl |
| n-$C_3H_7$ | H | —$CH_2$—CH(OH)—$CH_3$ | H | OH | H | Cl |
| n-$C_3H_7$ | H | —$CH_2$—$CH_2$—$CH_2OH$ | H | OH | H | Cl |
| n-$C_3H_7$ | H | —$CH_2$—$CH_2$—$N(CH_3)_2$ | H | OH | H | Cl |
| n-$C_3H_7$ | H | —$CH_2$—$CH_2$—$N(C_2H_5)_2$ | H | OH | H | Cl |
| n-$C_3H_7$ | H | —$CH_2$—$CH_2$—$N(C_4H_9)_2$ | H | OH | H | Cl |
| n-$C_3H_7$ | H | —$CH_2$—$CH_2$—$CH_2$—$N(CH_3)_2$ | H | OH | H | Cl |
| n-$C_3H_7$ | H | —$CH_2$—$CH_2$—$CH_2$—$N(C_2H_5)_2$ | H | OH | H | Cl |
| n-$C_3H_7$ | H | —$CH_2$—$CON(CH_3)_2$ | H | OH | H | Cl |
| n-$C_3H_7$ | H | —$CH_2$—$CH_2$—$CON(CH_3)_2$ | H | OH | H | Cl |
| n-$C_3H_7$ | H | —$CH_2$—$CON(C_2H_5)_2$ | H | OH | H | Cl |
| n-$C_3H_7$ | H | —$CH_2$—$C_6H_5$ | H | OH | H | Cl |
| n-$C_3H_7$ | H | —$CH_2$—$CH_2$—$C_6H_5$ | H | OH | H | Cl |
| n-$C_3H_7$ | H | —$CH_2$—$CH_2$—N(pyrrolidinyl) 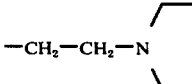 | H | OH | H | Cl |
| n-$C_3H_7$ | H | —$CH_2$—$CH_2$—N(morpholinyl) 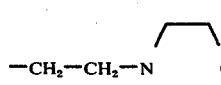 | H | OH | H | Cl |
| n-$C_3H_7$ | H | —$CH_2$—$CH_2$—N(piperidinyl)  | H | OH | H | Cl |
| n-$C_3H_7$ | H | —$CH_2$—$CH_2$—N(4-methylpiperazinyl)  | H | OH | H | Cl |
| n-$C_3H_7$ | n-$C_5H_{11}$ | n-$C_5H_{11}$ | H | OH | H | Cl |
| n-$C_3H_7$ | n-$C_6H_{13}$ | n-$C_6H_{13}$ | H | OH | H | Cl |
| n-$C_3H_7$ | i-$C_3H_7$ | i-$C_3H_7$ | H | OH | H | Cl |
| n-$C_3H_7$ | i-$C_4H_9$ | i-$C_4H_9$ | H | OH | H | Cl |
| n-$C_3H_7$ | $C_2H_4OH$ | $C_2H_4OH$ | H | OH | H | Cl |
| n-$C_3H_7$ | —$CH_2$—CH(OH)—$CH_3$ | —$CH_2$—CH(OH)—$CH_3$ | H | OH | H | Cl |
| n-$C_3H_7$ | —$CH_3$ | $C_2H_4OH$ | H | OH | H | Cl |
| n-$C_3H_7$ | —$CH_2$—$CH_2$—$CH_2OH$ | —$CH_2$—$CH_2$—$CH_2OH$ | H | OH | H | Cl |
| n-$C_3H_7$ | —$CH_2$—$C_6H_5$ | —$CH_2$—$C_6H_5$ | H | OH | H | Cl |
| n-$C_3H_7$ | —$CH_2$—$CH_2$—$C_6H_5$ | —$CH_2$—$CH_2$—$C_6H_5$ | H | OH | H | Cl |

TABLE VB-continued

| R₁, R₂ | R₃ | R₄ | R₅ | R₆ | R₇ | R₈ |
|---|---|---|---|---|---|---|
| n-C₃H₇ | H |  cyclopentyl | H | OH | H | Cl |
| n-C₃H₇ | H |  cyclohexyl | H | OH | H | Cl |
| n-C₃H₇ | H |  cyclooctyl | H | OH | H | Cl |
| n-C₃H₇ | H | 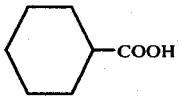 cyclohexyl-COOH | H | OH | H | Cl |
| n-C₃H₇ | H | 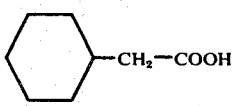 cyclohexyl-CH₂-COOH | H | OH | H | Cl |
| n-C₃H₇ | H | 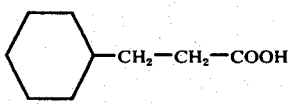 cyclohexyl-CH₂-CH₂-COOH | H | OH | H | Cl |
| n-C₃H₇ | H | 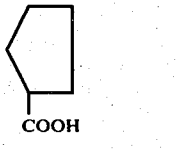 cyclopentyl-COOH | H | OH | H | Cl |
| n-C₃H₇ | H | 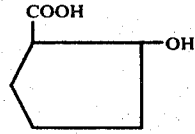 COOH, OH cyclopentyl | H | OH | H | Cl |
| n-C₄H₉ | H | H | H | OH | H | Cl |
| n-C₄H₉ | H | CH₃ | H | OH | H | Cl |
| n-C₄H₉ | H | C₂H₅ | H | OH | H | Cl |
| n-C₄H₉ | H | n-C₃H₇ | H | OH | H | Cl |
| n-C₄H₉ | H | n-C₄H₉ | H | OH | H | Cl |
| n-C₄H₉ | H | i-C₃H₇ | H | OH | H | Cl |
| n-C₄H₉ | H | i-C₄H₉ | H | OH | H | Cl |
| n-C₄H₉ | H | n-C₅H₁₁ | H | OH | H | Cl |
| n-C₄H₉ | H | n-C₆H₁₃ | H | OH | H | Cl |
| n-C₄H₉ | H | C₂H₄OH | H | OH | H | Cl |
| n-C₄H₉ | H | —CH₂—CH(OH)—CH₃ | H | OH | H | Cl |
| n-C₄H₉ | H | —CH₂—CH₂—CH₂OH | H | OH | H | Cl |
| n-C₄H₉ | H | —CH₂—CH₂—N(CH₃)₂ | H | OH | H | Cl |
| n-C₄H₉ | H | —CH₂—CH₂—N(C₂H₅)₂ | H | OH | H | Cl |
| n-C₄H₉ | H | —CH₂—CH₂—N(C₄H₉)₂ | H | OH | H | Cl |
| n-C₄H₉ | H | —CH₂—CH₂—CH₂—N(CH₃)₂ | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| n-$C_4H_9$ | H | —$CH_2$—$CH_2$—$CH_2$—$N(C_2H_5)_2$ | H | OH | H | Cl |
| n-$C_4H_9$ | H | —$CH_2$—$CON(CH_3)_2$ | H | OH | H | Cl |
| n-$C_4H_9$ | H | —$CH_2$—$CH_2$—$CON(CH_3)_2$ | H | OH | H | Cl |
| n-$C_4H_9$ | H | —$CH_2$—$CON(C_2H_5)_2$ | H | OH | H | Cl |
| n-$C_4H_9$ | H | —$CH_2$—$C_6H_5$ | H | OH | H | Cl |
| n-$C4H_9$ | H | —$CH_2$—$CH_2$—$C_6H_5$ | H | OH | H | Cl |
| n-$C_4H_9$ | H | —$CH_2$—$CH_2$—N⟨pyrrolidine⟩ | H | OH | H | Cl |
| n-$C_4H_9$ | H | —$CH_2$—$CH_2$—N⟨morpholine⟩ | H | OH | H | Cl |
| n-$C_4H_9$ | H | —$CH_2$—$CH_2$—N⟨piperidine⟩ | H | OH | H | Cl |
| n-$C_4H_9$ | H | —$CH_2$—$CH_2$—N⟨N-methylpiperazine⟩ | H | OH | H | Cl |
| n-$C_4H_9$ | n-$C_5H_{11}$ | n-$C_5H_{11}$ | H | OH | H | Cl |
| n-$C_4H_9$ | n-$C_6H_{13}$ | n-$C_6H_{13}$ | H | OH | H | Cl |
| n-$C_4H_9$ | i-$C_3H_7$ | i-$C_3H_7$ | H | OH | H | Cl |
| n-$C_4H_9$ | i-$C_4H_9$ | i-$C_4H_9$ | H | OH | H | Cl |
| n-$C_4H_9$ | $C_2H_4OH$ | $C_2H_4OH$ | H | OH | H | Cl |
| n-$C_4H_9$ | —$CH_2$—CH(OH)—$CH_3$ | —$CH_2$—CH(OH)—$CH_3$ | H | OH | H | Cl |
| n-$C_4H_9$ | —$CH_3$ | $C_2H_4OH$ | H | OH | H | Cl |
| n-$C_4H_9$ | —$CH_2$—$CH_2$—$CH_2OH$ | —$CH_2$—$CH_2$—$CH_2OH$ | H | OH | H | Cl |
| n-$C_4H_9$ | —$CH_2$—$C_6H_5$ | —$CH_2$—$C_6H_5$ | H | OH | H | Cl |
| n-$C_4H_9$ | —$CH_2$—$CH_2$—$C_6H_5$ | —$CH_2$—$CH_2$—$C_6H_5$ | H | OH | H | Cl |
| n-$C_4H_9$ | H | cyclopentyl | H | OH | H | Cl |
| n-$C_4H_9$ | H | cyclohexyl | H | OH | H | Cl |
| n-$C_4H_9$ | H | cyclooctyl | H | OH | H | Cl |
| n-$C_4H_9$ | \{$R_3, R_4$ together: cyclohexyl-COOH\} | | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| n-$C_4H_9$ | | cyclohexyl-$CH_2$-COOH | H | OH | H | Cl |
| n-$C_4H_9$ | | cyclohexyl-$CH_2$-$CH_2$-COOH | H | OH | H | Cl |
| n-$C_4H_9$ | | cyclopentyl-COOH | H | OH | H | Cl |
| n-$C_4H_9$ | | 2-hydroxycyclopentane-COOH | H | OH | H | Cl |
| —$(CH_2)_2$— | H | H | H | OH | H | Cl |
| —$(CH_2)_2$— | H | $CH_3$ | H | OH | H | Cl |
| —$(CH_2)_2$— | H | $C_2H_5$ | H | OH | H | Cl |
| —$(CH_2)_2$— | H | n-$C_3H_7$ | H | OH | H | Cl |
| —$(CH_2)_2$— | H | n-$C_4H_9$ | H | OH | H | Cl |
| —$(CH_2)_2$— | H | i-$C_3H_7$ | H | OH | H | Cl |
| —$(CH_2)_2$— | H | i-$C_4H_9$ | H | OH | H | Cl |
| —$(CH_2)_2$— | H | n-$C_5H_{11}$ | H | OH | H | Cl |
| —$(CH_2)_2$— | H | n-$C_6H_{13}$ | H | OH | H | Cl |
| —$(CH_2)_2$— | H | $C_2H_4OH$ | H | OH | H | Cl |
| —$(CH_2)_2$— | H | —$CH_2$—CH(OH)—$CH_3$ | H | OH | H | Cl |
| —$(CH_2)_2$— | H | —$CH_2$—$CH_2$—$CH_2OH$ | H | OH | H | Cl |
| —$(CH_2)_2$— | H | —$CH_2$—$CH_2$—$N(CH_3)_2$ | H | OH | H | Cl |
| —$(CH_2)_2$— | H | —$CH_2$—$CH_2$—$N(C_2H_5)_2$ | H | OH | H | Cl |
| —$(CH_2)_2$— | H | —$CH_2$—$CH_2$—$N(C_4H_9)_2$ | H | OH | H | Cl |
| —$(CH_2)_2$— | H | —$CH_2$—$CH_2$—$CH_2$—$N(CH_3)_2$ | H | OH | H | Cl |
| —$(CH_2)_2$— | H | —$CH_2$—$CH_2$—$CH_2$—$N(C_2H_5)_2$ | H | OH | H | Cl |
| —$(CH_2)_2$— | H | —$CH_2$—$CON(CH_3)_2$ | H | OH | H | Cl |
| —$(CH_2)_2$— | H | —$CH_2$—$CH_2$—$CON(CH_3)_2$ | H | OH | H | Cl |
| —$(CH_2)_2$— | H | —$CH_2$—$CON(C_2H_5)_2$ | H | OH | H | Cl |
| —$(CH_2)_2$— | H | —$CH_2$—$C_6H_5$ | H | OH | H | Cl |
| —$(CH_2)_2$— | H | —$CH_2$—$CH_2$—$C_6H_5$ | H | OH | H | cl |
| —$(CH_2)_2$— | H | —$CH_2$—$CH_2$—N(pyrrolidinyl) | H | OH | H | Cl |
| —$(CH_2)_2$— | H | —$CH_2$—$CH_2$—N(morpholinyl) | H | OH | H | Cl |

TABLE VB-continued

| R₁, R₂ | R₃ | R₄ | R₅ | R₆ | R₇ | R₈ |
|---|---|---|---|---|---|---|
| —(CH₂)₂— | H | —CH₂—CH₂—N(piperidine) | H | OH | H | Cl |
| —(CH₂)₂— | H | —CH₂—CH₂—N(N-methylpiperazine)—N—CH₃ | H | OH | H | Cl |
| —(CH₂)₂— | n-C₅H₁₁ | n-C₅H₁₁ | H | OH | H | Cl |
| —(CH₂)₂— | n-C₆H₁₃ | n-C₆H₁₃ | H | OH | H | Cl |
| —(CH₂)₂— | i-C₃H₇ | i-C₃H₇ | H | OH | H | Cl |
| —(CH₂)₂— | i-C₄H₉ | i-C₄H₉ | H | OH | H | Cl |
| —(CH₂)₂— | C₂H₄OH | C₂H₄OH | H | OH | H | Cl |
| —(CH₂)₂— | —CH₂—CH(OH)—CH₃ | —CH₂—CH(OH)—CH₃ | H | OH | H | Cl |
| —(CH₂)₂— | —CH₃ | C₂H₄OH | H | OH | H | Cl |
| —(CH₂)₂— | —CH₂—CH₂—CH₂OH | —CH₂—CH₂—CH₂OH | H | OH | H | Cl |
| —(CH₂)₂— | —CH₂—C₆H₅ | —CH₂—C₆H₅ | H | OH | H | Cl |
| —(CH₂)₂— | —CH₂—CH₂—C₆H₅ | —CH₂—CH₂—C₆H₅ | H | OH | H | Cl |
| —(CH₂)₂— | H | cyclopentyl | H | OH | H | Cl |
| —(CH₂)₂— | H | cyclohexyl | H | OH | H | Cl |
| —(CH₂)₂— | H | cycloheptyl | H | OH | H | Cl |
| —(CH₂)₂— | \{cyclohexyl—COOH\} | | H | OH | H | Cl |
| —(CH₂)₂— | \{cyclohexyl—CH₂—COOH\} | | H | OH | H | Cl |
| —(CH₂)₂— | \{cyclohexyl—CH₂—CH₂—COOH\} | | H | OH | H | Cl |
| —(CH₂)₂— | \{cyclopentyl—COOH\} | | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| $-(CH_2)_2-$ | | 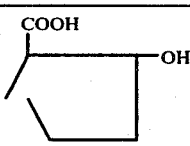 COOH, OH (cyclopentane) | H | OH | H | Cl |
| $-(CH_2)_3-$ | H | H | H | OH | H | Cl |
| $-(CH_2)_3-$ | H | $CH_3$ | H | OH | H | Cl |
| $-(CH_2)_3-$ | H | $C_2H_5$ | H | OH | H | Cl |
| $-(CH_2)_3-$ | H | $n-C_3H_7$ | H | OH | H | Cl |
| $-(CH_2)_3-$ | H | $n-C_4H_9$ | H | OH | H | Cl |
| $-(CH_2)_3-$ | H | $i-C_3H_7$ | H | OH | H | Cl |
| $-(CH_2)_3-$ | H | $i-C_4H_9$ | H | OH | H | Cl |
| $-(CH_2)_3-$ | H | $n-C_5H_{11}$ | H | OH | H | Cl |
| $-(CH_2)_3-$ | H | $n-C_6H_{13}$ | H | OH | H | Cl |
| $-(CH_2)_3-$ | H | $C_2H_4OH$ | H | OH | H | Cl |
| $-(CH_2)_3-$ | H | $-CH_2-CH(OH)-CH_3$ | H | OH | H | Cl |
| $-(CH_2)_3-$ | H | $-CH_2-CH_2-CH_2OH$ | H | OH | H | Cl |
| $-(CH_2)_3-$ | H | $-CH_2-CH_2-N(CH_3)_2$ | H | OH | H | Cl |
| $-(CH_2)_3-$ | H | $-CH_2-CH_2-N(C_2H_5)_2$ | H | OH | H | Cl |
| $-(CH_2)_3-$ | H | $-CH_2-CH_2-N(C_4H_9)_2$ | H | OH | H | Cl |
| $-(CH_2)_3-$ | H | $-CH_2-CH_2-CH_2-N(CH_3)_2$ | H | OH | H | Cl |
| $-(CH_2)_3-$ | H | $-CH_2-CH_2-CH_2-N(C_2H_5)_2$ | H | OH | H | Cl |
| $-(CH_2)_3-$ | H | $-CH_2-CON(CH_3)_2$ | H | OH | H | Cl |
| $-(CH_2)_3-$ | H | $-CH_2-CH_2-CON(CH_3)_2$ | H | OH | H | Cl |
| $-(CH_2)_3-$ | H | $-CH_2-CON(C_2H_5)_2$ | H | OH | H | Cl |
| $-(CH_2)_3-$ | H | $-CH_2-C_6H_5$ | H | OH | H | Cl |
| $-(CH_2)_3-$ | H | $-CH_2-CH_2-C_6H_5$ | H | OH | H | Cl |
| $-(CH_2)_3-$ | H | $-CH_2-CH_2-N$(pyrrolidinyl) | H | OH | H | Cl |
| $-(CH_2)_3-$ | H | $-CH_2-CH_2-N$(morpholinyl) 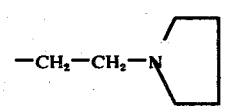 | H | OH | H | Cl |
| $-(CH_2)_3-$ | H | $-CH_2-CH_2-N$(piperidinyl) 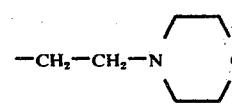 | H | OH | H | Cl |
| $-(CH_2)_3-$ | H | $-CH_2-CH_2-N(N-CH_3$-piperazinyl) 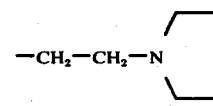 | H | OH | H | Cl |
| $-(CH_2)_3-$ | $n-C_5H_{11}$ | $n-C_5H_{11}$ | H | OH | H | Cl |
| $-(CH_2)_3-$ | $n-C_6H_{13}$ | $n-C_6H_{13}$ | H | OH | H | Cl |
| $-(CH_2)_3-$ | $i-C_3H_7$ | H | OH | H | Cl | |
| $-(CH_2)_3-$ | $i-C_4H_9$ | $i-C_4H_9$ | H | OH | H | Cl |
| $-(CH_2)_3-$ | $C_2H_4OH$ | $C_2H_4OH$ | H | OH | H | Cl |

TABLE VB-continued

| $R_1, R_2$ | $R_3$ | $R_4$ | $R_5$ | $R_6$ | $R_7$ | $R_8$ |
|---|---|---|---|---|---|---|
| $-(CH_2)_3-$ | $-CH_2-CH-CH_3$<br>$\quad\quad\quad\mid$<br>$\quad\quad\quad OH$ | $-CH_2-CH-CH_3$<br>$\quad\quad\quad\mid$<br>$\quad\quad\quad OH$ | H | OH | H | Cl |
| $-(CH_2)_3-$ | $-CH_3$ | $C_2H_4OH$ | H | OH | H | Cl |
| $-(CH_2)_3-$ | $-CH_2-CH_2-CH_2OH$ | $-CH_2-CH_2-CH_2OH$ | H | OH | H | Cl |
| $-(CH_2)_3-$ | $-CH_2-C_6H_5$ | $-CH_2-C_6H_5$ | H | OH | H | Cl |
| $-(CH_2)_3-$ | $-CH_2-CH_2-C_6H_5$ | $-CH_2-CH_2-C_{6S}$ | H | OH | H | Cl |
| $-(CH_2)_3-$ | H |  | H | OH | H | Cl |
| $-(CH_2)_3-$ | H |  | H | OH | H | Cl |
| $-(CH_2)_3-$ | H |  | H | OH | H | Cl |
| $-(CH_2)_3-$ | | 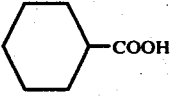 | H | OH | H | Cl |
| $-(CH_2)_3-$ | | 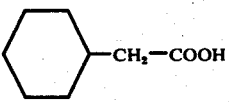 | H | OH | H | Cl |
| $-(CH_2)_3-$ | | 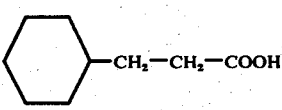 | H | OH | H | Cl |
| $-(CH_2)_3-$ |  | | H | OH | H | Cl |
| $-(CH_2)_3-$ | 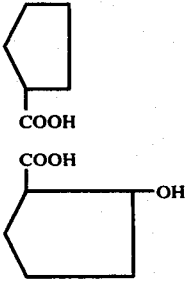 | | H | OH | H | Cl |

As further Examples are mentioned:

Table VIA

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | H | OH | H | H |
| $CH_3$ | $CH_3$ | $C_2H_5$ | H | OH | H | H |
| $CH_3$ | $C_2H_5$ | $C_2H_5$ | H | OH | H | H |
| $CH_3$ | $n-C_3H_7$ | $n-C_3H_7$ | H | OH | H | H |
| $CH_3$ | $n-C_4H_9$ | $n-C_4H_9$ | H | OH | H | H |
| $CH_3$ | H | $CH_2-COOH$ | H | OH | H | H |

Table VIA-continued

| R₁, R₂ | R₃ | R₄ | R₅ | R₆ | R₇ | R₈ |
|---|---|---|---|---|---|---|
| $CH_3$ | H | $CH_2-COOC_2H_5$ | H | OH | H | H |
| $CH_3$ | H | $CH_3-CH(-)-COOH$ | H | OH | H | H |
| $CH_3$ | H | $CH_3-CH(-)-COOC_2H_5$ | H | OH | H | H |
| $CH_3$ | H | $-CH_2-CH_2-COOH$ | H | OH | H | H |
| $CH_3$ | H | $-CH_2-CH_2-COOC_2H_5$ | H | OH | H | H |
| $CH_3$ | H | $-(CH_2)_4-CH(NH_2)-COOH$ | H | OH | H | H |
| $CH_3$ | \{ $R_3$ and $R_4$ together form cyclopentyl \} | | H | OH | H | H |
| $CH_3$ | \{ $R_3$ and $R_4$ together form cyclohexyl \} | | H | OH | H | H |
| $CH_3$ | \{ $R_3$ and $R_4$ together form tetrahydropyranyl (O) \} | | H | OH | H | H |
| $CH_3$ | \{ $R_3$ and $R_4$ together form piperidinyl (NH) \} | | H | OH | H | H |
| $CH_3$ | \{ $R_3$ and $R_4$ together form N-methylpiperidinyl \} | | H | OH | H | H |
| $CH_3$ | \{ $R_3$ and $R_4$ together form N-ethylpiperidinyl \} | | H | OH | H | H |
| $CH_3$ | \{ $R_3$ and $R_4$ together form N-(2-hydroxyethyl)piperidinyl \} | | H | OH | H | H |
| $C_2H_5$ | $CH_3$ | $CH_3$ | H | OH | H | H |
| $C_2H_5$ | $CH_3$ | $C_2H_5$ | H | OH | H | H |
| $C_2H_5$ | $C_2H_5$ | $C_2H_5$ | H | OH | H | H |
| $C_2H_5$ | $n-C_3H_7$ | $n-C_3H_7$ | H | OH | H | H |
| $C_2H_5$ | $n-C_4H_9$ | $n-C_4H_9$ | H | OH | H | H |
| $C_2H_5$ | H | $CH_2-COOH$ | H | OH | H | H |
| $C_2H_5$ | H | $CH_2-COOC_2H_5$ | H | OH | H | H |
| $C_2H_5$ | H | $CH_3-CH(-)-COOH$ | H | OH | H | H |
| $C_2H_5$ | H | $CH_3-CH(-)-COOC_2H_5$ | H | OH | H | H |
| $C_2H_5$ | H | $-CH_2-CH_2-COOH$ | H | OH | H | H |

Table VIA-continued

| R₁, R₂ | R₃ | R₄ | R₅ | R₆ | R₇ | R₈ |
|---|---|---|---|---|---|---|
| $C_2H_5$ | H | $-CH_2-CH_2-COOC_2H_5$ | H | OH | H | H |
| $C_2H_5$ | H | $-(CH_2)_4-\underset{\underset{NH_2}{\mid}}{CH}-COOH$ | H | OH | H | H |
| $C_2H_5$ | \multicolumn{2}{c|}{} | H | OH | H | H |
| $C_2H_5$ | \multicolumn{2}{c|}{} | H | OH | H | H |
| $C_2H_5$ | \multicolumn{2}{c|}{} | H | OH | H | H |
| $C_2H_5$ | \multicolumn{2}{c|}{} | H | OH | H | H |
| $C_2H_5$ | \multicolumn{2}{c|}{} | H | OH | H | H |
| $C_2H_5$ | \multicolumn{2}{c|}{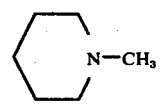} | H | OH | H | H |
| $C_2H_5$ | \multicolumn{2}{c|}{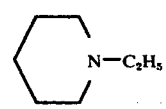} | H | OH | H | H |
| n-$C_3H_7$ | $CH_3$ | $CH_3$ | H | OH | H | H |
| n-$C_3H_7$ | $CH_3$ | $C_2H_5$ | H | OH | H | H |
| n-$C_3H_7$ | $C_2H_5$ | $C_2H_5$ | H | OH | H | H |
| n-$C_3H_7$ | n-$C_3H_7$ | n-$C_3H_7$ | H | OH | H | H |
| n-$C_3H_7$ | n-$C_4H_9$ | n-$C_4H_9$ | H | OH | H | H |
| n-$C_3H_7$ | H | $CH_2-COOH$ | H | OH | H | H |
| n-$C_3H_7$ | H | $CH_2-COOC_2H_5$ | H | OH | H | H |
| n-$C_3H_7$ | H | $CH_3-\underset{\mid}{CH}-COOH$ | H | OH | H | H |
| n-$C_3H_7$ | H | $CH_3-\underset{\mid}{CH}-COOC_2H_5$ | H | OH | H | H |
| n-$C_3H_7$ | H | $-CH_2-CH_2-COOH$ | H | OH | H | H |
| n-$C_3H_7$ | H | $-CH_2-CH_2-COOC_2H_5$ | H | OH | H | H |
| n-$C_3H_7$ | H | $-(CH_2)_4-\underset{\underset{NH_2}{\mid}}{CH}-COOH$ | H | OH | H | H |

Table VIA-continued

| $R_1, R_2$ | $R_3$ | $R_4$ | $R_5$ | $R_6$ | $R_7$ | $R_8$ |
|---|---|---|---|---|---|---|
| n-$C_3H_7$ |  | | H | OH | H | |
| n-$C_3H_7$ | 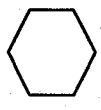 | | H | OH | H | H |
| n-$C_3H_7$ | 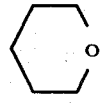 | | H | OH | H | H |
| n-$C_3H_7$ | 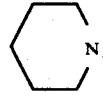 | | H | OH | H | H |
| n-$C_3H_7$ | 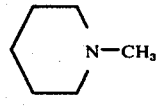 | | H | OH | H | H |
| n-$C_3H_7$ | 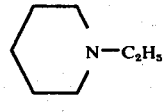 | | H | OH | H | H |
| n-$C_3H_7$ | 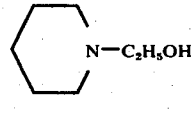 | | H | OH | H | H |
| n-$C_4H_9$ | $CH_3$ | $CH_3$ | H | OH | H | H |
| n-$C_4H_9$ | $CH_3$ | $C_2H_5$ | H | OH | H | H |
| n-$C_4H_9$ | $C_2H_5$ | $C_2H_5$ | H | OH | H | H |
| n-$C_4H_9$ | n-$C_3H_7$ | n-$C_3H_7$ | H | OH | H | H |
| n-$C_4H_9$ | n-$C_4H_9$ | n-$C_4H_9$ | H | OH | H | H |
| n-$C_4H_9$ | H | $CH_2$—COOH | H | OH | H | H |
| n-$C_4H_9$ | H | $CH_2$—$COOC_2H_5$ | H | OH | H | H |
| n-$C_4H_9$ | H | $CH_3$—CH—COOH | H | OH | H | H |
| n-$C_4H_9$ | H | $CH_3$—CH—$COOC_2H_5$ | H | OH | H | H |
| n-$C_4H_9$ | H | —$CH_2$—$CH_2$—COOH | H | OH | H | H |
| n-$C_4H_9$ | H | —$CH_2$—$CH_2$—$COOC_2H_5$ | H | OH | H | H |
| n-$C_4H_9$ | H | —$(CH_2)_4$—CH—COOH, $NH_2$ | H | OH | H | H |
| n-$C_4H_9$ |  | | H | OH | H | H |
| n-$C_4H_9$ |  | | H | OH | H | H |

Table VIA-continued

| $R_1, R_2$ | $R_3$ | $R_4$ | $R_5$ | $R_6$ | $R_7$ | $R_8$ |
|---|---|---|---|---|---|---|
| n-$C_4H_9$ | | tetrahydropyran (O in ring) | H | OH | H | H |
| n-$C_4H_9$ | | piperidine (NH in ring) | H | OH | H | H |
| n-$C_4H_9$ | | N-methylpiperidine (N–$CH_3$) | H | OH | H | H |
| n-$C_4H_9$ | | N-ethylpiperidine (N–$C_2H_5$) | H | OH | H | H |
| n-$C_4H_9$ | | N-(2-hydroxyethyl)piperidine (N–$C_2H_5OH$) | H | OH | H | H |

Table VIB

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $CH_3$ | H | H | H | —$N(CH_3)_2$ |
| $CH_3$ | $CH_3$ | $C_2H_5$ | H | H | H | —$N(CH_3)_2$ |
| $CH_3$ | $C_2H_5$ | $C_2H_5$ | H | H | H | —$N(CH_3)_2$ |
| $CH_3$ | n-$C_3H_7$ | n-$C_3H_7$ | H | H | H | —$N(CH_3)_2$ |
| $CH_3$ | n-$C_4H_9$ | n-$C_4H_9$ | H | H | H | —$N(CH_3)_2$ |
| $CH_3$ | H | $CH_2$—COOH | H | H | H | —$N(CH_3)_2$ |
| $CH_3$ | H | $CH_2$—$COOC_2H_5$ | H | H | H | —$N(CH_3)_2$ |
| $CH_3$ | H | $CH_3$—CH—COOH | H | H | H | —$N(CH_3)_2$ |
| $CH_3$ | H | $CH_3$—CH—$COOC_2H_5$ | H | H | H | —$N(CH_3)_2$ |
| $CH_3$ —$CH_2$—$CH_2$—$COOC_2H_5$ | H H | —$CH_2$—$CH_2$—COOH H | H H | H —$N(CH_3)_2$ | H | —$N(CH_3)_2$ |
| $CH_3$ | H | —$(CH_2)_4$—CH—COOH $\vert$ $NH_2$ | H | H | H | —$N(CH_3)_2$ |
| $CH_3$ | cyclopentyl | | H | H | H | —$N(CH_3)_2$ |
| $CH_3$ | cyclohexyl | | H | H | H | —$N(CH_3)_2$ |

Table VIB-continued

| $R_1, R_2$ | $R_3$ | $R_4$ | $R_5$ | $R_6$ | $R_7$ | $R_8$ |
|---|---|---|---|---|---|---|
| $CH_3$ | | tetrahydropyran ring | H | H | H | $-N(CH_3)_2$ |
| $CH_3$ | | piperidine ring (NH) | H | H | H | $-N(CH_3)_2$ |
| $CH_3$ | | piperidine ring (N-CH_3) | H | H | H | $-N(CH_3)_2$ |
| $CH_3$ | | piperidine ring (N-C_2H_5) | H | H | H | $-N(CH_3)_2$ |
| $CH_3$ | | piperidine ring (N-C_2H_5OH) | H | H | H | $-N(CH_3)_2$ |
| $C_2H_5$ | $CH_3$ | $CH_3$ | H | H | H | $-N(CH_3)_2$ |
| $C_2H_5$ | $CH_3$ | $C_2H_5$ | H | H | H | $-N(CH_3)_2$ |
| $C2H_5$ | $C_2H_5$ | $C_2H_5$ | H | H | H | $-N(CH_3)_2$ |
| $C_2H_5$ | $n-C_3H_7$ | $n-C_3H_7$ | H | H | H | $-N(CH_3)_2$ |
| $C_2H_5$ | $n-C_4H_9$ | $n-C_4H_9$ | H | H | H | $-N(CH_3)_2$ |
| $C_2H_5$ | H | $CH_2-COOH$ | H | H | H | $-N(CH_3)_2$ |
| $C_2H_5$ | H | $CH_2-COOC_2H_5$ | H | H | H | $-N(CH_3)_2$ |
| $C_2H_5$ | H | $CH_3-CH-COOH$ | H | H | H | $-N(CH_3)_2$ |
| $C_2H_5$ | H | $CH_3-CH-COOC_2H_5$ | H | H | H | $-N(CH_3)_2$ |
| $C_2H_5$ | H | $-CH_2-CH_2-COOH$ | H | H | H | $-N(CH_3)_2$ |
| $C_2H_5$ | H | $-CH_2-CH_2-COOC_2H_5$ | H | H | H | $-N(CH_3)_2$ |
| $C_2H_5$ | H | $-(CH_2)_4-CH(NH_2)-COOH$ | H | H | H | $-N(CH_3)_2$ |
| $C_2H_5$ | cyclopentane ring (R_3, R_4 joined) | | H | H | H | $-N(CH_3)_2$ |
| $C_2H_5$ | cyclohexane ring | | H | H | H | $-N(CH_3)_2$ |
| $C_2H_5$ | tetrahydropyran ring | | H | H | H | $-N(CH_3)_2$ |
| $C_2H_5$ | piperidine ring | | H | H | H | $-N(CH_3)_2$ |

Table VIB-continued

| R₁, R₂ | R₃ | R₄ | R₅ | R₆ | R₇ | R₈ |
|---|---|---|---|---|---|---|
| C₂H₅ | \multicolumn{2}{c}{N-methylpiperidine ring (R₃,R₄ = -(CH₂)₅- with N-CH₃)} | H | H | H | -N(CH₃)₂ |
| C₂H₅ | \multicolumn{2}{c}{N-ethylpiperidine ring (N-C₂H₅)} | H | H | H | -N(CH₃)₂ |
| C₂H₅ | \multicolumn{2}{c}{N-(2-hydroxyethyl)piperidine ring (N-C₂H₅OH)} | H | H | H | -N(CH₃)₂ |
| n-C₃H₇ | CH₃ | CH₃ | H | H | H | -N(CH₃)₂ |
| n-C₃H₇ | CH₃ | C₂H₅ | H | H | H | -N(CH₃)₂ |
| n-C₃H₇ | C₂H₅ | C₂H₅ | H | H | H | -N(CH₃)₂ |
| n-C₃H₇ | n-C₃H₇ | n-C₃H₇ | H | H | H | -N(CH₃)₂ |
| n-C₃H₇ | n-C₄H₉ | n-C₄H₉ | H | H | H | -N(CH₃)₂ |
| n-C₃H₇ | H | CH₂—COOH | H | H | H | -N(CH₃)₂ |
| n-C₃H₇ | H | CH₂—COOC₂H₅ | H | H | H | -N(CH₃)₂ |
| n-C₃H₇ | H | CH₃—CH(—)—COOH | H | H | H | -N(CH₃)₂ |
| n-C₃H₇ | H | CH₃—CH(—)—COOC₂H₅ | H | H | H | -N(CH₃)₂ |
| n-C₃H₇ | H | —CH₂—CH₂—COOH | H | H | H | -N(CH₃)₂ |
| n-C₃H₇ | H | —CH₂—CH₂—COOC₂H₅ | H | H | H | -N(CH₃)₂ |
| n-C₃H₇ | H | —(CH₂)₄—CH(NH₂)—COOH | H | H | H | -N(CH₃)₂ |
| n-C₃H₇ | \multicolumn{2}{c}{pyrrolidine ring (R₃,R₄ = -(CH₂)₄-)} | H | H | H | -N(CH₃)₂ |
| n-C₃H₇ | \multicolumn{2}{c}{hexamethyleneimine ring (R₃,R₄ = -(CH₂)₆-)} | H | H | H | -N(CH₃)₂ |
| n-C₃H₇ | \multicolumn{2}{c}{morpholine ring (O-containing)} | H | H | H | -N(CH₃)₂ |
| n-C₃H₇ | \multicolumn{2}{c}{piperidine ring (N-H)} | H | H | H | -N(CH₃)₂ |
| n-C₃H₇ | \multicolumn{2}{c}{N-methylpiperazine ring (N-CH₃)} | H | H | H | -N(CH₃)₂ |

Table VIB-continued

| R₁, R₂ | R₃ | R₄ | R₅ | R₆ | R₇ | R₈ |
|---|---|---|---|---|---|---|
| n-C₃H₇ | | piperidine-N—C₂H₅ | H | H | H | —N(CH₃)₂ |
| n-C₃H₇ | | piperidine-N—C₂H₅OH | H | H | H | —N(CH₃)₂ |
| n-C₄H₉ | CH₃ | CH₃ | H | H | H | —N(CH₃)₂ |
| n-C₄H₉ | CH₃ | C₂H₅ | H | H | H | —N(CH₃)₂ |
| n-C₄H₉ | C₂H₅ | C₂H₅ | H | H | H | —N(CH₃)₂ |
| n-C₄H₉ | n-C₃H₇ | n-C₃H₇ | H | H | H | —N(CH₃)₂ |
| n-C₄H₉ | n-C₄H₉ | n-C₄H₉ | H | H | H | —N(CH₃)₂ |
| n-C₄H₉ | H | CH₂—COOH | H | H | H | —N(CH₃)₂ |
| n-C₄H₉ | H | CH₂—COOC₂H₅ | H | H | H | —N(CH₃)₂ |
| n-C₄H₉ | H | CH₃—CH(—)—COOH | H | H | H | —N(CH₃)₂ |
| n-C₄H₉ | H | CH₃—CH(—)—COOC₂H₅ | H | H | H | —N(CH₃)₂ |
| n-C₄H₉ | H | —CH₂—CH₂—COOH | H | H | H | —N(CH₃)₂ |
| n-C₄H₉ | H | —CH₂—CH₂—COOC₂H₅ | H | H | H | —N(CH₃)₂ |
| n-C₄H₉ | H | —(CH₂)₄—CH(NH₂)—COOH | H | H | H | —(N(CH₃)₂ |
| n-C₄H₉ | cyclopentyl | | H | H | H | —N(CH₃)₂ |
| n-C₄H₉ | cyclohexyl | | H | H | H | —N(CH₃)₂ |
| n-C₄H₉ | tetrahydropyran-O | | H | H | H | —N(CH₃)₂ |
| n-C₄H₉ | piperidine-N | | H | H | H | —N(CH₃)₂ |
| N(CH₄H₉) | piperidine-N—CH₃ | | H | H | H | —N(CH₃)₂ |
| n-C₄H₉ | piperidine-N—C₂H₅ | | H | H | H | —N(CH₃)₂ |
| n-C₄₉ | piperidine-N—C₂H₅OH | | H | H | H | —N(CH₃)₂ |
| CH₃ | CH₃ | CH₃ | OH | =CH₂ | H | |

Table VIB-continued

| $R_1, R_2$ | $R_3$ | $R_4$ | $R_5$ | $R_6$ | $R_7$ | $R_8$ |
|---|---|---|---|---|---|---|
| $CH_3$ | $CH_3$ | $C_2H_5$ | OH | | $=CH_2$ | H |
| $CH_3$ | $C_2H_5$ | $C_2H_5$ | OH | | $=CH_2$ | H |
| $CH_3$ | $n\text{-}C_3H_7$ | $n\text{-}C_3H_7$ | OH | | $=CH_2$ | H |
| $CH_3$ | $n\text{-}C_4H_9$ | $n\text{-}C_4H_9$ | OH | | $=CH_2$ | H |
| $CH_3$ | H | $CH_2\text{—COOH}$ | OH | | $=CH_2$ | H |
| $CH_3$ | H | $CH_2\text{—COOC}_2H_5$ | OH | | $=CH_2$ | H |
| $CH_3$ | H | $CH_3\text{—CH—COOH}$ | OH | | $=CH_2$ | H |
| $CH_3$ | H | $CH_3\text{—CH—COOC}_2H_5$ | OH | | $=CH_2$ | H |
| $CH_3$ | H | $\text{—CH}_2\text{—CH}_2\text{—COOH}$ | OH | | $=CH_2$ | H |
| $CH_3$ | H | $\text{—CH}_2\text{—CH}_2\text{—COOC}_2H_5$ | OH | | $=CH_2$ | H |
| $CH_3$ | H | $\text{—(CH}_2)_4\text{—CH—COOH}$ with $NH_2$ | OH | | $=CH_2$ | H |
| $CH_3$ | \multicolumn{2}{l|}{cyclopentyl (R_3, R_4 joined)} | OH | | $=CH_2$ | H |
| $CH_3$ | \multicolumn{2}{l|}{cyclohexyl (R_3, R_4 joined)} | OH | | $=CH_2$ | H |
| $CH_3$ | \multicolumn{2}{l|}{tetrahydropyranyl (O)} | OH | | $=CH_2$ | H |
| $CH_3$ | \multicolumn{2}{l|}{piperidinyl (N-H)} | OH | | $=CH_2$ | H |
| $CH_3$ | \multicolumn{2}{l|}{piperidinyl (N—$CH_3$)} | OH | | $=CH_2$ | H |
| $CH_3$ | \multicolumn{2}{l|}{piperidinyl (N—$C_2H_5$)} | OH | | $=CH_2$ | H |
| $CH_3$ | \multicolumn{2}{l|}{piperidinyl (N—$C_2H_4OH$)} | OH | | $=CH_2$ | H |
| $C_2H_5$ | $CH_3$ | $CH_3$ | OH | | $=CH_2$ | H |
| $C_2H_5$ | $CH_3$ | $C_2H_5$ | OH | | $=CH_2$ | H |
| $C_2H_5$ | $C_2H_5$ | $C_2H_5$ | OH | | $=CH_2$ | H |
| $C_2H_5$ | $n\text{-}C_3H_7$ | $n\text{-}C_3H_7$ | OH | | $=CH_2$ | H |
| $C_2H_5$ | $n\text{-}C_4H_9$ | $n\text{-}C_4H_9$ | OH | | $=CH_2$ | H |
| $C_2H_5$ | H | $CH_2\text{—COOH}$ | OH | | $=CH_2$ | H |
| $C_2H_5$ | H | $CH_2\text{—COOC}_2H_5$ | OH | | $=CH_2$ | H |

Table VIB-continued

| R₁, R₂ | R₃ | R₄ | R₅ | R₆ | R₇ | R₈ |
|---|---|---|---|---|---|---|
| $C_2H_5$ | H | $CH_3-CH(-)-COOH$ | OH | | $=CH_2$ | H |
| $C_2H_5$ | H | $CH_3-CH(-)-COOC_2H_5$ | OH | | $=CH_2$ | H |
| $C_2H_5$ | H | $-CH_2-CH_2-COOH$ | OH | | $=CH_2$ | H |
| $C_2H_5$ | H | $-CH_2-CH_2-COOC_2H_5$ | OH | | $=CH_2$ | H |
| $C_2H_5$ | H | $-(CH_2)_4-CH(NH_2)-COOH$ | OH | | $=CH_2$ | H |
| $C_2H_5$ | \multicolumn{2}{c|}{ cyclopentyl} | OH | | $=CH_2$ | H |
| $C_2H_5$ | \multicolumn{2}{c|}{ cyclohexyl} | OH | | $=CH_2$ | H |
| $C_2H_5$ | \multicolumn{2}{c|}{ tetrahydropyranyl} | OH | | $=CH_2$ | H |
| $C_2H_5$ | \multicolumn{2}{c|}{ piperidinyl} | OH | | $=CH_2$ | H |
| $C_2H_5$ | \multicolumn{2}{c|}{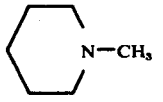 N-CH₃ piperidinyl} | OH | | $=CH_2$ | H |
| $C_2H_5$ | \multicolumn{2}{c|}{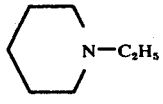 N-C₂H₅ piperidinyl} | OH | | $=CH_2$ | H |
| $C_2H_5$ | \multicolumn{2}{c|}{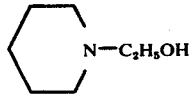 N-C₂H₄OH piperidinyl} | OH | | $=CH_2$ | H |
| $n-C_3H_7$ | $CH_3$ | $CH_3$ | OH | | $=CH_2$ | H |
| $n-C_3H_7$ | $CH_3$ | $C_2H_7$ | OH | | $=CH_2$ | H |
| $n-C_3H_7$ | $C_2H_5$ | $C_2H_5$ | OH | | $=CH_2$ | H |
| $n-C_3H_7$ | $n-C_3H_7$ | $n-C_3H_7$ | OH | | $=CH_2$ | H |
| $n-C_3H_7$ | $n-C_4H_9$ | $n-C_4H_9$ | OH | | $=CH_2$ | H |
| $n-C_3H_7$ | H | $CH_2-COOH$ | OH | | $=CH_2$ | H |
| $n-C_3H_7$ | H | $CH_2-COOC_2H_5$ | OH | | $=CH_2$ | H |
| $n-C_3H_7$ | H | $CH_3-CH(-)-COOH$ | OH | | $=CH_2$ | H |
| $n-C_3H_7$ | H | $CH_3-CH(-)-COOC_2H_5$ | OH | | $=CH_2$ | H |
| $n-C_3H_7$ | H | $-CH_2-CH_2-COOH$ | OH | | $=CH_2$ | H |
| $n-C_3H_7$ | $-CH_2-CH_2-COOC_2H_5$ | OH | | $=CH_2$ | H | |

Table VIB-continued

| R₁, R₂ | R₃ | R₄ | R₅ | R₆ | R₇ | R₈ |
|---|---|---|---|---|---|---|
| n-C₃H₇ | H | −(CH₂)₄−CH(NH₂)−COOH | OH | | =CH₂ | H |
| n-C₃H₇ | | 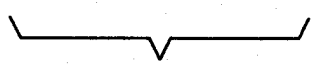 (cyclopentyl) | OH | | =CH₂ | H |
| n-C₃H₇ | |  (cyclohexyl) | OH | | =CH₂ | H |
| n-C₃H₇ | |  (tetrahydropyranyl, O) | OH | | =CH₂ | H |
| n-C₃H₇ | |  (piperidinyl, N) | OH | | =CH₂ | H |
| n-C₃H₇ | |  (N−CH₃ piperidinyl) | OH | | =CH₂ | H |
| n-C₃H₇ | | 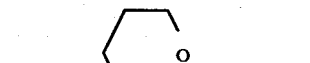 (N−C₂H₅ piperidinyl) | OH | | =CH₂ | H |
| n-C₃H₇ | | 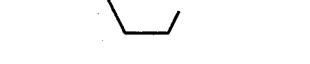 (N−C₂H₅OH piperidinyl) | OH | | =CH₂ | H |
| n-C₄H₉ | CH₃ | CH₃ | OH | | =CH₂ | H |
| n-C₄H₉ | CH₃ | C₂H₅ | OH | | =CH₂ | H |
| n-C₄H₉ | C₂H₅ | C₂H₅ | OH | | =CH₂ | H |
| n-C₄H₉ | n-C₃H₇ | n-C₃H₇ | OH | | =CH₂ | H |
| n-C₄H₉ | n-C₄H₉ | n-C₄H₉ | OH | | =CH₂ | H |
| n-C₄H₉ | H | CH₂−COOH | OH | | =CH₂ | H |
| n-C₄H₉ | H | CH₂−COOC₂H₅ | OH | | =CH₂ | H |
| n-C₄H₉ | H | CH₃−CH−COOH | OH | | =CH₂ | H |
| n-C₄H₉ | H | CH₃−CH−COOC₂H₅ | OH | | =CH₂ | H |
| n-C₄H₉ | H | −CH₂−CH₂−COOH | OH | | =CH₂ | H |
| n-C₄H₉ | H | −CH₂−CH₂−COOC₂H₅ | OH | | =CH₂ | H |
| n-C₄H₉ | H | −(CH₂)₄−CH(NH₂)−COOH | OH | | =CH₂ | H |
| n-C₄H₉ | | 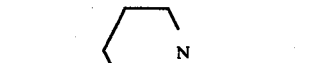 (cyclopentyl) | OH | | =CH₂ | H |

Table VIB-continued

| R₁, R₂ | R₃ | R₄ | R₅ | R₆ | R₇ | R₈ |
|---|---|---|---|---|---|---|
| n-C₄H₉ |  |  | OH |  | =CH₂ | H |
| n-C₄H₉ |  |  | OH |  | =CH₂ | H |
| n-C₄H₉ |  |  | OH |  | =CH₂ | H |
| n-C₄H₉ |  | 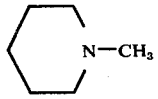 | OH |  | =CH₂ | H |
| n-C₄H₉ |  | 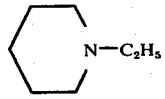 | OH |  | =CH₂ | H |
| n-C₄H₉ |  | 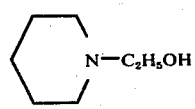 | OH |  | =CH₂ | H |

The following Examples illustrate the invention.

EXAMPLE 1

N-(1,1-Diethoxy-2-pyrrolidinoethyl)-tetracycline 2.22 g of tetracycline base were dissolved in a mixture of 2.4 g of glyoxal-diethyl-monoacetal, 0.33 g of pyrrolidine and 10 ml of anhydrous methylene chloride and stirred at room temperature for 3 hours under an atmosphere of nitrogen. The solution was concentrated on a rotary evaporator to one third of its original volume. By pouring the solution into 50 ml of ether, the N-(1,1-diethoxy-2-pyrrolidinoethyl)-tetracycline was obtained in a well filtrable form. Yield: 2.0 g; M.p.: 117° C.

EXAMPLE 2

N-(1,1-Diethoxy-2-pyrrolidinoethyl)-tetracycline

A solution of 2.22 g of tetracycline base in 10 ml of methylene chloride was combined with 1,1-diethoxy-2,2-dipyrrolidinylethane prepared by the reaction of 1.32 g of glyoxal-diethyl-monoacetal and 1.42 g of pyrrolidine and the whole was stirred for 3 hours at room temperature under an atmosphere of nitrogen. The solution was concentrated and the product was precipitated with ether. M.p.: 117° C.

EXAMPLE 3

N-(1,1-Diethoxy-2-pyrrolidinoethyl)-tetracycline hydrochloride 2.4 g of tetracycline hydrochloride in 50 ml of isopropanol were combined with a mixture of 0.33 g of pyrrolidine and 2.4 g of glyoxal-diethyl-monoacetal and the whole was stirred for 5 hours at room temperature. The solvent was removed as far as possible under reduced pressure. Upon addition of ether, the N-(1,1-diethoxy-2-pyrrolidinoethyl)-tetracycline hydrochloride was obtained in solid form.

In the same manner as described in Example 1, there were obtained the compounds specified in Examples 4 to 20. The melting points indicated for them are decomposition points.

EXAMPLE 4

N-(1,1-Diethoxy-2-N-methylpiperazinoethyl)-tetracycline

M.p. 112° C.

EXAMPLE 5

N-(1,1-Diethoxy-2-diethylaminoethyl)-tetracycline

M.p. 92° to 98° C.

EXAMPLE 6

N-(1,1-Diethoxy-2-dimethylaminoethyl)-tetracycline

M.p. 111° to 116° C.

EXAMPLE 7

N-(1,1-Diethoxy-2-morpholinoethyl)-tetracycline

M.p. 106° C.

EXAMPLE 8

N-(1,1-Diethoxy-2-piperidinoethyl)-tetracycline

M.p. 95° to 105° C.

EXAMPLE 9

N-(1,1-Diethoxy-2-dimethylaminoisopropylaminoethyl)-tetracycline

M.p. 123° C.

EXAMPLE 10

N-(1,1-Diethoxy-2-n-propylaminoethyl)-tetracycline

M.p. 142° C.

EXAMPLE 11

N-(1,1-Diethoxy-2-n-butylaminoethyl)-tetracycline

M.p. 101° to 114° C.

EXAMPLE 12

N-(1,1-Dimethoxy-2-piperidinoethyl)-tetracycline

M.p. 140° C.

EXAMPLE 13

N-(1,1-Dimethoxy-2-dimethylaminoethyl)-tetracycline

M.p. 141° C.

EXAMPLE 14

N-(1,1-Dimethoxy-2-diethylaminoethyl)-tetracycline

M.p. 137° C.

EXAMPLE 15

N-(1,1-Dimethoxy-2-N-methylpiperazinoethyl)-tetracycline

M.p. 146° C.

EXAMPLE 16

N-(1,1-Dimethoxymorpholinoethyl)-tetracycline

M.p. 140° C.

EXAMPLE 17

N-(1,1-Dimethoxy-2-dimethylaminoisopropylaminoethyl)-tetracycline

M.p. 113° C.

EXAMPLE 18

N-(1,1-Dimethoxy-2-hydroxyethylaminoethyl)-tetracycline

M.p. 102° C.

EXAMPLE 19

N-(1,1-Dimethoxy-2-n-butylaminoethyl)-tetracycline

M.p. 113° C.

EXAMPLE 20

N-(1,1-Dimethoxy-2-pyrrolidinoethyl)-desmethylchlorotetracycline

EXAMPLE 21

N-(1,1-Diethoxy-2-piperidinoethyl)-tetracycline citrate 2.22 g of tetracycline base were dissolved in a mixture of 2.4 g of glyoxal-diethylmonoacetal, 0.4 g of piperidine and 10 ml of anhydrous methylene chloride and the whole was stirred for 3 hours at room temperature under an atmosphere of nitrogen. A solution of 0.96 g of citric acid in 3 ml of ethanol was added, the mixture was concentrated under reduced pressure and the N-(1,1-diethoxy-2-piperidinoethyl)-tetracycline was precipitated by the addition of ether.

EXAMPLE 22

N-(1,1-Dimethoxy-2-morphonlinoethyl)-oxytetracycline 2.3 g of oxytetracycline base were introduced into a solution of 0.48 g of morpholine and 2.2 g of glyoxal-dimethyl-monoacetal in 10 ml of dimethylformamide. After having stirred for 3 hours under an atmosphere of nitrogen, the solution was concentrated under reduced pressure and the product was precipitated by the addition of 50 ml of ether.

Yield: 1.5 g; M.p. 110° C.

The compounds specified in the Examples 23 to 33 were prepared in a manner analogous to that described in Example 22.

EXAMPLE 23

N-(1,1-Dimethoxy-2-pyrrolidinoethyl)-oxytetracycline

M.p. 115° C.

EXAMPLE 24

N-(1,1-Dimethoxy-2-piperidinoethyl)-oxytetracycline

EXAMPLE 25

N-(1,1-Dimethoxy-2-N-methylpiperazinoethyl)-oxytetracycline

M.p. 119° C.

EXAMPLE 26

N-(1,1-Dimethoxy-2-N-diethylaminoethyl)-oxytetracycline

M.p. 101° C.

EXAMPLE 27

N-(1,1-Dimethoxy-2-N-dimethylaminoethyl)-oxytetracycline

M.p. 116° C.

EXAMPLE 28

N-(1,1-Diethoxy-2-pyrrolidinoethyl)-oxytetracycline

M.p. from 104° to 109° C.

EXAMPLE 29

N-(1,1-Diethoxy-2-diethylaminoethyl)-oxytetracycline

M.p. from 86° to 102° C.

EXAMPLE 30

N-(1,1-Diethoxy-2-dimethylaminoethyl)-oxytetracycline

M.p. from 86° to 105° C.

EXAMPLE 31

N-(1,1-Diethoxy-2-morpholinoethyl)-oxytetracycline

M.p. 85° to 105° C.

EXAMPLE 32

N-(1,1-Diethoxy-2-piperidinoethyl)-oxytetracycline

M.p. from 99° to 109° C.

EXAMPLE 33

N-(1,1-Diethoxy-2-N-methylpiperazinoethyl)-oxytetracycline

M.p. from 103° to 117° C.

We claim:
1. A tetracycline of the formula

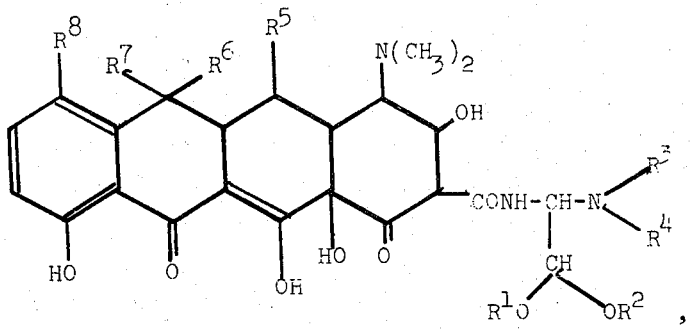

and physiologically tolerated salts thereof, wherein R¹ and R² are the same or different and are alkyl having 1 to 5 carbon atoms; R⁵ and R⁶, taken alone, are the same or different and are hydrogen or hydroxy; R⁷, taken alone, is hydrogen or methyl; or R⁶ and R⁷ taken together are methylene; R⁸ is hydrogen, chlorine, bromine or di-lower alkyl amino having 1 to 4 carbon atoms; R³, taken alone, is alkyl having 1 to 4 carbon atoms having at least one 5- or 6-membered heterocyclic substituent wherein the hetero atom is at least one member selected from the group consisting of oxygen and nitrogen; R⁴, taken alone, is hydrogen, alkyl having 1 to 6 carbon atoms, or alkyl having 1 to 6 carbon atoms having at lesst one substituent selected from the group consisting of hydroxy, di-lower alkyl amino, di-lower alkyl carbamoyl, lower alkoxy carbonyl, phenyl, a 5- or 6-membered heterocyclic substituent wherein the hetero atom is at least one member selected from the group consisting of oxygen and nitrogen, cycloalkyl having 5 to 7 carbon atoms, carboxy, and carboxy and amino; and R³ and R⁴, taken together with the nitrogen atom to which they are attached, form a 5- or 6-membered nitrogen heterocycle which may be interrupted by a further nitrogen or oxygen atom and which may be substituted by lower alkyl, hydroxy lower alkyl, carboxy lower alkyl, hydroxy, or carbonyl.

2. A compound as in claim 1 which is N-(1,1-diethoxy-2-pyrrolidino-ethyl) tetracycline.

3. A method for making a compound as in claim 1 which comprises reacting a tetracycline of the formula

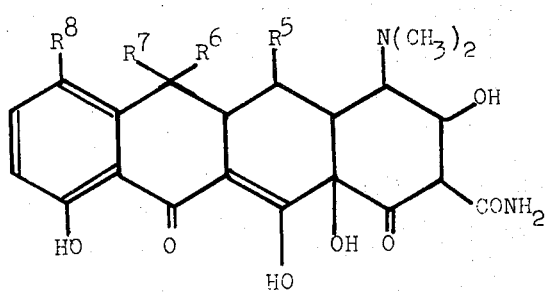

with an aldehyde of the formula

and an amine of the formula

R³
 \
  NH,
 /
R⁴ wherein R¹ - R⁸ have the same meanings as in claim 1.

4. A tetracycline of the formula

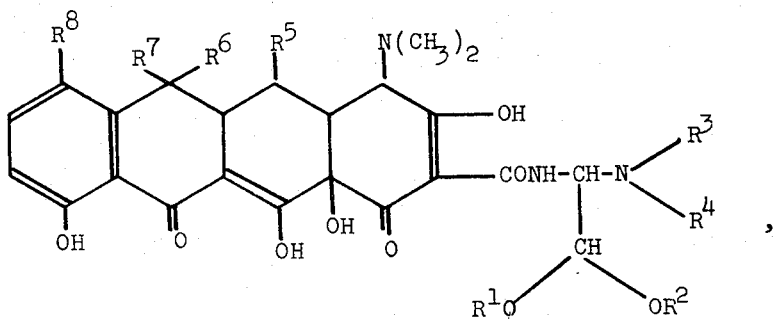

and physiologically tolerated salts thereof, wherein R¹ and R², taken alone, are the same or different and are alkyl having 1 to 5 carbon atoms; R¹ and R², taken together, are ethylene or propylene; R³ and R⁴, taken alone, are the same or different, are hydrogen, straight-chain or branched alkyl having 1 to 6 carbon atoms, straight-chain or branched alkyl having 1 to 6 carbon atoms which is substituted by at least one member selected from the group consisting of hydroxy, di-lower alkyl-amino, di-lower alkyl-carbamoyl, lower alkoxy-carbonyl, phenyl, a 5- or 6-membered heterocyclic substituent wherein the hetero atom is at least one member selected from the group consisting of oxygen and nitrogen, cycloalkyl having 5 to 7 carbon atoms, carboxy, and carboxy together with amino; R³ and R⁴, taken together with the nitrogen atom to which they are attached, form a 5- or 6-membered heterocycle which may be interrupted by a further nitrogen or oxygen atom and which may be substituted by lower alkyl, hydroxy lower alkyl, carboxy lower alkyl, hydroxy, or carbonyl; $R^5$ and $R^6$ are the same or different and are hydrogen or hydroxy; $R^7$ is hydrogen or methyl; $R^6$ and $R^7$, taken together, are methylene; and $R^8$ is hydrogen, chlorine, bromine, or di-alkyl amino in which the alkyl groups each have 1 to 4 carbon atoms.

5. The method of making a tetracycline as in claim 4 which comprises reacting a tetracycline of the formula

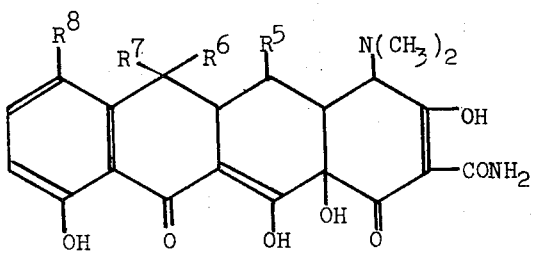

with an aldehyde of the formula

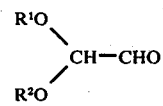

and an amine of the formula

wherein $R^1 - R^8$ have their earlier meanings.

6. The method as in claim 5 wherein the tetracycline product is subsequently acidified to form a physiologically tolerated salt thereof.

7. The method as in claim 5 wherein the tetracycline reagent or said amine are reacted in the form of a salt thereof.

8. The method as in claim 5 which is carried out in two stages as a transaminoalkylation.

9. An antibacterially-active pharmaceutical composition comprising a tetracycline or salt thereof as in claim 4 in combination with a pharmaceutical excipient.

10. The method of making a pharmaceutical composition which comprises bringing a tetracycline or salt thereof as in claim 4, alone or in combination with a pharmaceutical excipient, into a therapeutically-administrable form.

* * * * *

UNITED STATES PATENT AND TRADEMARK OFFICE
CERTIFICATE OF CORRECTION

PATENT NO. : 3,993,694
DATED : November 23, 1976
INVENTOR(S) : Martin et al.

It is certified that error appears in the above—identified patent and that said Letters Patent are hereby corrected as shown below:

In Claims 1 and 3 (Column 167), the right ring of the tetracycline structure should have a double bond (||) between the 2-carbon atom (bearing an OH group and adjacent to the $N(CH_3)_2$-substituted carbon atom) and the 3-carbon atom substituted by -CONH- etc. (Claim 1) and -$CONH_2$ (Claim 3), as in the tetracycline structural formulae of claims 4 and 5, respectively.

Signed and Sealed this

Thirteenth Day of December 1977

[SEAL]

Attest:

RUTH C. MASON
*Attesting Officer*

LUTRELLE F. PARKER
*Acting Commissioner of Patents and Trademarks*